(12) United States Patent
Pätzold et al.

(10) Patent No.: US 11,541,081 B2
(45) Date of Patent: *Jan. 3, 2023

(54) METHODS AND COMPOSITIONS FOR CHANGING THE COMPOSITION OF THE SKIN MICROBIOME USING COMPLEX MIXTURES OF BACTERIAL STRAINS

(71) Applicant: S-Biomedic NV, Beerse (BE)

(72) Inventors: Bernhard Pätzold, Magdeburg (DE); Marc Güell, Barcelona (ES)

(73) Assignee: S-Biomedic NV, Beerse (BE)

( * ) Notice: Subject to any disclaimer, the term of this patent is extended or adjusted under 35 U.S.C. 154(b) by 515 days.

This patent is subject to a terminal disclaimer.

(21) Appl. No.: 16/343,277

(22) PCT Filed: Oct. 19, 2017

(86) PCT No.: PCT/IB2017/001481
§ 371 (c)(1),
(2) Date: Apr. 18, 2019

(87) PCT Pub. No.: WO2018/073651
PCT Pub. Date: Apr. 26, 2018

(65) Prior Publication Data
US 2019/0314428 A1 Oct. 17, 2019
US 2021/0187043 A9 Jun. 24, 2021

Related U.S. Application Data

(60) Provisional application No. 62/536,761, filed on Jul. 25, 2017, provisional application No. 62/410,329, filed on Oct. 19, 2016.

(51) Int. Cl.
| | | |
|---|---|---|
| *C12N 1/20* | (2006.01) | |
| *A61K 35/741* | (2015.01) | |
| *A61P 17/10* | (2006.01) | |
| *A61K 9/00* | (2006.01) | |
| *A61K 9/06* | (2006.01) | |
| *A61K 47/38* | (2006.01) | |
| *A61K 47/42* | (2017.01) | |

(52) U.S. Cl.
CPC .......... *A61K 35/741* (2013.01); *A61K 9/0014* (2013.01); *A61K 9/06* (2013.01); *A61K 47/38* (2013.01); *A61K 47/42* (2013.01); *A61P 17/10* (2018.01)

(58) Field of Classification Search
CPC .................................................. A61K 35/741
See application file for complete search history.

(56) References Cited

U.S. PATENT DOCUMENTS

| | | |
|---|---|---|
| 5,650,149 A | 7/1997 | Okabe |
| 6,743,609 B1 | 6/2004 | Rosson et al. |
| 6,821,770 B1 | 11/2004 | Hogan |
| 6,982,273 B1 | 1/2006 | Majeed et al. |
| 7,919,250 B2 | 4/2011 | Blaser et al. |
| 9,889,165 B2 | 2/2018 | Taylor et al. |
| 10,774,305 B2 | 9/2020 | Pätzold et al. |
| 11,103,443 B2 | 8/2021 | Rasochova et al. |
| 2006/0286054 A1 | 12/2006 | Gomez |
| 2010/0260695 A1 | 10/2010 | Durke-Colvin et al. |
| 2011/0014248 A1 | 1/2011 | Castiel et al. |
| 2013/0289005 A1 | 10/2013 | Guthery |
| 2014/0234260 A1 | 8/2014 | Borody |
| 2014/0363398 A1 | 12/2014 | Jones et al. |
| 2015/0037285 A1 | 2/2015 | Blaser et al. |
| 2015/0050245 A1 | 2/2015 | Herman et al. |
| 2015/0086581 A1* | 3/2015 | Li ........................... C12Q 1/689 424/190.1 |
| 2015/0361436 A1 | 12/2015 | Hitchcock et al. |
| 2016/0151427 A1 | 6/2016 | Whitlock et al. |
| 2017/0058328 A1 | 3/2017 | Li et al. |
| 2017/0065647 A1 | 3/2017 | Kim et al. |
| 2018/0142202 A1* | 5/2018 | Patzold ................ A61K 35/74 |
| 2019/0314428 A1* | 10/2019 | Pätzold .................. A61K 9/06 |
| 2020/0392452 A1* | 12/2020 | Pätzold .................. C12N 1/20 |
| 2021/0187043 A9* | 6/2021 | Pätzold .................. A61K 9/06 |
| 2022/0000762 A1 | 1/2022 | Lood et al. |

FOREIGN PATENT DOCUMENTS

| | | | |
|---|---|---|---|
| EP | 3 139 939 A1 | 3/2017 | |
| EP | 3 158 054 A1 | 4/2017 | |
| EP | 2 825 676 B1 | 12/2017 | |
| EP | 3 360 560 A1 | 8/2018 | |
| EP | 3528825 A1 * | 8/2019 | ........... A61K 35/741 |
| WO | WO 2011/152566 A2 | 12/2011 | |
| WO | WO 2012/153206 A1 | 11/2012 | |
| WO | WO 2013/067185 A1 | 5/2013 | |
| WO | WO 2013/142378 A9 | 9/2013 | |

(Continued)

OTHER PUBLICATIONS

Karoglan et al, Acta DErm Venereol., 2019, 99:1253-1257. E-published: Sep. 25, 2019 (Year: 2019).*
Karoglan et al, 45th annual Meeting of Arbeitsgemeinschaft Dermatologische Forschung (ADF), Mar. 7-10, 2018, p. e26, Abstract No. P061.(Year: 2018).*
Liew-Littorin et al, Anaerobe 2019., 59:54-60. Avalable online:May 7, 2019 (Year: 2019).*
O'Neill et al, J of Investigative Dermatology, May 2018, vol. 138, No. 5, Supplement 1pp. S173. Abstract No. 1023 (Year : 2018).*
Paetzold et al, Microbiome. 2019. 7:97, 9 pages, published online: Jun. 24, 2019. (Year: 2019).*
Scholzetal, PLoS ONE, 2014, 9/8:e104199, 7 pages, published: Aug. 11, 2014 (Year: 2014).*
Eady et al, Journal of Investigative Dermatology, 2013. 133:2294-2295. published online: Jul. 11, 2013 (Year: 2013).*

(Continued)

*Primary Examiner* — Albert M Navarro
(74) *Attorney, Agent, or Firm* — Wolf, Greenfield & Sacks, P.C.

(57) ABSTRACT

Aspects of the invention relate to compositions comprising two or more live bacterial strains for topical administration to the skin, wherein the two or more live bacterial strains are *Propionibacterium acnes* (*P. acnes*) bacterial strains, and methods for use.

18 Claims, 13 Drawing Sheets

Specification includes a Sequence Listing.

(56) References Cited

FOREIGN PATENT DOCUMENTS

| | | | |
|---|---|---|---|
| WO | WO 2015/171899 A1 | 11/2015 | |
| WO | WO 2015/195845 A1 | 12/2015 | |
| WO | WO 2016/172196 A1 | 10/2016 | |
| WO | WO 2017/044835 A1 | 3/2017 | |
| WO | WO 2017/136738 A2 | 8/2017 | |
| WO | WO 2017/147507 A1 | 8/2017 | |
| WO | WO 2017/168263 A1 | 10/2017 | |
| WO | WO 2017/184992 A1 | 10/2017 | |
| WO | WO 2017/185016 A1 | 10/2017 | |
| WO | WO 2017/185018 A1 | 10/2017 | |
| WO | WO 2018/060799 A1 | 4/2018 | |
| WO | WO-2018073651 A1 * | 4/2018 | ........... A61K 38/018 |
| WO | WO 2019/238968 A1 | 12/2019 | |
| WO | WO 2020/099663 A1 | 5/2020 | |
| WO | WO 2021/063526 A1 | 4/2021 | |
| WO | WO 2021/063527 A1 | 4/2021 | |
| WO | WO 2021/063528 A1 | 4/2021 | |
| WO | WO 2021/063529 A1 | 4/2021 | |
| WO | WO 2021/063530 A1 | 4/2021 | |
| WO | WO 2021/063531 A1 | 4/2021 | |
| WO | WO 2021/063532 A1 | 4/2021 | |
| WO | WO-2021063526 A1 * | 4/2021 | |
| WO | WO-2021063527 A1 * | 4/2021 | |
| WO | WO-2021063528 A1 * | 4/2021 | |
| WO | WO-2021063529 A1 * | 4/2021 | |
| WO | WO-2021063530 A1 * | 4/2021 | |
| WO | WO-2021063531 A1 * | 4/2021 | |
| WO | WO-2021063532 A1 * | 4/2021 | |

OTHER PUBLICATIONS

Fitz-Gibbon et al, Journal of Investigative Dermatology, 2013, 133:2152-2160. published online: Feb. 28, 2013 (Year: 2013).*

Perry et al, Expert Reviews. Anti Infect. Ther. 2011, 9(12):1149-1156. abstract only (Year: 2011).*

Dessinioti et al, Clinic in Dermatology, 2010, 28:2-7. (Year: 2010).*

Shaheen et al, British Journal Dermatology, 2011, 165:474-485 (Year: 2011).*

Scholz et al, PLoS ONE. Aug. 2014, 9(8): e104199, 8 pages, published Aug. 11, 2014 (Year: 2014).*

International Search Report and Written Opinion dated Jul. 29, 2016 for Application No. PCT/US2016/028241.

International Preliminary Report on Patentability dated Nov. 2, 2017 for Application No. PCT/US2016/028241.

International Search Report and Written Opinion dated Apr. 11, 2018 for Application No. PCT/IB2017/001481.

International Preliminary Report on Patentability dated May 2, 2019 for Application No. PCT/IB2017/001481.

Partial Extended European Search Report dated Oct. 15, 2018 for Application No. EP 16783755.8.

Extended European Search Report dated Jan. 23, 2019 for Application No. EP 16783755.8.

[No Author Listed] Human Microbiome Project Consortium. Structure, function and diversity of the healthy human microbiome. Nature. Jun. 13, 2012;486(7402):207-14. doi: 10.1038/nature11234.

[No Author Listed] The NIH Human Microbiome Project. Genome Res. Dec. 2009;19(12):2317-23. doi: 10.1101/gr.096651.109. Epub Oct. 9, 2009.

[No Author Listed] A Study of the Safety, Engraftment, and Action of NB01 in Adults With Moderate Acne. Clinical Trials.gov Identifier: NCT03450369. First posted: Mar. 1, 2018; study completion date: Jun. 18, 2018; last update posted: Nov. 28, 2018. Retrieved from the Internet https://clinicaltrials.gov/ct2/show/NCT03450369 on May 23, 2019. 16 pages.

[No Author Listed] Sigma-Aldrich Fatty Acid/FAME Application Guide: Analysis of Foods for Nutritional Services. Retrieved on May 7, 2018. https://www.google.com/url?sa=t&rct=j&q=&esrc=s&source=web&cd=1&ved=0ahUKEwji5rXDxvbaAhUFVt8KHZ0fC9YQFgg1MAA&url=https%3A%2F%2Fwww.researchgate.net%2Fprofile%2FDang_Nguyen_Thoai%2Fpost%2FWhat_is_valu_input_GC_analysis_for_fish_oil_fatty_acid_profile%2Fattachment%2F59d6351579197b8077992b09%2FAS%3A382926094127111%401468308103322%2Fdownload%2FFatty%2BAcid%2B-%2BFAME%2BApplication%2BGuide.pdf&usg=AOvVaw0LpU-YvUgLBa0RGwYBT5FK.

Allgaier et al., Elucidation of the Structure of Epidermin, a Ribosomally Synthesized, Tetracyclic Heterodetic Polypeptide Antibiotic. Angew. Chem. Int. Ed. Engl. 1985;24(12):1051-1053.

Allgaier et al., Epidermin: sequencing of a heterodetic tetracyclic 21-peptide amide antibiotic. Eur J Biochem. Oct. 1, 1986;160(1):9-22.

Barnard et al., Strains of the Propionibacterium acnes type III lineage are associated with the skin condition progressive macular hypomelanosis. Sci Rep. Aug. 24, 2016;6:31968. doi: 10.1038/srep31968.

Bek-Thomsen et al., Acne is not associated with yet-uncultured bacteria. J Clin Microbiol. Oct. 2008;46(10):3355-60. doi: 10.1128/JCM.00799-08. Epub Aug. 20, 2008.

Bek-Thomsen et al., Proteome analysis of human sebaceous follicle infundibula extracted from healthy and acne-affected skin. PLoS One. Sep. 19, 2014;9(9):e107908. doi: 10.1371/journal.pone.0107908. eCollection 2014.

Bonacci et al., Conjugated linoleic acid is a preferential substrate for fatty acid nitration. J Biol Chem. Dec. 28, 2012;287(53):44071-82. doi: 10.1074/jbc.M112.401356. Epub Nov. 9, 2012.

Bowe et al., Acne Vulgaris, Probiotics and the Gut-Brain-Skin Axis-Back to the Future?. Gut Pathogens. 2011;3:1-11.

Bruggemann et al., CRISPR/cas loci of type II Propionibacterium acnes confer immunity against acquisition of mobile elements present in type I P. acnes. PLoS One. 2012;7(3):e34171. doi: 10.1371/journal.pone.0034171. Epub Mar. 30, 2012.

Brzuszkiewicz et al., Comparative genomics and transcriptomics of Propionibacterium acnes. PLoS One. 2011;6(6):e21581. doi: 10.1371/journal.pone.0021581. Epub Jun. 27, 2011.

Churruca et al., Conjugated linoleic acid isomers: differences in metabolism and biological effects. Biofactors. Jan.-Feb. 2009;35(1):105-11. doi: 10.1002/biof.13.

Clavaud et al., Dandruff is associated with disequilibrium in the proportion of the major bacterial and fungal populations colonizing the scalp. PLoS One. 2013;8(3):e58203. doi: 10.1371/journal.pone.0058203. Epub Mar. 6, 2013. Erratum in: PLoS One. 2013;8(10). doi: 10.1371/annotation/bcff4a59-10b7-442a-8181-12fa69209e57.

Delmastro-Greenwood et al., Redox-dependent anti-inflammatory signaling actions of unsaturated fatty acids. Annu Rev Physiol. 2014;76:79-105. doi: 10.1146/annurev-physiol-021113-170341. Epub Oct. 16, 2013. Author manuscript.

Downing et al., Essential fatty acids and acne. J Am Acad Dermatol. Feb. 1986;14(2 Pt 1):221-5.

Flores et al., A direct PCR approach to accelerate analyses of human-associated microbial communities. PLoS One. 2012;7(9):e44563. doi: 10.1371/journal.pone.0044563. Epub Sep. 4, 2012.

Genbank Submission; NIH/NCBI, Accession No. CP003084: "Propionibacterium acnes ATCC 11828, complete genome.", GenBank Record created on Oct. 24, 2011. 4 pages.

Genbank Submission; NIH/NCBI, Accession No. CP003293: "Propionibacterium acnes HL096PA1, complete genome", GenBank Record created on Apr. 23, 2013. 2 pages.

Götz et al., Epidermin and gallidermin: Staphylococcal lantibiotics. Int J Med Microbiol. Jan. 2014;304(1):63-71. doi: 10.1016/j.ijmm.2013.08.012. Epub Sep. 4, 2013.

Gribbon et al., Interaction of Propionibacterium acnes with skin lipids in vitro. J Gen Microbiol. Aug. 1993;139(8):1745-51.

Grice, The skin microbiome. Nat Rev Microbiol. Apr. 2011;9(4):244-53. doi: 10.1038/nrmicro2537. Review. Erratum in: Nat Rev Microbiol. Aug. 2011;9(8):626.

Grice, The skin microbiome: potential for novel diagnostic and therapeutic approaches to cutaneous disease. Semin Cutan Med Surg. Jun. 2014;33(2):98-103.

Guy et al., Modeling acne in vitro. J Invest Dermatol. Jan. 1996;106(1):176-82.

Hogquist et al., Interleukin 1 is processed and released during apoptosis. Proc Natl Acad Sci U S A. Oct. 1, 1991;88(19):8485-9.

(56) References Cited

OTHER PUBLICATIONS

Horváth et al., Genome sequence of Propionibacterium acnes type II strain ATCC 11828. J Bacteriol. Jan. 2012;194(1):202-3. doi: 10.1128/JB.06388-11.

Hunyadkürti et al., Complete genome sequence of Propionibacterium acnes type IB strain 6609. J Bacteriol. Sep. 2011;193(17):4561-2. doi: 10.1128/JB.05372-11. Epub Jun. 24, 2011.

Iinuma et al., Involvement of Propionibacterium acnes in the augmentation of lipogenesis in hamster sebaceous glands in vivo and in vitro. J Invest Dermatol. Sep. 2009;129(9):2113-9. doi: 10.1038/jid.2009.46. Epub Mar. 12, 2009.

Im et al. Enzymes of carbohydrate metabolism in normal human sebaceous glands. J Invest Dermatol. Mar. 1974;62(3):153-60.

Isard et al., Propionibacterium acnes activates the IGF-1/IGF-1R system in the epidermis and induces keratinocyte proliferation. J Invest Dermatol. Jan. 2011;131(1):59-66. doi: 10.1038/jid.2010. 281. Epub Oct. 7, 2010.

Jasson et al., Different strains of Propionibacterium acnes modulate differently the cutaneous innate immunity. Exp Dermatol. Sep. 2013;22(9):587-92. doi: 10.1111/exd.12206.

Jensen, Characterization of health—associated *Propionibacterium acnes* strains. 60 ECTS Master Thesis in Biology for the degree cand. scient. Aarhus Universitet, Department of Biomedicine, Health, Denmark. Jan. 2016. 52 pages.

Kasimatis et al., Analysis of complete genomes of Propionibacterium acnes reveals a novel plasmid and increased pseudogenes in an acne associated strain. Biomed Res Int. 2013;2013:918320. doi: 10.1155/2013/918320. Epub May 13, 2013.

Kearney et al., Correlations between human skin bacteria and skin lipids. Br J Dermatol. May 1984;110(5):593-9.

King et al., A double-blind study of the effects of 13-cis-retinoic acid on acne, sebum excretion rate and microbial population. Br J Dermatol. Nov. 1982;107(5):583-90.

Ko et al., Differential susceptibility of Propionibacterium acnes, P. granulosum and P. avidum to free fatty acids. J Invest Dermatol. Dec. 1978;71(6):363-5.

Kong et al., Temporal shifts in the skin microbiome associated with disease flares and treatment in children with atopic dermatitis. Genome Res. May 2012;22(5):850-9. doi: 10.1101/gr.131029.111. Epub Feb. 6, 2012.

Kramer et al., Analysis of conjugated linoleic acid and trans 18:1 isomers in synthetic and animal products. Am J Clin Nutr. Jun. 2004;79(6 Suppl):1137S-1145S. doi: 10.1093/ajcn/79.6.1137S.

Liao et al., Survivability and long-term preservation of bacteria in water and in phosphate-buffered saline. Lett Appl Microbiol. 2003;37(1):45-50.

Liavonchanka et al., Structure and mechanism of the Propionibacterium acnes polyunsaturated fatty acid isomerase. Proc Natl Acad Sci U S A. Feb. 21, 2006;103(8):2576-81. Epub Feb. 13, 2006.

Makrantonaki et al., An update on the role of the sebaceous gland in the pathogenesis of acne. Dermatoendocrinol. Jan. 2011;3(1):41-9. doi: 10.4161/derm.3.1.13900.

Mcginley et al., Regional variations of cutaneous propionibacteria. Appl Environ Microbiol. Jan. 1978;35(1):62-6.

Mckain et al., Metabolism of conjugated linoleic acids and 18:1 fatty acids by ruminal bacteria: products and mechanisms. Microbiology. Feb. 2010;156(Pt 2):579-88. doi: 10.1099/mic.0.036442-0. Epub Nov. 19, 2009.

Mourelatos et al., Temporal changes in sebum excretion and propionibacterial colonization in preadolescent children with and without acne. Br J Dermatol. Jan. 2007;156(1):22-31.

Moya-Camarena et al., Conjugated linoleic acid is a potent naturally occurring ligand and activator of PPARalpha. J Lipid Res. Aug. 1999;40(8):1426-33.

Mudiyanselage et al., Ultraviolet a induces generation of squalene monohydroperoxide isomers in human sebum and skin surface lipids in vitro and in vivo. J Invest Dermatol. Jun. 2003;120(6):915-22.

Nagy et al., Distinct strains of Propionibacterium acnes induce selective human beta-defensin-2 and interleukin-8 expression in human keratinocytes through toll-like receptors. J Invest Dermatol. May 2005;124(5):931-8.

Oberemok et al., Acne Vulgaris, I: Pathogenesis and Diagnosis. Cutis. 2002;70:101-105.

Oh et al., Biogeography and individuality shape function in the human skin metagenome. Nature. Oct. 2, 2014;514(7520):59-64. doi: 10.1038/nature13786.

Oh et al., Temporal Stability of the Human Skin Microbiome. Cell. May 5, 2016;165(4):854-66. doi: 10.1016/j.cell.2016.04.008.

Ottaviani et al., Peroxidated squalene induces the production of inflammatory mediators in HaCaT keratinocytes: a possible role in acne vulgaris. J Invest Dermatol. Nov. 2006;126(11):2430-7. Epub Jun. 15, 2006.

Pappas et al., Sebum analysis of individuals with and without acne. Dermatoendocrinol. May 2009;1(3):157-61.

Pierre et al., Trans-10, cis-12 conjugated linoleic acid induced cell death in human colon cancer cells through reactive oxygen species-mediated ER stress. Biochim Biophys Acta. Apr. 2013;1831(4):759-68. doi: 10.1016/j.bbalip.2013.01.005. Epub Jan. 15, 2013.

Puhvel et al., Effect of fatty acids on the growth of Corynebacterium acnes in vitro. J Invest Dermatol. Jan. 1970;54(1):48-52.

Rivier et al., Peroxisome proliferator-activated receptor-alpha enhances lipid metabolism in a skin equivalent model. J Invest Dermatol. Apr. 2000;114(4):681-7.

Rohland et al., Cost-effective, high-throughput DNA sequencing libraries for multiplexed target capture. Genome Res. May 2012;22(5):939-46. doi: 10.1101/gr.128124.111. Epub Jan. 20, 2012.

Rosberg-Cody et al., Heterologous expression of linoleic acid isomerase from Propionibacterium acnes and anti-proliferative activity of recombinant trans-10, cis-12 conjugated linoleic acid. Microbiology. Aug. 2007;153(Pt 8):2483-90.

Scholz et al., Genome stability of Propionibacterium acnes: a comprehensive study of indels and homopolymeric tracts. Sci Rep. Feb. 9, 2016;6:20662. doi: 10.1038/srep20662.

Thielitz et al., A randomized investigator-blind parallel-group study to assess efficacy and safety of azelaic acid 15% gel vs. adapalene 0.1% gel in the treatment and maintenance treatment of female adult acne. J Eur Acad Dermatol Venereol. Apr. 2015;29(4):789-96. doi: 10.1111/jdv.12823. Epub Nov. 14, 2014.

Wang et al., Characterization of the major bacterial-fungal populations colonizing dandruff scalps in Shanghai, China, shows microbial disequilibrium. Exp Dermatol. May 2015;24(5):398-400. doi: 10.1111/exd.12684.

Wang et al., *Staphylococcus epidermidis* in the human skin microbiome mediates fermentation to inhibit the growth of Propionibacterium acnes: implications of probiotics in acne vulgaris. Appl Microbiol Biotechnol. Jan. 2014;98(1):411-24. doi: 10.1007/s00253-013-5394-8. Epub Nov. 22, 2013.

Westerhof et al., Propionibacterium acnes and the pathogenesis of progressive macular hypomelanosis. Arch Dermatol. Feb. 2004;140(2):210-4.

Yu et al., Different Propionibacterium acnes Phylotypes Induce Distinct Immune Responses and Express Unique Surface and Secreted Proteomes. J Invest Dermatol. Nov. 2016;136(11):2221-2228. doi: 10.1016/j.jid.2016.06.615. Epub Jul. 1, 2016.

Zouboulis, Acne and sebaceous gland function. Clin Dermatol. Sep.-Oct. 2004;22(5):360-6.

Azoulay et al., Isotretinoin therapy and the incidence of acne relapse: a nested case-control study. Br J Dermatol. Dec. 2007;157(6):1240-8. Epub Oct. 26, 2007.

Belkaid et al., Dialogue between skin microbiota and immunity. Science. Nov. 21, 2014;346(6212):954-9. doi: 10.1126/science. 1260144.

Berson et al., Current concepts in the treatment of acne: report from a clinical roundtable. Cutis. Jul. 2003;72(1 Suppl):5-13.

Deng et al., Linoleic acid isomerase from Propionibacterium acnes: purification, characterization, molecular cloning, and heterologous expression. Appl Biochem Biotechnol. Dec. 2007;143(3):199-211.

Dore et al., The influence of diet on the gut microbiota and its consequences for health. Curr Opin Biotechnol. Apr. 2015;32:195-199. doi: 10.1016/j.copbio.2015.01.002. Epub Jan. 20, 2015.

(56) References Cited

OTHER PUBLICATIONS

Draelos, Cosmeceuticals: undefined, unclassified, and unregulated. Clin Dermatol. Sep.-Oct. 2009;27(5):431-4. doi: 10.1016/j.clindermatol.2009.05.005.
Holmes, Potential role of microorganisms in the pathogenesis of rosacea. J Am Acad Dermatol. Dec. 2013;69(6):1025-32. doi: 10.1016/j.jaad.2013.08.006. Epub Sep. 5, 2013.
Karoglan et al., Safety and Efficacy of Topically Applied Selected *Cutibacterium acnes* Strains over Five Weeks in Patients with Acne Vulgaris: An Open-label, Pilot Study. Acta Derm Venereol. Dec. 1, 2019;99(13):1253-1257. doi: 10.2340/00015555-3323.
Letawe et al., Digital image analysis of the effect of topically applied linoleic acid on acne microcomedones. Clin Exp Dermatol. Mar. 1998;23(2):56-8.
Leyden, Current issues in antimicrobial therapy for the treatment of acne. J Eur Acad Dermatol Venereol. 2001;15 Suppl 3:51-5.
Mclane, Analysis of common side effects of isotretinoin. J Am Acad Dermatol. Nov. 2001;45(5):S188-94.
Nodake et al., Pilot study on novel skin care method by augmentation with *Staphylococcus epidermidis*, an autologous skin microbe—A blinded randomized clinical trial. J Dermatol Sci. Aug. 2015;79(2):119-26. doi: 10.1016/j.jdermsci.2015.05.001. Epub May 14, 2015.
Olle, Medicines from microbiota. Nat Biotechnol. Apr. 2013;31(4):309-15. doi: 10.1038/nbt.2548.
Paetzold et al., Skin microbiome modulation induced by probiotic solutions. Microbiome. Jun. 24, 2019;7(1):95. doi: 10.1186/s40168-019-0709-3.
Ross et al., Phenotypic and genotypic characterization of antibiotic-resistant Propionibacterium acnes isolated from acne patients attending dermatology clinics in Europe, the U.S.A., Japan and Australia. Br J Dermatol. Feb. 2001;144(2):339-46.
Schnell et al., Prepeptide sequence of epidermin, a ribosomally synthesized antibiotic with four sulphide-rings. Nature. May 19, 1988;333(6170):276-8.
Seidler et al., Meta-analysis comparing efficacy of benzoyl peroxide, clindamycin, benzoyl peroxide with salicylic acid, and combination benzoyl peroxide/clindamycin in acne. J Am Acad Dermatol. Jul. 2010;63(1):52-62. doi: 10.1016/j.jaad.2009.07.052. Epub May 21, 2010.
Sorenson et al., Mutagenesis of Propionibacterium acnes and analysis of two CAMP factor knock-out mutants. J Microbiol Methods. Nov. 2010;83(2):211-6. doi: 10.1016/j.mimet.2010.09.008. Epub Sep. 17, 2010.
Tripathi et al., Side effects of common acne treatments. Expert Opin Drug Saf. Jan. 2013;12(1):39-51. doi: 10.1517/14740338.2013.740456. Epub Nov. 20, 2012.
Van Nood et al., Duodenal infusion of donor feces for recurrent Clostridium difficile. N Engl J Med. Jan. 31, 2013;368(5):407-15. doi: 10.1056/NEJMoa1205037. Epub Jan. 16, 2013.
Yu et al., Typing of Propionibacterium acnes: a review of methods and comparative analysis. Br J Dermatol. 2015;172(5):1204-9. doi: 10.1111/bjd.13667. Epub Apr. 9, 2015.
Zhao, Genomics: The tale of our other genome. Nature. Jun. 17, 2010;465(7300):879-80. doi: 10.1038/465879a.
Zouboulis, Propionibacterium acnes and sebaceous lipogenesis: a love-hate relationship? J Invest Dermatol. Sep. 2009;129(9):2093-6. doi: 10.1038/jid.2009.190.
U.S. Appl. No. 15/567,941, filed Oct. 19, 2017, Pätzold et al.
EP 16783755.8, Oct. 15, 2018, Partial Extended European Search Report.
EP 16783755.8, Jan 23, 2019, Extended European Search Report.
PCT/US2016/028241, Jul. 29, 2016, International Search Report and Written Opinion.
PCT/US2016/028241, Nov. 2, 2017, International Preliminary Report of Patentability.
PCT/IB2017/001481, Apr. 11, 2018, International Search Report and Written Opinion.
PCT/IB2017/001481, May 2, 2019, International Preliminary Report on Patentability.

Ahmed et al., High levels of 8-hydroxy-2'-deoxyguanosine appear in normal human epidermis after a single dose of ultraviolet radiation. Br J Dermatol. Feb. 1999;140(2):226-31. doi: 10.1111/j.1365-2133.1999.02653.x.
Allhorn et al., A novel enzyme with antioxidant capacity produced by the ubiquitous skin colonizer Propionibacterium acnes. Sci Rep. Nov. 2, 2016;6:36412. doi: 10.1038/srep36412.
Andersson et al., Common skin bacteria protect their host from oxidative stress through secreted antioxidant RoxP. Sci Rep. Mar. 5, 2019;9(1):3596. doi: 10.1038/s41598-019-40471-3.
Arthur, The glutathione peroxidases. Cell Mol Life Sci. Dec. 2000;57(13-14): 1825-35. doi: 10.1007/pl00000664.
Cadet et al., Ultraviolet radiation-mediated damage to cellular DNA. Mutat Res. Apr. 1, 2005;571(1-2):3-17. doi: 10.1016/j.mrfmmm.2004.09.012. Epub Jan. 26, 2005.
Chen et al., The Human Oral Microbiome Database: a web accessible resource for investigating oral microbe taxonomic and genomic information. Database (Oxford). Jul. 6, 2010;2010:baq013. doi: 10.1093/database/baq013.
Ertürk et al., Highly sensitive detection and quantification of the secreted bacterial benevolence factor RoxP using a capacitive biosensor: A possible early detection system for oxidative skin diseases. PLoS One. Mar. 1, 2018;13(3):e0193754. doi:10.1371/journal.pone.0193754. PMID: 29494704.
Fitz-Gibbon et al., Propionibacterium acnes strain populations in the human skin microbiome associated with acne. J Invest Dermatol. Sep. 2013;133(9):2152-60. doi: 10.1038/jid.2013.21. Epub Jan. 21, 2013.
Foster et al., 651 Organic Osmolytes Improve Cell vol. Regulation of Aged Human Keratinocytes. J of Investigative Dermatology. May 2018; 138(5):S111. doi: 10.1016/j.jid.2018.03.660.
Genbank Submission; NIH/NCBI Accession No. AE017283.1. Bruggemann et al., Jan. 30, 2014. 427 pages.
Genbank Submission; NIH/NCBI Accession No. AFJ11206.1. Lood et al., Jun. 30, 2012. 1 page.
Genbank Submission; NIH/NCBI Accession No. AFJ11207.1. Lood et al., Jun. 30, 2012. 1 page.
Genbank Submission; NIH/NCBI Accession No. AFJ11208.1. Lood et al., Jun. 30, 2012. 1 page.
Genbank Submission; NIH/NCBI Accession No. AFJ11209.1. Lood et al., Jun. 30, 2012. 1 page.
Genbank Submission; NIH/NCBI Accession No. AFJ11210.1. Lood et al., Jun. 30, 2012. 1 page.
Genbank Submission; NIH/NCBI Accession No. AFJ11211.1. Lood et al., Jun. 30, 2012. 1 page.
Genbank Submission; NIH/NCBI Accession No. AFJ11212.1. Lood et al., Jun. 30, 2012. 1 page.
Genbank Submission; NIH/NCBI Accession No. AFJ11213.1. Lood et al., Jun. 30, 2012. 1 page.
Genbank Submission; NIH/NCBI Accession No. AFJ11214.1. Lood et al., Jun. 30, 2012. 1 page.
Genbank Submission; NIH/NCBI Accession No. AAT83657.1. Bruggemann et al., Jan. 30, 2014.
Genbank Submission; NIH/NCBI Accession No. CP001977.1. Harkins et al., Dec. 11, 2013. 519 pages.
Genbank Submission; NIH/NCBI Accession No. CP002409.1. Brzuszkiewicz et al., Jan. 30, 2014. 456 pages.
Genbank Submission; NIH/NCBI Accession No. CP002815.1. Hunyadkurti et al., Jan. 30, 2014. 482 pages.
Genbank Submission; NIH/NCBI Accession No. CP003084.1. Horvath et al., Jan. 30, 2014. 440 pages.
Genbank Submission; NIH/NCBI Accession No. CP003195.1. Voros et al., Jan. 30, 2014. 463 pages.
Genbank Submission; NIH/NCBI Accession No. CP003196.1. Voros et al., Jan. 30, 2014. 469 pages.
Genbank Submission; NIH/NCBI Accession No. CP003197.1. Voros et al., Jan. 30, 2014. 465 pages.
Genbank Submission; NIH/NCBI Accession No. CP003293.1. Fitz-Gibbon et al., Jan. 31, 2014. 415 pages.
Genbank Submission; NIH/NCBI Accession No. CP003877.1. Minegishi et al., Jan. 31, 2014. 481 pages.
Genbank Submission; NIH/NCBI Accession No. CP006032.1. Nagy et al., Oct. 1, 2014. 542 pages.

(56) References Cited

OTHER PUBLICATIONS

Genbank Submission; NIH/NCBI Accession No. CP012350.1. Scholz et al., Sep. 22, 2017. 556 pages.
Genbank Submission; NIH/NCBI Accession No. CP012351.1. Scholz et al., Sep. 22, 2017. 560 pages.
Genbank Submission; NIH/NCBI Accession No. CP012352.1. Scholz et al., Sep. 22, 2017. 562 pages.
Genbank Submission; NIH/NCBI Accession No. CP012353.1. Scholz et al., Sep. 22, 2017. 548 pages.
Genbank Submission; NIH/NCBI Accession No. CP012354.1. Scholz et al., Sep. 22, 2017. 553 pages.
Genbank Submission; NIH/NCBI Accession No. CP012355.1. Scholz et al., Sep. 22, 2017. 554 pages.
Genbank Submission; NIH/NCBI Accession No. CP012647.1. Kook et al., Oct. 11, 2017. 546 pages.
Genbank Submission; NIH/NCBI Accession No. CP013693.1. Alexeeva et al., Oct. 17, 2017. 520 pages.
Genbank Submission; NIH/NCBI Accession No. CP023676.1. Tang et al., Apr. 2, 2018. 588 pages.
Genbank Submission; NIH/NCBI Accession No. CP031442.1. Kook et al., Aug. 14, 2018. 606 pages.
Genbank Submission; NIH/NCBI Accession No. JN051668.1. Lood et al., Jun. 30, 2012. 1 page.
Genbank Submission; NIH/NCBI Accession No. NC_006085.1. Bruggemann et al., Mar. 29, 2017. 1 page.
Genbank Submission; NIH/NCBI Accession No. NC_014039.1. Harkins et al., Mar. 30, 2017. 2 pages.
Genbank Submission; NIH/NCBI Accession No. NC_016511.1. Voros et al., Jan. 11, 2018. 1 page.
Genbank Submission; NIH/NCBI Accession No. NC_016512.1. Voros et al., Jan. 11, 2018. 1 page.
Genbank Submission; NIH/NCBI Accession No. NC_016516.1. Voros et al., Jan. 11, 2018. 1 page.
Genbank Submission; NIH/NCBI Accession No. NC_017534.1. Brzuszkiewicz et al., Mar. 30, 2017. 2 pages.
Genbank Submission; NIH/NCBI Accession No. NC_017535.1. Hunyadkurti et al., Mar. 30, 2017. 1 page.
Genbank Submission; NIH/NCBI Accession No. NC_017550.1. Horvath et al., Jan. 11, 2018. 2 pages.
Genbank Submission; NIH/NCBI Accession No. NC_018707.1. Minegishi et al., Mar. 30, 2017. 1 page.
Genbank Submission; NIH/NCBI Accession No. NC_021085.1. Fitz-Gibbon et al., Apr. 1, 2017. 1 page.
Genbank Submission; NIH/NCBI Accession No. NZ_CP006032.1. Nagy et al., Apr. 2, 2017. 2 pages.
Genbank Submission; NIH/NCBI Accession No. NZ_CP012350.1. Scholz et al., Sep. 25, 2017. 2 pages.
Genbank Submission; NIH/NCBI Accession No. NZ_CP012351.1. Scholz et al., Sep. 25, 2017. 2 pages.
Genbank Submission; NIH/NCBI Accession No. NZ_CP012352.1. Scholz et al., Sep. 25, 2017. 2 pages.
Genbank Submission; NIH/NCBI Accession No. NZ_CP012353.1. Scholz et al., Sep. 25, 2017. 2 pages.
Genbank Submission; NIH/NCBI Accession No. NZ_CP012354.1. Scholz et al., Sep. 25, 2017. 2 pages.
Genbank Submission; NIH/NCBI Accession No. NZ_CP012355.1. Scholz et al., Sep. 25, 2017. 2 pages.
Genbank Submission; NIH/NCBI Accession No. NZ_CP012647.1. Kook et al., Oct. 18, 2017. 2 pages.
Genbank Submission; NIH/NCBI Accession No. NZ_CP013693.1. Alexeeva et al., Oct. 23, 2017. 2 pages.
Genbank Submission; NIH/NCBI Accession No. NZ_CP023676.1. Tang et al., Apr. 4, 2018. 2 pages.
Genbank Submission; NIH/NCBI Accession No. NZ_CP031442.1. Kook et al., Aug. 16, 2018. 2 pages.
Guell et al., Long lasting effect of skin microbiome modulation induced by probiotic solution application. Presented at Barcelona Debates on Human Microbiome, Jun. 30-Jul. 1, 2016. 1pg. Poster.
Gutteridge et al., The deoxyribose assay: an assay both for 'free' hydroxyl radical and for site-specific hydroxyl radical production. Biochem J. Aug. 1, 1988;253(3):932-3. doi: 10.1042/bj2530932.
Holland et al., Proteomic identification of secreted proteins of Propionibacterium acnes. BMC Microbiol. Aug. 27, 2010;10:230. doi: 10.1186/1471-2180-10-230.
Holmberg et al., Biofilm formation by Propionibacterium acnes is a characteristic of invasive isolates. Clin Microbiol Infect. Aug. 2009;15(8):787-95. doi: 10.1111/j.1469-0691.2009.02747.x. Epub Apr. 23, 2009.
Johnson et al., Cell wall composition and deoxyribonucleic acid similarities among the anaerobic coryneforms, classical propionibacteria, and strains of Arachnia propionica. J Bacteriol. Mar. 1972;109(3):1047-66. doi: 10.1128/jb.109.3.1047-1066.1972.
Kadam et al. Role of oxidative stress in various stages of psoriasis. Indian J Clin Biochem. Oct. 2010;25(4):388-92. doi: 10.1007/s12291-010-0043-9. Epub Sep. 24, 2010.
Karoglan et al. Segmental angeordnete basaloide follikuläre Hamartome mit zerebralen Eisenablagerungen als neue Variante des Happle-Tinschert Syndroms. Journal of the German Society of Dermatology. Apr. 25, 2017; 15(S1): #P094. doi.org/10.1111/ddg.13213. Abstract only.
Karoglan et al., Direct modulation of the skin microbiome as new experimental tool for skin diseases. 44th Annual Meeting of the ADF in Gottingen, Germany, Mar. 8, 2017. 1pg. Abstract only.
Karoglan et al., Direct modulation of the skin microbiome as new experimental tool for skin diseases. 44th Annual Meeting of the ADF in Gottingen, Germany, Mar. 9-11, 2017. 1pg. Poster.
Lin et al., A combination of improved differential and global RNA-seq reveals pervasive transcription initiation and events in all stages of the life-cycle of functional RNAs in Propionibacterium acnes, a major contributor to wide-spread human disease. BMC Genomics. Sep. 14, 2013;14:620. doi: 10.1186/1471-2164-14-620.
Lodes et al., Variable expression of immunoreactive surface proteins of Propionibacterium acnes. Microbiology (Reading). Dec. 2006;152(Pt 12):3667-3681. doi: 10.1099/mic.0.29219-0.
Lomholt et al., Population genetic analysis of Propionibacterium acnes identifies a subpopulation and epidemic clones associated with acne. PLoS One. Aug. 19, 2010;5(8):e12277. doi: 10.1371/journal.pone.0012277.
Mcdowell et al., A new phylogenetic group of Propionibacterium acnes. J Med Microbiol. Feb. 2008;57(Pt 2):218-224. doi: 10.1099/jmm.0.47489-0.
Mcdowell et al., An expanded multilocus sequence typing scheme for propionibacterium acnes: investigation of 'pathogenic', 'commensal' and antibiotic resistant strains. PLoS One. 2012;7(7):e41480. doi: 10.1371/journal.pone.0041480. Epub Jul. 30, 2012.
Mcdowell et al., Propionibacterium acnes types I and II represent phylogenetically distinct groups. J Clin Microbiol. Jan. 2005;43(1):326-34. doi: 10.1128/JCM.43.1.326-334.2005. Erratum in: J Clin Microbiol. Feb. 2010;48(2):681.
Nicholson et al., Identification and inhibition of the ICE/CED-3 protease necessary for mammalian apoptosis. Nature. Jul. 6, 1995;376(6535):37-43. doi: 10.1038/376037a0.
Patzold, Long lasting effect of skin microbiome modulation induced by topical probiotic solution application. Barcelona Debates on Human Microbiome, Jul. 1, 2016. 15 pgs. Presentation.
Patzold, Long lasting effect of skin microbiome modulation induced by topical probiotic solution application. Targeting Microbiota, Paris, France. Oct. 17, 2016. 13 pgs. Presentation.
Sander et al., Oxidative stress in malignant melanoma and non-melanoma skin cancer. Br J Dermatol. May 2003;148(5):913-22. doi: 10.1046/j.1365-2133.2003.05303.x.
Scholz et al., A novel high-resolution single locus sequence typing scheme for mixed populations of Propionibacterium acnes in vivo. PLoS One. Aug. 11, 2014;9(8):e104199. doi: 10.1371/journal.pone.0104199. eCollection 2014.
Solovyev at al., Automatic Annotation of Microbial Genomes and Metagenomic Sequences. In Metagenomics and its Applications in Agriculture, Biomedicine and Environmental Studies. 2011 Li (Ed). 19 pages.

(56) References Cited

OTHER PUBLICATIONS

Valanne et al., CAMP factor homologues in Propionibacterium acnes: a new protein family differentially expressed by types I and II. Microbiology (Reading). May 2005;151(Pt 5):1369-1379. doi: 10.1099/mic.0.27788-0.
Valavanidis et al., 8-hydroxy-2'-deoxyguanosine (8-OHdG): A critical biomarker of oxidative stress and carcinogenesis. J Environ Sci Health C Environ Carcinog Ecotoxicol Rev. Apr. 2009;27(2):120-39. doi: 10.1080/10590500902885684.

\* cited by examiner

| Scale / Count of Subjects | 1 | 2 | 3 | 4 | 5 | 6 | 7 | 8 | 9 | 10 |
|---|---|---|---|---|---|---|---|---|---|---|
| V1 (D1) | | | | 5 | 6 | 2 | 1 | | | |
| V2 (D7) | | | | 1 | 6 | 5 | 2 | | | |
| V3 (D21) | | | 1 | | 2 | 2 | 6 | 3 | | |
| V4 (D42) | | | | | 4 | 2 | 5 | 1 | 2 | |

SEQUENCE LISTING

<160> NUMBER OF SEQ ID NOS: 82

<210> SEQ ID NO 1
<211> LENGTH: 484
<212> TYPE: DNA
<213> ORGANISM: Propionibacterium acnes

<400> SEQUENCE: 1

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
```

```
ctgtcatcac gaaggccacc acaatctatc ccagaacagc cggcacttca ctcacgatgc    300
cccgatgctg gattcctatt gtcgcccttg ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacataccca ttacatcagc    480
atag                                                                  484
```

<210> SEQ ID NO 2
<211> LENGTH: 484
<212> TYPE: DNA
<213> ORGANISM: Propionibacterium acnes

<400> SEQUENCE: 2

```
gttgcacacc aggggtcaa cttggcgtcc tcagttcaaa attgattcaa actaacagtt     60
ccatgtcggg aaacagcacc aggaagctcg tgacatatcg tctttcattg cgagaaacat    120
cttacttatg tacatttcta agctatagcg tctaccctttg tcagacccag gacgatgggt   180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgattctg gattcctatt gtcgcccttg ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacataccca ttacatcagc    480
atag                                                                  484
```

<210> SEQ ID NO 3
<211> LENGTH: 484
<212> TYPE: DNA
<213> ORGANISM: Propionibacterium acnes

<400> SEQUENCE: 3

```
gttgcacacc aggggtcaa cttggcgtcc tcagttcaaa attgattcaa actaacagtt     60
ccatgtcggg aaacagcacc aggaagctcg tgacatatgg tctttcattg cgagaaacat    120
cttacttatg tacatttcta agctatagcg tctaccctttg tcagacccag gacgatgggt   180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttg ttagggcaag cggtgccagt agcagaatat    360
gtcacctcaa taactcgatc caccctgcc cattacatgg gtaacatatc catggaggtt    420
cgatgtatac tcgaggatac agtcgtccat cacgcccgcc tacataccca ttacatcagc    480
atag                                                                  484
```

<210> SEQ ID NO 4
<211> LENGTH: 484
<212> TYPE: DNA
<213> ORGANISM: Propionibacterium acnes

<400> SEQUENCE: 4

```
gttgcacacc aggggtcaa cttggcgtcc tcagttcaaa attgattcaa actaacagtt     60
ccatgtcggg aaacagcacc aggaagctcg tgacatatgg tctttcattg cgagaaacat    120
cttacttatg tacatttcta agctatagcg tctaccctttg tcagacccag gacgatgggt   180
gtcacatctc ctttctagtc aacctaagag aggaggaaat gccgcgatat atgttccacc    240
```

```
ctgtcatcac gaaggccacc acaatctatc ccagaacagc cggcacttca ctcacgatgc    300
cccgatgctg gattcctatt gtcgcccttaa ttagggcaag cggtgccagt agcagaatat   360
gtcacctcaa caactcgatc caccccctgcc cattacatgg gtaacatatc catggaggtt   420
cgatgtatac tcgaggatac agtcgtccat cacgcccgcc tacatacccaa ttacatcagc   480 atag                                                                 484
```

<210> SEQ ID NO 5
<211> LENGTH: 484
<212> TYPE: DNA
<213> ORGANISM: Propionibacterium acnes

<400> SEQUENCE: 5

```
gttgcacacc aggggtcaa cttggcgtcc tcagttcaaa attgattcaa actaacagtt     60
ccatgccggg aaacagcacc aggaagctcg tgacatatcg tctttcattg cgagaaacat   120
cttacttatg tacatttcta agctatagcg tctaccccttg tcagacccag gacgatgggt   180
gtcacatctc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgccctta ttagggcaag cggtgccagt agcagaatat   360
gtcacctcaa caactcgatc caccccctgcc cattacatgg gtaacatatc catggaggtt   420
cgatgtatac tcgaggatac agtcgtccat cacgcccgcc tacatacccaa ttacatcagc   480 atag                                                                 484
```

<210> SEQ ID NO 6
<211> LENGTH: 484
<212> TYPE: DNA
<213> ORGANISM: Propionibacterium acnes

<400> SEQUENCE: 6

```
gttgcacacc aggggtcaa cttggcgtcc tcagttcaaa attgattcaa actaacagtt     60
ccatgtcggg aaacagcacc aggaagctcg tgacatatcg tctttcattg cgagaaacat   120
cttacttatg tacatttcta agctatagcg tctaccccttg tcagacccag gacgatgggt   180
gtcacatctc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgccctta ttagggcaag cggtgccagt agcagaatat   360
gtcacctcaa caactcgatc caccccctgcc cattacatgg gtaacatatc catggaggtt   420
cgatgtatac tcgaggatac agtcgtccat cacgcccgcc tacatacccaa ttacatcagc   480 atat                                                                 484
```

<210> SEQ ID NO 7
<211> LENGTH: 484
<212> TYPE: DNA
<213> ORGANISM: Propionibacterium acnes

<400> SEQUENCE: 7

```
gttgcacacc aggggtcaa cttggcgtcc tcagttcaaa attgattcaa actaacagtt     60
ccatgtcggg aaacagcacc aggaagctcg tgacatatcg tctttcattg cgagaaacat   120
cttacttatg tacatttcta agctatagcg tctaccccttg tcagacccag gacgatgggt   180
gtcacatctc ctttctagtc aacctaagag aggaggaaat gccgcgatat atgttccacc   240
ctgccatcac gaaggccacc acaatctatc ccagaacagc cggcacttca ctcacgatgc   300
```

```
cccgattctg gattcctatt gtcgcccttt ttagggcaag cggtgccagt agcagaatat      360
gtcacctcaa caactcgatc cacccctgcc cattacatgg gtaacatatc catggaggtt      420
cgatgtatac tcgaggatac agtcgtccat cacgcccgcc tacatacccg ttacatcagc      480
atag                                                                  484

<210> SEQ ID NO 8
<211> LENGTH: 484
<212> TYPE: DNA
<213> ORGANISM: Propionibacterium acnes

<400> SEQUENCE: 8
gttgcacacc aggggggtcaa cttggcgtcc tcagttcaaa attgattcaa actaacagtt      60
ccatgtcggg aaacagcacc aggaagctcg tgacatatcg cctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacgatgc      300
cccgatgctg gattcctatt gtcgcccttt ttagggcaag cggtgccagt agcagaatat      360
gtcacctcaa caactcgatc caccccttgcc cattacatgg gtaacatatc catggaggtt      420
cgatgtatac tcgaggatac agtcgtccat cacgcccgcc tacatacccg ttacatcagc      480
atag                                                                  484

<210> SEQ ID NO 9
<211> LENGTH: 484
<212> TYPE: DNA
<213> ORGANISM: Propionibacterium acnes

<400> SEQUENCE: 9
gttgcacacc aggggggtcaa cttggcgtcc tcagttcaaa attgattcaa actaacagtt      60
ccatgccggg aaacagcacc aggaagctcg tgacatatcg tctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcat gaaggccacc acaatctatc ccagaacagc cggcacttca ctcacgatgc      300
cccgatgctg gattcctatt gtcgcccttt ttagggcaag cggtgccagt agcagaatat      360
gtcacctcaa caactcgatc caccccttgcc cattacatgg gtaacatatc catggaggtt      420
cgatgtatac tcgaggatac agtcgtccat cacgcccgcc tacatacccg ttacatcagc      480
atag                                                                  484

<210> SEQ ID NO 10
<211> LENGTH: 484
<212> TYPE: DNA
<213> ORGANISM: Propionibacterium acnes

<400> SEQUENCE: 10
gttgcacacc aggggggtcaa cttggcgtcc tcagttcaaa attgattcaa actaacagtt      60
ccatgccggg aaacagcacc aggaagctcg tgacatatcg tctttcattg cgagaaacat      120
cttacttatg tacatttcta agctatagcg tctacccttg tcagacccag gacgatgggt      180
gtcacatctc ctttctagtc aacctaagag aggaggaaat gccgcgatat atgttccacc      240
ctgtcatcac gaaggccacc acaatctatc ccagaacagc cggcacttca ctcacgatgc      300
```

```
cccgatgctg gattcctatt gtcgcccttg ttagggcaag cggtgccagt agcagaatat    360
gtcacctcaa caactcgatc taccccctgcc cattacatgg gtaacatatc catggaggtt    420
cgatgtatac tcgaggatac agtcgtccat cacgcccgcc tacatacccca ttacatcagc    480 atag                                                                  484

<210> SEQ ID NO 11
<211> LENGTH: 484
<212> TYPE: DNA
<213> ORGANISM: Propionibacterium acnes

<400> SEQUENCE: 11
gttgcacacc aggggtcaa cttggcgtcc tcagttcaaa attgattcaa actaacagtt      60
ccatgccggg aaacagcacc aggaagcccg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttg ttagggcaag cggtgccagt agcagaatat    360
gtcacctcaa caactcgatc caccccctgcc cattacatgg gtaacatatc catggaggtt    420
cgatgtatac tcgaggatac agtcgtccat cacgcccgcc tacatacccca ttacatcagc    480 atag                                                                  484

<210> SEQ ID NO 12
<211> LENGTH: 484
<212> TYPE: DNA
<213> ORGANISM: Propionibacterium acnes

<400> SEQUENCE: 12
gttgcacacc aggggtcaa cttggcgtcc tcagttcaaa attgattcaa actaacagtt      60
ccatgccggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atattccacc    240
ctgtcatcac gaaggccacc acaatctatc ccagaacagc cggcacttca ctcacgatgc    300
cccgatgctg gattcctatt gtcgcccttg ttagggcaag cggtgccagt agcagaatat    360
gtcacctcaa caactcgatc caccccctgcc cattacatgg gtaacatatc catggaggtt    420
cgatgtatac tcgaggatac agtcgtccat cacgcccgcc tacatacccca ttacatcagc    480 atag                                                                  484

<210> SEQ ID NO 13
<211> LENGTH: 484
<212> TYPE: DNA
<213> ORGANISM: Propionibacterium acnes

<400> SEQUENCE: 13
gttgcacacc aggggtcaa cttggcgtcc tcagttcaaa attgattcaa actaacagtt      60
ccatgtcggg aaacagcacc aggaagctgg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgcccttg ttagggcaag cggtgccagt agcagaatat    360
```

```
gtcacctcaa caactcgatc cacccctgcc cattacatgg gtaacatatc catggaggtt      420
cgatgtatac tcgaggatac agtcgtccat cacgcccgcc tacatacccc ttacatcagc      480
atag                                                                  484
```

<210> SEQ ID NO 14
<211> LENGTH: 484
<212> TYPE: DNA
<213> ORGANISM: Propionibacterium acnes

<400> SEQUENCE: 14

```
gttgcacacc aggggtcaa cttggcgttt tcagttcaaa attgattcaa actaacagtt       60
ccatgccggg aaacagcacc aggaagctcg tgacatatcg tctttcattg cgagaaacat     120
cttacttatg tacatttcta agctatagcg tctaccccttg tcagacccag gacgatgggt    180
gtcacatctc ctttctagtc aacctaagag aggaggaaat gccgcgatat atgttccacc    240
ctgtcatcac gaaggccacc acaatctatc cagaacagc cggcacttca ctcacgatgc     300
cccgatgctg gattcctatt gtcgccccta ttagggcaag cggtgccagt agcagaatat    360
gtcacctcaa caactcgatc caccccctgcc cattacatgg gtaacatatc catggaggtt   420
cgatgtatac tcgaggatac agtcgtccat cacgcccgcc tacatacccc ttacatcagc    480
atag                                                                  484
```

<210> SEQ ID NO 15
<211> LENGTH: 484
<212> TYPE: DNA
<213> ORGANISM: Propionibacterium acnes

<400> SEQUENCE: 15

```
gttgcacacc aggggtcaa cttggcgtcc tcagttcaaa attgattcaa actaacagtt       60
ccatgccggg aaacagtacc aggaagctcg tgacatatcg tctttcattg cgagaaacat     120
cttacttatg tacatttcta agctatagcg tctaccccttg tcagacccag gacgatgggt    180
gtcacatctc ctttctagtc aacctaagag aggaggaaat gccgcgatat atgttccacc    240
ctgtcatcac gaaggccacc acaatctatc cagaacagc cggcacttca ctcacgatgc     300
cccgatgctg gattcctatt gtcgccccta ttagggcaag cggtgccagt agcagaatat    360
gtcacctcaa caactcgatc caccccctgcc cattacatgg gtaacatatc catggaggtt   420
cgatgtatac tcgaggatac agtcgtccat cacgcccgcc tacatacccc ttacatcagc    480
atag                                                                  484
```

<210> SEQ ID NO 16
<211> LENGTH: 484
<212> TYPE: DNA
<213> ORGANISM: Propionibacterium acnes

<400> SEQUENCE: 16

```
gttgcacacc aggggtcaa cttggcgtcc tcagttcaaa attgattcaa actaacagtt       60
ccatgccggg aaacagcacc aggaagctcg tgacatatcg tctttcattg cgagaaacat     120
cttacttatg tacatttcta agctatagcg tctaccccttg tcagacccag gacgatgggt    180
gtcacatctc ctttctagtc aacctaagag aggaggaaat gccgcgatat atgttccacc    240
ctgtcatcac gaaggccacc acaatctatc cagaacagc cggcacttca ctcacgatgc     300
cccgatgctg gatccctatt gtcgccccta ttagggcaag cggtgccagt agcagaatat    360
```

```
gtcacctcaa caactcgatc caccoctgcc cattacatgg gtaacatatc catggaggtt    420
cgatgtatac tcgaggatac agtcgtccat cacgcccgcc tacataccca ttacatcagc    480
atag                                                                 484

<210> SEQ ID NO 17
<211> LENGTH: 484
<212> TYPE: DNA
<213> ORGANISM: Propionibacterium acnes

<400> SEQUENCE: 17
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccottg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccggt agcagaatat    360
gtcacctcaa caactcgatc caccoctgcc cattacatgg gtaacatatc catggaggtt    420
cgatgtatac tcgaggatac agtcgtccat cacgcccgcc tacataccca ttacatcagc    480
atag                                                                 484

<210> SEQ ID NO 18
<211> LENGTH: 484
<212> TYPE: DNA
<213> ORGANISM: Propionibacterium acnes

<400> SEQUENCE: 18
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccottg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gccacctcaa caactcgatc caccoctgcc cattacatgg gtaacatatc catggaggtt    420
cgatgtatac tcgaggatac agtcgtccat cacgcccgcc tacataccca ttacatcagc    480
atag                                                                 484

<210> SEQ ID NO 19
<211> LENGTH: 484
<212> TYPE: DNA
<213> ORGANISM: Propionibacterium acnes

<400> SEQUENCE: 19
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctaccottg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc gaccoctgcc cattacatgg gtaacatatc catggaggtt    420
```

```
cgatgtatac tcgaggatac agtcgtccat cacgcccgcc tacatacccca ttacatcagc    480 atag                                                                  484

<210> SEQ ID NO 20
<211> LENGTH: 484
<212> TYPE: DNA
<213> ORGANISM: Propionibacterium acnes

<400> SEQUENCE: 20
gttgcacacc aggggggtcaa cttggcgtcc tcagttcaaa attgattcaa actaacagtt    60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt ttcgccctta ttagggcaag cggtgccagt agcagaatat    360
gtcacctcaa caactcgatc caccccctgcc cattacatgg gtaacatatc catggaggtt    420
cgatgtatac tcgaggatac agtcgtccat cacgcccgcc tacatacccca ttacatcagc    480 atag                                                                  484

<210> SEQ ID NO 21
<211> LENGTH: 484
<212> TYPE: DNA
<213> ORGANISM: Propionibacterium acnes

<400> SEQUENCE: 21
gttgcacacc aggggggtcaa cttggcgtcc tcagttcaaa attgattcaa actaacagtt    60
ccatgccggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctagtc aacctaagag aggaggaaat gccgcgatat atgttccacc    240
ctgtcatcac gaaggccacc acaatctatc ccagaacagc cggcacttca ctcacaatgc    300
cccgatgctg gattcctatt gtcgccctta ttagggcaag cggtgccagt agcagaatat    360
gtcacctcaa caactcgatc caccccctgcc cattacatgg gtaacatatc catggaggtt    420
cgatgtatac tcgaggatac agtcgtccat cacgcccgcc tacatacccca ttacatcagc    480 atag                                                                  484

<210> SEQ ID NO 22
<211> LENGTH: 484
<212> TYPE: DNA
<213> ORGANISM: Propionibacterium acnes

<400> SEQUENCE: 22
gttgcacacc aggggggtcaa cttggcgtcc tcagttcaaa attgattcaa actaacagtt    60
ccatgccggg aaacagcacc aggaagctcg tgacatatcg tctttcattg cgagaaacat    120
cttacttatg tacatttcta agctatagcg tctacccttg tcagacccag gacgatgggt    180
gtcacatctc ctttctggtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccccctgcc cattacatgg gtaacatatc catggaggtt    420
```

| | |
|---|---:|
| cgatgtatac tcgaggatac agtcgtccat cacgcccgcc tacatacccca ttacatcagc | 480 |
| atag | 484 |

<210> SEQ ID NO 23
<211> LENGTH: 484
<212> TYPE: DNA
<213> ORGANISM: Propionibacterium acnes

<400> SEQUENCE: 23

| | |
|---|---:|
| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatctc ctttctagtc aacccaagag aggaggaaat gccgcgatat atgttccacc | 240 |
| ctgtcatcac gaaggccacc acaatctatc ccagaacagc cggcacttca ctcacgatgc | 300 |
| cccgattctg gattcctatt gtcgcccttta ttagggcaag cggtgccagt agcagaatat | 360 |
| gtcacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 24
<211> LENGTH: 484
<212> TYPE: DNA
<213> ORGANISM: Propionibacterium acnes

<400> SEQUENCE: 24

| | |
|---|---:|
| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatccc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgcccttta ttagggcaag cggtgccagt agcagaatat | 360 |
| gtcacctcag caactcgatc caccccctgcc cattacatgg gtaacatatc catggaggtt | 420 |
| cgatgtatac tcgaggatac agtcgtccat cacgcccgcc tacatacccca ttacatcagc | 480 |
| atag | 484 |

<210> SEQ ID NO 25
<211> LENGTH: 484
<212> TYPE: DNA
<213> ORGANISM: Propionibacterium acnes

<400> SEQUENCE: 25

| | |
|---|---:|
| gttgcacacc aggggtcaa cttggcgtcc tcagttcaaa attgattcaa actaacagtt | 60 |
| ccatgtcggg aaacagcacc aggaagctcg tgacatatcg tctttcattg cgagaaacat | 120 |
| cttacttatg tacatttcta agctatagcg tctacccttg tcagacccag gacgatgggt | 180 |
| gtcacatccc ctttctagtc aacctaagag aggaggaaat gccgcgatat atgttccacc | 240 |
| ctgtcatcac gaaggccacc acaatctatc ccagaacagc cggcacttca ctcacgatgc | 300 |
| cccgatgctg gattcctatt gtcgcccttta ttagggcaag cggtgccagt agcagaatat | 360 |
| gtcacctcaa caactcgatc caccccctgcc cattacatgg gtaacatatc catggaggtt | 420 |
| cgatgtatac tcgaggatac agtcgtccat cacgcccgcc tacatacccca ttacatcagc | 480 |

```
atag                                                                   484

<210> SEQ ID NO 26
<211> LENGTH: 484
<212> TYPE: DNA
<213> ORGANISM: Propionibacterium acnes

<400> SEQUENCE: 26
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagaccat gacgatgggt     180 gtcacatccc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgcccctta ttagggcaag cggtgccagt agcagaatat  360
gtcacctcaa caactcgatc caccccctgcc cattacatgg gtaacatatc catggaggtt  420
cgatgtatac tcgaggatac agtcgtccat cacgcccgcc tacatacccca ttacatcagc 480 atag                                                                 484

<210> SEQ ID NO 27
<211> LENGTH: 484
<212> TYPE: DNA
<213> ORGANISM: Propionibacterium acnes

<400> SEQUENCE: 27
gttgcacacc aggggtcaa cttggcgtcc ttagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgcccctta ttagggcaag cggtgccagt agcagaatat  360
gtcacctcaa caactcgatc caccccctgcc cattacatgg gtaacatatc catggaggtt  420
cgatgtatac tcgaggatac agtcgtccat cacgcccgcc tacatacccca ttacatcagc 480 atag                                                                 484

<210> SEQ ID NO 28
<211> LENGTH: 484
<212> TYPE: DNA
<213> ORGANISM: Propionibacterium acnes

<400> SEQUENCE: 28
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatgggt    180
gtcacatccc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgcccctta ttagggcaag cggtgccagt agcagaatat  360
gtcacctcaa caactcgatc caccccctgcc cattacatgg gtaacatatc catggaggtt  420
cgatgtatac tcgaggatac agtcgtccat cacgcccgcc tacatacccca ttacatctgc 480
```

```
atag                                                               484

<210> SEQ ID NO 29
<211> LENGTH: 484
<212> TYPE: DNA
<213> ORGANISM: Propionibacterium acnes

<400> SEQUENCE: 29
gttgcacacc aggggggtcaa cttggcgtcc tcagttcaaa attgattcaa actaacagtt    60
ccatgtcggg aaacagcacc aggaaactcg tgacatatcg tctttcattg cgagaaacat   120
cttacttatg tacatttcta agctatagcg tctacccttg tcagacccag gacgatgggt   180
gtcacatccc ctttctagtc aacctaagag aggaggaaat gccgcgatat atgttccgcc   240
ctgtcatcac gaagaccacc acaatctatc cagaacagc cggcacttca ctcacgatgc    300
cccgatgctg gattcctatt gtcgcccctta ttagggcaag cggtgccagt agcagaatat   360
gtcacctcaa caactcgatc caccccctgcc cattacatgg gtaacatatc catggaggtt   420
cgatgtatac ttgaggatac agtcgtccat cacgcccacc tacatacca ttacatcagc    480 atag                                                               484

<210> SEQ ID NO 30
<211> LENGTH: 484
<212> TYPE: DNA
<213> ORGANISM: Propionibacterium acnes

<400> SEQUENCE: 30
gttgcacacc aggggggtcaa cttggcgtcc tcagttcaaa attgattcaa actaacagtt    60
ccatgtcggg aaacagcacc aggaaactcg tgacatatcg tctttcattg cgagaaacat   120
cttacttatg tacatttcta agctatagcg tctacccttg tcagacccag gacgatgggt   180
gtcacatccc ctttctagtc aacctaagag aggaggaaac gccgcgatat atgttccgcc   240
ctgtcatcac gaagaccacc acaatctatc cagaacagc cggcacttca ctcacgatgc    300
cccgatgctg gattcctatt gtcgcccctta ttagggcaag cggtgccagt agcagaatat   360
gtcacctcaa caactcgatc caccccctgcc cattacatgg gtaacatatc catggaggtt   420
cgatgtatac ttgaggatac agtcgtccat cacgcccacc tacatacca ttacatcagc    480 atag                                                               484

<210> SEQ ID NO 31
<211> LENGTH: 484
<212> TYPE: DNA
<213> ORGANISM: Propionibacterium acnes

<400> SEQUENCE: 31
gttgcacacc aggggggtcaa cttggcgtcc tcagttcaaa attgattcaa actaacagtt    60
ccatgtcggg aaacagcacc aggaaactcg tgacatatcg tctttcattg cgagaaacat   120
cttacttatg tacatttcta agctatagcg tctacctttg tcagacccag gacgatgggt   180
gtcacatccc ctttctagtc aacctaagag aggaggaaat gccgcgatat atgttccgcc   240
ctgtcatcac gaagaccacc acaatctatc cagaacagc cggcacttca ctcacgatgc    300
cccgatgctg gattcctatt gtcgcccctta ttagggcaag cggtgccagt agcagaatat   360
gtcacctcaa caactcgatc caccccctgcc cattacatgg gtaacatatc catggaggtt   420
cgatgtatac ttgaggatac agtcgtccat cacgcccacc tacatacca ttacatcagc    480 atag                                                               484
```

<210> SEQ ID NO 32
<211> LENGTH: 484
<212> TYPE: DNA
<213> ORGANISM: Propionibacterium acnes

<400> SEQUENCE: 32

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatat tcgagaatac agtcgtccat cacgcccgcc tacatacca ttacatcagc    480
atag                                                                 484
```

<210> SEQ ID NO 33
<211> LENGTH: 484
<212> TYPE: DNA
<213> ORGANISM: Propionibacterium acnes

<400> SEQUENCE: 33

```
gttgcacacc aggggtcaa cttggcgtcc tcagttcaaa attgatttaa actaacagtt      60
ccatgtcggg aaacagcacc agaaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatat tcgaggatac agtcgtccat cacgcccgcc tacatacca ttacatcagc    480
atag                                                                 484
```

<210> SEQ ID NO 34
<211> LENGTH: 484
<212> TYPE: DNA
<213> ORGANISM: Propionibacterium acnes

<400> SEQUENCE: 34

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgcccta ttagggcaag cggtgccagt agcagaatat    360
gtcacctcaa caactcgatc caccctgcc cattacatgg gtaacatatc catggaggtt    420
cgatgtatat tcgaggatac agtcgtccat cacgcccgcc tacatacca ttacatcagc    480
atag                                                                 484
```

<210> SEQ ID NO 35
<211> LENGTH: 484
<212> TYPE: DNA
<213> ORGANISM: Propionibacterium acnes

<400> SEQUENCE: 35

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgcccttt attagggcaag cggtgccagt agcagaatat    360
gtcacctcaa caactcgatc caccccctgcc cattacatgg gtaacatatc catgaaggtt    420
cgatgtatat tcgaggatac agtcgtccat cacgcccgcc tacataccca ttacatcagc    480
atag                                                                 484
```

<210> SEQ ID NO 36
<211> LENGTH: 484
<212> TYPE: DNA
<213> ORGANISM: Propionibacterium acnes

<400> SEQUENCE: 36

```
gttgcacacc aggggtcaa cttggcgtcc tcagttcaaa attgatttaa actaacagtt      60
tcatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatat tcgaggatac agtcgtccat cacgcccgcc tacataccca ttacatcagc    480
atag                                                                 484
```

<210> SEQ ID NO 37
<211> LENGTH: 484
<212> TYPE: DNA
<213> ORGANISM: Propionibacterium acnes

<400> SEQUENCE: 37

```
gttgcacacc aggggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat tccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatat tcgaggatac agtcgtccat cacgcccgcc tacataccca ttacatcagc    480
atag                                                                 484
```

<210> SEQ ID NO 38
<211> LENGTH: 484
<212> TYPE: DNA
<213> ORGANISM: Propionibacterium acnes

<400> SEQUENCE: 38

```
gttgcacacc agagggtcaa cttggcgtcc tcagttcaaa attgatttaa actaacagtt      60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatat tcgaggatac agtcgtccat cacgcccgcc tacataccca ttacatcagc    480
atag                                                                 484
```

<210> SEQ ID NO 39
<211> LENGTH: 484
<212> TYPE: DNA
<213> ORGANISM: Propionibacterium acnes

<400> SEQUENCE: 39

```
gttgcacacc aggggtcaa cttggcgtcc tcagttcaaa attgatttaa actaacagtt       60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcgcctca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatat tcgaggatac agtcgtccat cacgcccgcc tacataccca ttacatcagc    480
atag                                                                 484
```

<210> SEQ ID NO 40
<211> LENGTH: 484
<212> TYPE: DNA
<213> ORGANISM: Propionibacterium acnes

<400> SEQUENCE: 40

```
gttgcacacc aggggtcaa cttggcgtcc tcagttcaaa atagatttaa actaacagtt       60
ccatgtcggg aaacagcacc aggaagctcg tgacatatcg tctttcattg cgagaaacat    120
cttacttatg tacatttcta agctatagcg tctacccttg tcagacccag gacgatggat    180
gtcacatccc ctttctagtc aacctaagag aggaggaaat gccgcgatat atgttccacc    240
ctgtcatcac gaaggccacc acaatctatc ccagaacagc cggcacctca ctcacgatgc    300
cccgatgctg gattcctatt gtcgccctta ttagggcaag cggtgccagt agcagaatat    360
gtcacctcaa caactcgatc cacccctgcc cattacatgg gtaacatatc catggaggtt    420
cgatgtatat tcgaggatac agtcgtccat cacgcccgcc tacataccca ttacatcagc    480
atag                                                                 484
```

<210> SEQ ID NO 41

<211> LENGTH: 484
<212> TYPE: DNA
<213> ORGANISM: Propionibacterium acnes

<400> SEQUENCE: 41

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat     120
cttacttatg tatatttcta agctatagcg tctaccctttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgattctg gattcctatt gtcgcccttta ttagggcaag cggtgccagt agcagaatat   360
gtcacctcaa caactcgatc caccccctgcc cattacatgg gtaacatatc catggaggtt   420
cgatgtatac tcgaggatac agtcgtccat cacgcccgcc tacataccca ttacatcagc   480
atag                                                                 484
```

<210> SEQ ID NO 42
<211> LENGTH: 484
<212> TYPE: DNA
<213> ORGANISM: Propionibacterium acnes

<400> SEQUENCE: 42

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat     120
cttacttatg tatatttcta agctatagcg tctaccctttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgattctg gattcctatt gtcgcccttta ttagggcaag cggtgccagt agcagaatat   360
gtcacctcaa caactcgatc caccccctgcc cattacatgg gtaacatatc catggaggtt   420
cgatgtatac tcgaggatac agtcgtccat cacgcccgcc tacataccca ttacaccagc   480
atag                                                                 484
```

<210> SEQ ID NO 43
<211> LENGTH: 484
<212> TYPE: DNA
<213> ORGANISM: Propionibacterium acnes

<400> SEQUENCE: 43

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat     120
cttacttatg tatatttcta agctatagcg tctaccctttg tcagacccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgattctg gattcctatt gtcgcccttta ttagggcaag cggtgccagt agcagaatat   360
gtcacctaaa caactcgatc caccccctgcc cattacatgg gtaacatatc catggaggtt   420
cgatgtatac tcgaggatac agtcgtccat cacgcccgcc tacataccca ttacatcagc   480
atag                                                                 484
```

<210> SEQ ID NO 44
<211> LENGTH: 484

<212> TYPE: DNA
<213> ORGANISM: Propionibacterium acnes

<400> SEQUENCE: 44

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagaccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatcccca ttacatcagc    480
atag                                                                  484
```

<210> SEQ ID NO 45
<211> LENGTH: 484
<212> TYPE: DNA
<213> ORGANISM: Propionibacterium acnes

<400> SEQUENCE: 45

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagaccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgcta gattcctatt gtcgccctta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatcccca ttacatcagc    480
atag                                                                  484
```

<210> SEQ ID NO 46
<211> LENGTH: 484
<212> TYPE: DNA
<213> ORGANISM: Propionibacterium acnes

<400> SEQUENCE: 46

```
gttacacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatagcg tctacccttg tcagaccag gacgatgggt    180
gtcacatccc ctttctagtc aacctaagag aggaggaaat gccgcgatat atgttccacc    240
ctgtcatcac gaacgccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt    420
cgatgtatac tcgaggatac agtcgtccat cacgcccgcc tacatcccca ttacatcagc    480
atag                                                                  484
```

<210> SEQ ID NO 47
<211> LENGTH: 484
<212> TYPE: DNA

<213> ORGANISM: Propionibacterium acnes

<400> SEQUENCE: 47

```
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tatatttcta agctatagcg tctaccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgattctg gattcctatt gtcgcccta ttagggcaag cggtgccagt agcagaatat   360
gtcacctcaa caactcgatc caccctgcc cattacatgg gtaacatatc catggaggtt   420
cgatgtatac tcgaggatac agtcgtccat caagcccgcc tacataccca ttacatcagc   480
atag                                                                484
```

<210> SEQ ID NO 48
<211> LENGTH: 484
<212> TYPE: DNA
<213> ORGANISM: Propionibacterium acnes

<400> SEQUENCE: 48

```
gttgcacacc aggggtcaa cttggcgtcc tcagttcaaa attgattcaa actaacagtt    60
ccatgtcgga aaacagcacc aggaagctcg tgacatatcg tctttcattg cgagaaacat   120
cttacttatg tacatttcta agctatagcg tctaccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgatgctg gattcctatt gtcgcccta ttagggcaag cggtgccagt agcagaatat   360
gtcacctcaa caactcgatc caccctgcc cattacatgg gtaacatatc catggaggtt   420
cgatgtatac tcgaggatac agtcgtccat cacgcccgcc tacataccca ttacatcagc   480
atag                                                                484
```

<210> SEQ ID NO 49
<211> LENGTH: 484
<212> TYPE: DNA
<213> ORGANISM: Propionibacterium acnes

<400> SEQUENCE: 49

```
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctaccttg tcagacccag gacgatgggt   180
gtcacatccc ctttctagtc aacctaagag aggaggaaat gccgcgatat atgttccacc   240
ctgtcatcac gaacgccacc acaatctatc ccagaacagc cggcacttca ctcacgatgc   300
cccgatgctg gattcctatt gtcgcccta ttagggcaag cgatgccagt agcagaatat   360
gtcacctcaa caactcgatc caccctgcc cattacatgg gtaacatatc catggaggtt   420
cgatgtatac tcgaggatac agtcgtccat cacgcccgcc tacataccca ttacatcagc   480
atag                                                                484
```

<210> SEQ ID NO 50
<211> LENGTH: 484
<212> TYPE: DNA
<213> ORGANISM: Propionibacterium acnes

```
<400> SEQUENCE: 50
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatagcg tctacccttg tcagacccag gacgatgggt   180
gtcacacccc ctttctagtc aacctaagag aggaggaaat gccgcgatat atgttccacc   240
ctgtcatcac gaacgccacc acaatctatc cagaacagc cggcacttca ctcacgatgc   300
cccgatgctg gattcctatt gtcgccctta ttagggcaag cggtgccagt agcagaatat   360
gtcacctcaa caactcgatc cacccctgcc cattacatgg gtaacatatc catggaggtt   420
cgatgtatac tcgaggatac agtcgtccat cacgcccgcc tacataccca ttacatcagc   480
atag                                                                484

<210> SEQ ID NO 51
<211> LENGTH: 484
<212> TYPE: DNA
<213> ORGANISM: Propionibacterium acnes

<400> SEQUENCE: 51
gttgcacacc aggggtcaa cttggcgtcc tcagttcaaa attgattcaa actaacagtt    60
ccatgtcggg aaacagcacc aggaagctcg tgacatatcg cctttcattg cgagaaacat   120
cttacttatg tacatttcta agctatagcg tctacccttg tcagacccag gacgatgggt   180
gtcacatccc ctttctagtc aacctaagag aggaggaaat gccgcgatat atgttccacc   240
ctgtcatcac gaacgccacc acaatcgatc cagaacagc cggcacttca ctcacgatgc    300
cccgatgctg gattcctatt gtcgccctta ttagggcaag cggtgccagt agcagaatat   360
gtcacctcaa caactcgatc cacccctgcc cattacatgg gtaacatatc catggaggtt   420
cgatgtatac tcgaggatac agtcgtccat cacgcccgcc tacataccca ttacatcagc   480
atag                                                                484

<210> SEQ ID NO 52
<211> LENGTH: 484
<212> TYPE: DNA
<213> ORGANISM: Propionibacterium acnes

<400> SEQUENCE: 52
gttgcacacc aggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agctatatcg tctacccttg tcagacccag gacgatggat   180
gtcacatccc ctttctagtc aacctaagag aggaggaaat gccgcgatat atgttccacc   240
ctgtcatcac gaaggccacc acaatctatc cagaacagc cggcacttca ctcacgatgc    300
cccgatgctg gattcctatt gtcgccctta ttagggcaag cggtgccagt agcagaatat   360
gtcacctcaa caactcgatc cacccctgcc cattacatgg gtaacatatc catggaggtt   420
cgatgtatat tcgaggatac agtcgtccat cacgcccgcc tacataccca ttacatcagc   480
atag                                                                484

<210> SEQ ID NO 53
<211> LENGTH: 484
<212> TYPE: DNA
<213> ORGANISM: Propionibacterium acnes
```

<400> SEQUENCE: 53

```
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatatcg tctaccttg tcagacccag gacgatggat     180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctca ttagggcaag cggtgccagt agcagaatat    360
gtcacctcaa caactcgatc caccctgcc cattacatgg gtaacatatc catggaggtt     420
cgatgtatat tcgaggatac agtcgtccat cacgcccgcc tacataccca ttacatcagc    480
atag                                                                484

<210> SEQ ID NO 54
<211> LENGTH: 484
<212> TYPE: DNA
<213> ORGANISM: Propionibacterium acnes

<400> SEQUENCE: 54
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatatcg tccaccttg tcagacccag gacgatggat     180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt     420
cgatgtatat tcgaggatac agtcgtccat cacgcccgcc tacataccca ttacatcagc    480
atag                                                                484

<210> SEQ ID NO 55
<211> LENGTH: 484
<212> TYPE: DNA
<213> ORGANISM: Propionibacterium acnes

<400> SEQUENCE: 55
gttgcacacc aggggtcaa cttggcgtcc tcagttcaaa attgattcaa actaacagtt      60
ccatgtcggg aaacagcacc aggaagctcg tgacatatcg tctttcattg cgagaaacat    120
cttacttatg tacatttcta agctatatcg tctaccttg tcagacccgg gacgatggat     180
gtcacatccc ctttctagtc aacctaagag aggaggaaat gccgcgatat atgttccacc    240
ctgtcatcac gaaggccacc acaatctatc ccagaacagc cggcacttca ctcacgatgc    300
cccgatgctg gattcctatt gtcgccctta ttagggcaag cggtgccagt agcagaatat    360
gtcacctcaa caactcgatc caccctgcc cattacatgg gtaacatatc catggaggtt     420
cgatgtatat tcgaggatac agtcgtccat cacgcccgcc tacataccca ttacatcagc    480
atag                                                                484

<210> SEQ ID NO 56
<211> LENGTH: 484
<212> TYPE: DNA
<213> ORGANISM: Propionibacterium acnes

<400> SEQUENCE: 56
```

```
gttgcacacc aggggggtcaa cttggcgtcc tcagttcaaa attgattcaa actaacagtt    60
ccatgtcggg aaacagcacc aggaagctcg tgacatatcg tctttcattg cgagaaacat   120
cttacttatg tacatttcta agccatatcg tctaccctttg tcagacccag gacgatggat  180
gtcacatccc ctttctagtc aacctaagag aggaggaaat gccgcgatat atgttccacc   240
ctgtcatcac gaaggccacc acaatctatc ccagaacagc cggcacttca ctcacgatgc   300
cccgatgctg gattcctatt gtcgccctta ttagggcaag cggtgccagt agcagaatat   360
gtcacctcaa caactcgatc caccccctgcc cattacatgg gtaacatatc catggaggtt  420
cgatgtatat tcgaggatac agtcgtccat cacgcccgcc tacatacccca ttacatcagc  480 atag                                                               484

<210> SEQ ID NO 57
<211> LENGTH: 484
<212> TYPE: DNA
<213> ORGANISM: Propionibacterium acnes

<400> SEQUENCE: 57
gttgcacacc aggggggtcaa cttggtgtcc tcagttcaaa attgattcaa actaacggtt   60
ccgtgtcggg aaacagcacc agaaaactcg tgacatatcg tctttcattg cgagaaacat   120
cttacttata cacatttcta agctatattg tctaccctg tcagacccag gacgatgggt    180
gtcatatccc ctttccagtc aacctaagaa gggaggaaat gccgcgatat atgttccgcc   240
ctgtcatcat gaatgccacc acaatctatc ccggaacagc cgtacttcac ccaccatgcc   300
ccgatgctgg attcctattg tcgcccttat tagagcaagc ggtgccagca gcagaatatt   360
tcacctcagc aactcgatcc gctcctgccc attacatggg taacatatcc atggaggtac   420
gatgtatgca tcgaggatgc agtcgtctac tatgcccgcc tacatacccca ttccatcagc  480 atag                                                               484

<210> SEQ ID NO 58
<211> LENGTH: 484
<212> TYPE: DNA
<213> ORGANISM: Propionibacterium acnes

<400> SEQUENCE: 58
gttgcacacc aggggggtcaa cttggtgtcc tcagttcaaa attggttcaa actaacggtt   60
ccgtgtcggg aaacagcacc agaaaactcg tgacatatcg tctttcattg cgagaaacat   120
cttacttata cacatttcta agctatattg tctaccctg tcagacccag gacgatgggt    180
gtcatatccc ctttccagtc aacctaagaa gggaggaaat gccgcgatat atgttccgcc   240
ctgtcatcat gaatgccacc acaatctatc ccggaacagc cgtacttcac ccaccatgcc   300
ccgatgctgg attcctattg tcgcccttat tagagcaagc ggtgccagca gcagaatatt   360
tcacctcagc aactcgatcc gctcctgccc attacatggg taacatatcc atggaggtac   420
gatgtatgca tcgaggatgc agtcgtctac tatgcccgcc tacatacccca ttccatcagc  480 atag                                                               484

<210> SEQ ID NO 59
<211> LENGTH: 483
<212> TYPE: DNA
<213> ORGANISM: Propionibacterium acnes

<400> SEQUENCE: 59
```

| | |
|---|---|
| gttgcacacc aggggggtcaa cttggtgtcc tcagttcaaa attgattcaa actaacggtt | 60 |
| ccgtgtcggg aaacagcacc agaaaactcg tgacatatcg tctttcattg cgagaaacat | 120 |
| cttacttata cacatttcta agctatatgt ctacccctgt cagacccagg acgatgggtg | 180 |
| tcatatcccc tttccagtca acctaagaag ggaggaaatg ccgcgatata tgttccgccc | 240 |
| tgtcatcatg aatgccacca caatctatcc cggaacagcc gtacttcacc caccatgccc | 300 |
| cgatgctgga ttcctattgt cgcccttatt agagcaagcg gtgccagcag cagaatattt | 360 |
| cacctcagca actcgatccg ctcctgccca ttacatgggt aacatatcca tggaggtacg | 420 |
| atgtatgcat cgaggatgca gtcgtctact atgcccgcct acatacccat tccatcagca | 480 |
| tag | 483 |

<210> SEQ ID NO 60
<211> LENGTH: 484
<212> TYPE: DNA
<213> ORGANISM: Propionibacterium acnes

<400> SEQUENCE: 60

| | |
|---|---|
| gttgcacacc aggggggtcaa cttggtgtcc tcagttcaaa attgattcaa actaacggtt | 60 |
| ccgtgtcggg aaacagcacc agaaaactcg taacatatcg tctttcattg cgagaaacat | 120 |
| cttacttata cacatttcta agctatattg tctaccccctg tcagacccag gacgatgggt | 180 |
| gtcatatccc ctttccagtc aacctaagaa gggaggaaat gccgcgatat atgttccgcc | 240 |
| ctgtcatcat gaatgccacc acaatctatc ccggaacagc cgtacttcac ccaccatgcc | 300 |
| ccgatgctgg attcctattg tcgcccttat tagagcaagc ggtgccagca gcagaatatt | 360 |
| tcacctcagc aactcgatcc gctcctgccc attacatggg taacatatcc atggaggtac | 420 |
| gatgtatgca tcgaggatgc agtcgtctac tatgcccgcc tacatacccca ttccatcagc | 480 |
| atag | 484 |

<210> SEQ ID NO 61
<211> LENGTH: 484
<212> TYPE: DNA
<213> ORGANISM: Propionibacterium acnes

<400> SEQUENCE: 61

| | |
|---|---|
| gttgcacacc aggggggtcaa cttggtgtcc tcagttcaaa attgattcaa actaacggtt | 60 |
| ccgtgtcggg aaacagcacc agaaaactcg tgacatatcg tctttcattg cgagaaacat | 120 |
| cttacttata cacatttcta agctatattg tctaccccctg tcagacccag gacgatgggt | 180 |
| gtcatatccc ctttccagtc aacctaagaa gggaggaaat gccgcgatat atgttccgcc | 240 |
| ctgtcatcat gaatgccacc acaatctatc ccggaacagc cgtacttcac ccaccatgcc | 300 |
| tcgatgctgg attcctattg tcgcccttat tagagcaagc ggtgccagca gcagaatatt | 360 |
| tcacctcagc aactcgatcc gctcctgccc attacatggg taacatatcc atggaggtac | 420 |
| gatgtatgca tcgaggatgc agtcgtctac tatgcccgcc tacatacccca ttccatcagc | 480 |
| atag | 484 |

<210> SEQ ID NO 62
<211> LENGTH: 484
<212> TYPE: DNA
<213> ORGANISM: Propionibacterium acnes

<400> SEQUENCE: 62

| | |
|---|---|
| gttgcacacc aggggggtcaa cttggtgtcc tcagttcaaa attgattcaa actaacggtt | 60 |

```
ccgtgtcggg aaacagcacc agaaaactcg tgacatatcg tctttcattg cgagaaacat      120
cttatttata cacatttcta agctatattg tctacccctg tcagacccag gacgatgggt      180
gtcatatccc ctttccagtc aacctaagaa gggaggaaat gccgcgatat atgttccgcc      240
ctgtcatcat gaatgccacc acaatctatc ccggaacagc cgtacttcac ccaccatgcc      300
ccgatgctgg attcctattg tcgcccttat tagagcaagc ggtgccagca gcagaatatt      360
tcacctcagc aactcgatcc gctcctgccc attacatggg taacatatcc atggaggtac      420
gatgtatgca tcgaggatgc agtcgtctac tatgcccgcc tacatacccca ttccatcagc     480 atag                                                                  484

<210> SEQ ID NO 63
<211> LENGTH: 484
<212> TYPE: DNA
<213> ORGANISM: Propionibacterium acnes

<400> SEQUENCE: 63
gttgcacacc aggggggtcaa cttggtgtcc tcagttcaaa attgattcaa actaacggtt     60
ccgtgtcggg aaacagcacc agaaaactcg tgacatatcg tctttcattg cgagaaacat     120
cttacttata cacatttcta agctatattg tctaccccctg tcagacccag gacgatgggt    180
gtcatatccc ctttccagtc aacctaagaa ggaaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggt taacatatcc atggaggtac    420
gatgtatgca tcgaggatgc agtcgtctac tatgcccgcc tacatacccca ttccatcagc   480 atag                                                                 484

<210> SEQ ID NO 64
<211> LENGTH: 484
<212> TYPE: DNA
<213> ORGANISM: Propionibacterium acnes

<400> SEQUENCE: 64
attgcacacc aggggggtcaa cttggtgtcc tcagttcaaa attggttcaa actaacggtt    60
ccgtgtcggg aaacagcacc agaaaactcg tgacatatcg tctttcattg cgagaaacat    120
cttacttata cacatttcta agctatattg tctaccccctg tcagacccag gacgatgggt   180
gtcatatccc ctttccagtc aacctaagaa gggaggaaat gccgcgatat atgttccgcc   240
ctgtcatcat gaatgccacc acaatctatc ccggaacagc cgtacttcac ccaccatgcc   300
ccgatgctgg attcctattg tcgcccttat tagagcaagc ggtgccagca gcagaatatt   360
tcacctcagc aactcgatcc gctcctgccc attacatggg taacatatcc atggaggtac   420
gatgtatgca tcgaggatgc agtcgtctac tatgcccgcc tacatacccca ttccatcagc  480 atag                                                                484

<210> SEQ ID NO 65
<211> LENGTH: 484
<212> TYPE: DNA
<213> ORGANISM: Propionibacterium acnes

<400> SEQUENCE: 65
gttgcacacc aggggggtcaa cttggtgtcc tcagttcaaa attggttcaa actaacggtt    60
```

```
ccgtgtcggg aaacagcacc agaaaactcg tgacatatcg tctttcattg cgagaaacat    120
cttacttata cacatttcta agctatattg tctacccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctatgg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                  484

<210> SEQ ID NO 66
<211> LENGTH: 483
<212> TYPE: DNA
<213> ORGANISM: Propionibacterium acnes

<400> SEQUENCE: 66
gttgcacacc aggggggtcaa cttggtgtcc tcagttcaaa attgattcaa actaacggtt    60
ccgtgtcggg aaacagcacc agaaaactcg tgacatatca tctttcattg cgagaaacat   120
cttacttata cacatttcta agctatatgt ctacccctgt cagacccagg acgatgggtg   180
tcatatcccc tttccagtca acctaagaag ggaggaaatg ccgcgatata tgttccgccc   240
tgtcatcatg aatgccacca caatctatcc ggaacagcc gtacttcacc caccatgccc    300
cgatgctgga ttcctattgt cgcccttatt agagcaagcg gtgccagcag cagaatattt   360
cacctcagca actcgatccg ctcctgccca ttacatggga acatatcca tggaggtacg    420 atgtatgcat cgaggatgca gtcgtctact atgcccgcct acatacccat tccatcagca    480
tag                                                                   483

<210> SEQ ID NO 67
<211> LENGTH: 484
<212> TYPE: DNA
<213> ORGANISM: Propionibacterium acnes

<400> SEQUENCE: 67
gttgcacacc aggggggtcaa cttggtgtcc tcagttcaaa attggttcaa actaacggtt    60
ccgtgtcggg aaacagcacc agaaaactcg tgacatgtcg tctttcattg cgagaaacat   120
cttacttata cacatttcta agctatattg tctacccctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                  484

<210> SEQ ID NO 68
<211> LENGTH: 484
<212> TYPE: DNA
<213> ORGANISM: Propionibacterium acnes

<400> SEQUENCE: 68
gttgcacacc aggggggtcaa cttggtgtcc tcagttcaaa attggttcaa actaacggtt    60
ccgtgtcggg aaacagcacc agaaaactcg tgacatatcg tctttcattg cgagaaacat   120
```

```
cttacttata cacatttcta agctatactg tctaccsctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                 484
```

<210> SEQ ID NO 69
<211> LENGTH: 484
<212> TYPE: DNA
<213> ORGANISM: Propionibacterium acnes

<400> SEQUENCE: 69

```
gttgcacacc aggggtcaa cttggtgtcc tcagttcaaa attggttcaa actaacggtt     60
ccgtgtcggg aaacagcacc agaaaacttg tgacatatcg tctttcattg cgagaaacat    120
cttacttata cacatttcta agctatattg tctaccsctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                 484
```

<210> SEQ ID NO 70
<211> LENGTH: 484
<212> TYPE: DNA
<213> ORGANISM: Propionibacterium acnes

<400> SEQUENCE: 70

```
gttgcacacc aggggtcaa cttggtgtcc tcagttcaaa attggttcaa actaacggtt     60
ccgtgtcggg aaacagcacc agaaaactca tgacatatcg tctttcattg cgagaaacat    120
cttacttata cacatttcta agctatattg tctaccsctg tcagacccag gacgatgggt    180
gtcatatccc ctttccagtc aacctaagaa gggaggaaat gccgcgatat atgttccgcc    240
ctgtcatcat gaatgccacc acaatctatc ccggaacagc cgtacttcac ccaccatgcc    300
ccgatgctgg attcctattg tcgcccttat tagagcaagc ggtgccagca gcagaatatt    360
tcacctcagc aactcgatcc gctcctgccc attacatggg taacatatcc atggaggtac    420
gatgtatgca tcgaggatgc agtcgtctac tatgcccgcc tacataccca ttccatcagc    480
atag                                                                 484
```

<210> SEQ ID NO 71
<211> LENGTH: 484
<212> TYPE: DNA
<213> ORGANISM: Propionibacterium acnes

<400> SEQUENCE: 71

```
gttgcacacc aggggtcaa cttggtgtcc tcagttcaaa attgattcaa actaacggtt     60
ccgtatcggg aaacagcacc agaaaactcg ggacatatcg tctttcattg cgagaaaaat    120
```

| | |
|---|---:|
| cttacttatg cgcatttcta agctatagcg tctacccttg tcagacccag gacgatgagt | 180 |
| gtcacatccc ctttccagtc aacctaagag aggaggaaat gccgcgatat atgctccgcc | 240 |
| ctgtcatcac gaaagccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcag caactcgatc cgcccctgcc cattacatgg gtaacatatc catggaggtt | 420 |
| cgatgtatac tcgaggatac agtcgcccat cacgccagcc tacatacccca ttacatcagc | 480 |
| atag | 484 |

<210> SEQ ID NO 72
<211> LENGTH: 484
<212> TYPE: DNA
<213> ORGANISM: Propionibacterium acnes

<400> SEQUENCE: 72

| | |
|---|---:|
| gttgcacacc aggggtcaa cttggtgtcc tcagttcaaa attgattcaa actaacggtt | 60 |
| ccgtatcggg aaacagcacc agaaaactcg ggacatatcg tctttcattg cgagaaaaat | 120 |
| cttacttatg cgcatttcta agctatagcg tctacccttg ccagacccag gacgatgagt | 180 |
| gtcacatccc ctttccagtc aacctaagag aggaggaaat gccgcgatat atgctccgcc | 240 |
| ctgtcatcac gaaagccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcag caactcgatc cgcccctgcc cattacatgg gtaacatatc catggaggtt | 420 |
| cgatgtatac tcgaggatac agtcgcccat cacgccagcc tacatacccca ttacatcagc | 480 |
| atag | 484 |

<210> SEQ ID NO 73
<211> LENGTH: 484
<212> TYPE: DNA
<213> ORGANISM: Propionibacterium acnes

<400> SEQUENCE: 73

| | |
|---|---:|
| gttgcacacc aggggtcaa cttggtgtcc tcagttcaaa attgattcaa actaacggtt | 60 |
| ccgtatcggg aaacagcacc agaaaactcg ggacatatcg tctttcattg cgagaaaaat | 120 |
| cttacttatg cgcatttcta agctatatcg tctacccttg ccagacccag gacgatgagt | 180 |
| gtcacatccc ctttccagtc aacctaagag aggaggaaat gccgcgatat atgctccgcc | 240 |
| ctgtcatcac gaaagccacc acaatctatc ccagaacagc cggcacttca ctcacgatgc | 300 |
| cccgatgctg gattcctatt gtcgccctta ttagggcaag cggtgccagt agcagaatat | 360 |
| gtcacctcag caactcgatc cgcccctgcc cattacatgg gtaacatatc catggaggtt | 420 |
| cgatgtatac tcgaggatac agtcgcccat cacgccagcc tacatacccca ttacatcagc | 480 |
| atag | 484 |

<210> SEQ ID NO 74
<211> LENGTH: 484
<212> TYPE: DNA
<213> ORGANISM: Propionibacterium acnes

<400> SEQUENCE: 74

| | |
|---|---:|
| gttgcacacc aggggtcaa cttggtgtcc tcagttcaaa attgattcaa actaacggtt | 60 |
| ccgtgtcggg aaacagcacc agaaaactcg ggacatatcg tctttcattg cgagaaaaat | 120 |
| cttacttatg cgcatttcta agctatagcg tctacccttg tcagacccag gacgatgagt | 180 |

```
gtcacatccc ctttccagtc aacctaagag aggaggaaat gccgcgatat atgctccgcc    240
ctgtcatcac gaaagccacc acaatctatc ccagaacagc cggcacttca ctcacgatgc    300
cccgatgctg gattcctatt gtcgcccttc ttagggcaag cggtgccagt agcagaatat    360
gtcacctcag caactcgatc cgcccctgcc cattacatgg ttaacatatc catggaggtt    420
cgatgtatac tcgaggatac agtcgcccat cacgccagcc tacatacccc ttacatcagc    480
atag                                                                484

<210> SEQ ID NO 75
<211> LENGTH: 484
<212> TYPE: DNA
<213> ORGANISM: Propionibacterium acnes

<400> SEQUENCE: 75
gttgcacacc aggggggtcaa cttggtgtcc tcagttcaaa attgattcaa actaacggtt    60
ccgtgtcggg aaacagcacc agaaaactcg ggacatatcg tctttcattg cgagaaaaat    120
cttacttatg cgcatttcta agctatagcg tctacccttg tcagacccag gacgatgagt    180
gtcacatccc ctttccagtc aacctaagag aggaggaaat gccgcgatat atgctccgcc    240
ctgtcatcac gaaagccacc acaatctatc ccagaacagc cggcacttca ctcacgatgc    300
cccgatgctg gattcctatt gtcgcccttc ttagggcaag cggtgccagt agcagaatat    360
gtcacctcag caactcgatc cgcccctgcc cattacatgg gtaacatatc catggaggtt    420
cgatgtatac tcgaggatac agtcgcccat cacgccagcc tacatacccc ttacatcagc    480
atag                                                                484

<210> SEQ ID NO 76
<211> LENGTH: 484
<212> TYPE: DNA
<213> ORGANISM: Propionibacterium acnes

<400> SEQUENCE: 76
gttgcacacc aggggggtcaa cttggtgtcc tcagttcaaa attgattcaa actaacggtt    60
ccgtatcggg aaacagcacc agaaaactcg ggacatatcg tctttcattg cgagaaaaat    120
cttacttatg cgcatttcta agctatagcg tctacccttg tcagacccag gacgatgagt    180
gtcacatccc ctttccagtc aacctaagag aggaggaaat gccgcgatat atgctccgcc    240
ctgtcatcac gaaagccacc acaatctatc ccagaacagc cggcacttca ctcacgatgc    300
cccgatgctg gattcctatt gtcgcccttc ttagggcaag cggtgccagt agcagaatat    360
gtcacctcag caactcgatc cgcccccgcc cattacatgg gtaacatatc catggaggtt    420
cgatgtatac tcgaggatac agtcgcccat cacgccagcc tacatacccc ttacatcagc    480
atag                                                                484

<210> SEQ ID NO 77
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 77
cagcggcgct gctaagaact t                                             21

<210> SEQ ID NO 78
```

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
ccggctggca aatgaggcat                                              20

<210> SEQ ID NO 79
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 79
tcgtcggcag cgtcagatgt gtataagaga cagcagcggc gctgctaaga actt        54

<210> SEQ ID NO 80
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 80
gtctcgtggg ctcggagatg tgtataagag acagccggct ggcaaatgag gcat        54

<210> SEQ ID NO 81
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 81
tcgtcggcag cgtcagatgt gtataagaga cagcagcggc gctgctaaga actt        54

<210> SEQ ID NO 82
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 82
gtctcgtggg ctcggagatg tgtataagag acagccggct ggcaaatgag gcat        54
```

METHODS AND COMPOSITIONS FOR CHANGING THE COMPOSITION OF THE SKIN MICROBIOME USING COMPLEX MIXTURES OF BACTERIAL STRAINS

RELATED APPLICATIONS

This application is a national stage filing under 35 U.S.C. § 371 of international application number PCT/IB2017/001481, filed Oct. 19, 2017, which claims the benefit under 35 U.S.C. § 119(e) of U.S. Provisional Application Ser. No. 62/410,329, filed on Oct. 19, 2016, entitled "METHODS AND COMPOSITIONS FOR CHANGING THE COMPOSITION OF THE SKIN MICROBIOME USING COMPLEX MIXTURES OF BACTERIAL STRAINS," and U.S. Provisional Application Ser. No. 62/536,761, filed on Jul. 25, 2017, entitled "METHODS AND COMPOSITIONS FOR CHANGING THE COMPOSITION OF THE SKIN MICROBIOME USING COMPLEX MIXTURES OF BACTERIAL STRAINS," the entire disclosure of each of which is incorporated by reference herein in its entirety.

FIELD OF INVENTION

The invention relates to methods and compositions for modifying the skin microbiome.

BACKGROUND OF INVENTION

The human body is host to a highly complex and rich microbial community. These microorganisms are generally harmless and contribute to a healthy state by producing vitamins, cooperating with digesting food, or stimulating the immune system. The human microbiota mainly resides on the surface and in deep layers of skin, in the saliva and oral mucosa, in the conjunctiva, and in the gastrointestinal tracts.

It has been demonstrated, primarily in the gut, that human microbiota have fundamental roles in human health and disease. The skin is colonized by a large number of microorganisms, most of them are beneficial or harmless. However, the skin microbiome has specific compositions in diseases states of skin that are different compared to healthy skin. Diseases such as acne vulgaris are associated with strong alterations of the microbiome.

SUMMARY OF INVENTION

Aspects of the invention relate to a composition for topical administration to the skin comprising two or more different live *Propionibacterium acnes* (*P. acnes*) bacterial strains, wherein the composition comprises a *P. acnes* single-locus sequence typing (SLST) type C3 strain and/or a *P. acnes* SLST type K8 strain, and wherein the composition further comprises peptone.

In some embodiments, the composition further comprises a *P. acnes* SLST type A5 strain. In some embodiments, the composition further comprises a *P. acnes* SLST type F4 strain.

In some embodiments, the concentration of peptone is from about 0.05%-1%. In some embodiments, the concentration of peptone is about 0.25%. In some embodiments, the peptone is trypsin-digested peptone from casein.

In some embodiments, the composition further comprises a thickener. In some embodiments, the thickener comprises hydroxyethyl cellulose. In some embodiments, the hydroxyethyl cellulose comprises NATROSOL® hydroxyethylcellulose (HEC). In some embodiments, the concentration of the thickener is from about 1%-5%. In some embodiments, the concentration of gelling agent is about 2.5%.

In some embodiments, the concentration of each live *P. acnes* bacterial strain is at least 5% of the composition. In some embodiments, a *P. acnes* SLST type C3 strain and a *P. acnes* SLST type K8 strain are at approximately equal concentrations within the composition. In some embodiments, a *P. acnes* SLST type C3 strain is present at a higher concentration than the other live *P. acnes* bacterial strains.

In some embodiments, the composition comprises a *P. acnes* SLST type C3 strain, a *P. acnes* SLST type A5 strain, a *P. acnes* SLST type F4 strain, and a *P. acnes* SLST type K8 strain, optionally wherein the relative concentration of each strain is approximately 55%, 30%, 10%, and 5%, respectively.

In some embodiments, the composition includes at least $10^4$ colony-forming units per milliliter (CFU/ml) of each live *P. acnes* bacterial strain. In some embodiments, the composition includes about $10^4$-$10^9$ colony-forming units per milliliter (CFU/ml) of each live *P. acnes* bacterial strain.

In some embodiments, the composition is in the form of a gel, cream, ointment or lotion.

In some embodiments, the composition further comprises an additional *P. acnes* bacterial strain selected from the group consisting of: D1, H1, H2, H3, K1, K2, K4, K6, K9, and L1 SLST type strains.

The invention, in some embodiments, is a method comprising administering the composition to a subject. In some embodiments, the subject is a human subject. In some embodiments, the method comprises improving the appearance of the skin and/or maintaining healthy skin. In some embodiments, the method comprises treating or preventing a condition selected from the group consisting of: acne, oily skin, progressive macular hypomelanosis, dandruff, atopic eczema, atopic dermatitis and rosacea.

In some embodiments, the composition is for use in improving the appearance of the skin and/or maintaining healthy skin in a subject. In some embodiments, the composition is for use in treating or preventing a condition in a subject selected from the group consisting of: acne, oily skin, progressive macular hypomelanosis, dandruff, atopic eczema, atopic dermatitis and rosacea. In some embodiments, the subject is a human subject.

Aspects of the invention relate to use of a composition for improving the appearance of the skin and/or maintaining healthy skin in a subject, wherein the composition comprises two or more different live *Propionibacterium acnes* (*P. acnes*) bacterial strains, wherein the composition comprises a *P. acnes* SLST type C3 strain and/or a *P. acnes* SLST type K8 strain, and wherein the composition further comprises peptone.

Further aspects of the invention relate to use of a composition for treating or preventing a condition in a subject selected from the group consisting of: acne, oily skin, progressive macular hypomelanosis, dandruff, atopic eczema, atopic dermatitis and rosacea, wherein the composition comprises two or more different live *Propionibacterium acnes* (*P. acnes*) bacterial strains, wherein the composition comprises a *P. acnes* SLST type C3 strain and/or a *P. acnes* SLST type K8 strain, and wherein the composition further comprises peptone.

In some embodiments, the composition further comprises a *P. acnes* SLST type A5 strain. In some embodiments, the composition further comprises a *P. acnes* SLST type F4 strain. In some embodiments, the concentration of peptone is from about 0.05%-1%. In some embodiments, the concentration of peptone is about 0.25%. In some embodiments, the peptone is trypsin-digested peptone from casein. In some embodiments, the composition further comprises a thickener. In some embodiments, the thickener comprises hydroxyethyl cellulose. In some embodiments, the hydroxyethyl cellulose comprises NATROSOL® hydroxyethylcellulose (HEC). In some embodiments, the concentration of thickener is from about 1%-5%. In some embodiments, the concentration of gelling agent is about 2.5%.

In some embodiments, the concentration of each live *P. acnes* bacterial strain is at least 5% of the composition. In some embodiments, a *P. acnes* SLST type C3 strain and a *P. acnes* SLST type K8 strain are at approximately equal concentrations within the composition. In some embodiments, a *P. acnes* SLST type C3 strain is present at a higher concentration than the other live *P. acnes* bacterial strains. In some embodiments, the composition comprises a *P. acnes* SLST type C3 strain, a *P. acnes* SLST type A5 strain, a *P. acnes* SLST type F4 strain, and a *P. acnes* SLST type K8 strain, and wherein the relative concentration of each strain is approximately 55%, 30%, 10%, and 5%, respectively. In some embodiments, the composition includes at least $10^4$ colony-forming units per milliliter (CFU/ml) of each live *P. acnes* bacterial strain. In some embodiments, the composition includes about $10^4$-$10^9$ colony-forming units per milliliter (CFU/ml) of each live *P. acnes* bacterial strain. In some embodiments, the composition is in the form of a gel, cream, ointment or lotion.

In some embodiments, the composition further comprises an additional *P. acnes* bacterial strain selected from the group consisting of: D1, H1, H2, H3, K1, K2, K4, K6, K9, and L1 SLST type strains.

In some embodiments, a composition described herein does not include a ribotype 6 (RT6) strain of *P. acnes*. In some embodiments, a composition described herein does not include a Phylotype III strain of *P. acnes*. In some embodiments of methods described herein, the composition does not include a ribotype 6 (RT6) strain of *P. acnes*. In some embodiments of methods described herein, the composition does not include a Phylotype III strain of *P. acnes*. In some embodiments of uses described herein, the composition does not include a ribotype 6 (RT6) strain of *P. acnes*. In some embodiments of uses described herein, the composition does not include a Phylotype III strain of *P. acnes*.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 11A shows the dynamic development of the *P. acnes* population in acceptors and non-acceptors throughout the pilot study. In the acceptors group, *P. acnes* initially represented only 34% of the bacterial skin microbiome. After the BPO treatment, this value was further reduced before it increased to nearly the double after the bacterial gel was applied. The *P. acnes* population stabilized at 60% on Day 42. The dynamics in the non-acceptor group were similar. The non-acceptors ground state started at a higher level of 40% and in contrast to the acceptor group, the increase in the population was not significant on Day 42. FIG. 11B shows the relative ratios of *P. acnes* as box plots illustrating the spread of the data points. The difference between Day 1 and Day 42 in the acceptor group is highly statistically relevant (p=0.001) while the acceptor group is similar on Day 42 to Day 1.

DETAILED DESCRIPTION

Provided herein are compositions and methods for modulation of the skin microbiome. Compositions comprising two or more live P. acnes bacterial strains are described herein for use in maintaining healthy skin, such as skin that is free of acne, or for treating or preventing acne. Compositions comprising two or more live P. acnes bacterial strains can help skin to revert microbiome disease states to healthy microbiome states.

Without wishing to be bound by any theory, P. acnes may convert a signal precursor molecule (linoleic acid), which is naturally present in the sebum, to an active signaling molecule (trans-10, cis-12 linoleic acid), which stimulates in return sebum secretion, which is important for P. acnes colonization of the skin. Significantly, the production of this signaling molecule provides a connection between different aspects of the current understanding of the onset of acne.

As shown in Example 1, it was surprisingly found that different P. acnes strains have different levels of linoleic acid isomerase activity or final thresholds of concentration of trans-10, cis-12 linoleic acid. For example, a P. acnes SLST type A1 strain was found to produce the most trans-10, cis-12 linoleic acid isomer, while P. acnes SLST type strains C3, C1, F4, A5, K1, K2, K8 and L1 showed very little production of trans-10, cis-12 linoleic acid isomer.

Figure 7:
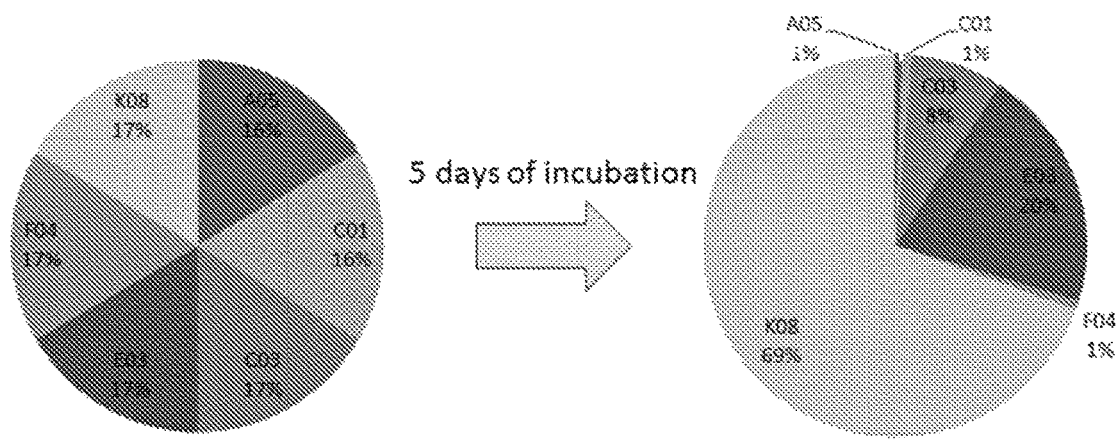
FIG. 7 depicts the change of relative concentrations of different *P. acnes* strains within a mixture of strains determined by sequencing reads before and after 5 days of growth on RCM agar. Surprisingly the strain K8, which was very slow-growing when used as isolate, became the dominant strain within the culture after 5 days of growth in a mixture of strains.

It was also surprisingly found that some strains exhibited different growth patterns when grown in a mixture of strains than when grown individually. For example, a P. acnes SLST type K8 strain was found to grow slowly individually, but when grown within a mixture of strains, it became the dominant strain within the composition after 5 days of incubation (FIG. 7). Accordingly, aspects of the invention relate to mixtures of strains that exhibit advantageous growth properties even when containing individual strains that may grow slowly in nature and would likely be outcompeted in nature.

It was also surprisingly found herein that mixtures of strains were able to tolerate higher levels of preservatives than individual strains. Accordingly, aspects of the invention relate to mixtures of P. acnes strains that can be established on the skin and that will have improved survival against exposure to certain compounds, such as products containing preservatives, compared to single P. acnes strains. This feature provides an unexpected advantage for bacterial mixtures compared to individual strains for the establishment and long term persistence on the skin of a human subject.

It is also surprisingly demonstrated herein, using two different formulations of two or more live P. acnes strains, that administration of live P. acnes strains can lead to a substantial reduction in non-inflamed lesions in subjects having acnes. In a pilot clinical study described in Example 5, 85% of subjects reported improvement in symptoms associated with acne following administration of formulations described herein.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the invention relate to the microbiome. As used herein, "microbiome" refers to all of the microorganisms inhabiting the body. The human microbiome has a fundamental role in human health and disease (Consortium, 2012; NIH HMP Working Group et al., 2009). The development of Next Generation Sequencing (NGS) technologies has allowed the study of these microbial communities with an unprecedented depth and resolution (see Human Microbiota issue, Nature 2012). More than 10,000 different bacterial strains colonize the human body, and there are ten times more bacteria than human cells in an average human body. Recent research has indicated that the composition of bacterial communities in the body is tightly connected to the health of the human body (Belkaid and Segre, 2014; Consortium, 2012; Zhao, 2010). As a result, distortions of the microbiome are linked to a variety of diseases.

The gut microbiome, and methods for targeted manipulation of the gut microbiome, has been investigated in depth (Doré and Blottière, 2015). An example of such a therapy is the treatment of the antibiotic-resistant bacteria Clostridium difficile with the help of "fecal transplantation" (van Nood et al., 2013; Olle, 2013).

Researchers recently began to investigate the skin microbiome (Belkaid and Segre, 2014; Oh et al., 2014). The skin is colonized by a large number of microorganisms, most of which are beneficial or harmless (Grice and Segre, 2011). However, diseases such as acne vulgaris are associated with strong alterations of the microbiome (Bek-Thomsen et al., 2008; Holmes, 2013; Kong et al., 2012). Acne, in particular, is considered to be linked to a distortion of the human skin microbiome (Fitz-Gibbon et al., 2013). This distortion is likely caused by a specific subset of the skin bacterium P. acnes (Lomholt and Kilian, 2010).

Herein, compositions and methods apply knowledge of the skin microbiome to develop treatments against skin disorders that originate or are influenced by distortions of the skin microbiome.

Acne

As used herein, "acne vulgaris" and "acne" are used interchangeably and refer to a skin condition that affects millions of people worldwide and is especially prevalent in teenagers. Acne is frequently associated with the formation of inflammatory and non-inflammatory lesions on the skin. Without wishing to be bound by any theory, acne may be associated, at least in part, with hair follicles that become clogged and/or inflamed. Acne is considered to be linked to the distortion of the human skin microbiome. This distortion may be caused by specific strains of the skin bacterium *P. acnes* (Fitz-Gibbon et al., 2013; Holmes, 2013; Lomholt and Kilian, 2010).

The development of acne is linked to the onset of sebum secretion from the sebaceous glands (Makrantonaki et al., 2011; Zouboulis, 2004). Also, the population density of *P. acnes* is directly linked to the amount of sebum produced (Kearney et al., 1984; King et al., 1982; Mourelatos et al., 2007). However, a clear molecular link between the presence of *P. acnes* and the disease acne, could until now, not be established. This is due, at least in part, to the fact that the skin of most adult humans is colonized by *P. acnes*, while symptoms of acne do not occur in many of those adults. In order for acne to occur, an inflammatory reaction must be triggered, which is accompanied by a change in the volume and composition of the sebum (Pappas et al., 2009).

Currently, standard treatment for acne is either long-term antibiotic treatment, such as treatment with Macrolide and/or Tetracycline antibiotics, or the systemic use of Isotretinoin (Berson et al., 2003). These treatments exhibit strong side effects and high relapse rates. For example, Isotretinoin causes skin irritation and also has teratogenic effects (causing birth defects) (McLane, 2001). In addition, the relapse rate with Isotretinoin is also unfavourable, at above 40% (Azoulay et al., 2007). Isotretinoin has been shown to reduce the volume of sebum production, thereby indirectly reducing the bacterial density on the skin (King et al., 1982). While antibiotics are a common treatment, in the last several decades, the number of bacterial strains that are resistant to one or more antibiotics has increased dramatically. (Leyden, 2001; Ross et al., 2001).

Another group of acne treatments include over-the-counter (OTC) products and cosmetics. Commonly used OTC products are broadband disinfection agents including benzoyl peroxide (e.g. Benzaknen, Galderma S. A., Lausanne, Switzerland and Aknefug, Dr. August Wolff GmbH & Co. KG Arzneimittel, Bielefeld, Germany) and salicylic acid. Additionally, there are a number of natural product lines which have limited or no proven efficacy.

Current therapies for skin disorders such as acne, that are linked to a distortion of the microbiome, are either ineffective or they are accompanied by severe side effects (McLane, 2001; Tripathi et al., 2013). Usually, the skin of a subject with acne improves during classical treatments, such as with antibiotics or hormones. However, the subject in most cases relapses after the end of the treatment. Isotretinoin has about a 41% relapse rate (Azoulay et al., 2007). Therefore, subjects are required to undergo long term treatments to keep the beneficial effects. This extreme relapse rate can be explained by the recolonization of the skin with the microbiome after stopping the therapy.

Compositions and methods described herein address an unmet need for an effective treatment of acne without notable side effects, and with prevention of relapse. The novel approach described herein can involve transplantation of a healthy microbiome. Surprisingly, strains of *P. acnes*, the same bacterial species that is thought to be involved in causing acne, can be used to treat or prevent acne, or to maintain skin in a condition where it is free of acne. Described herein are compositions comprising two or more live bacterial strains that can provide an improved skin condition without causing notable side effects. The live bacterial strains within the compositions described herein are *P. acnes* bacterial strains.

In some embodiments, the composition is a cosmetic. As used herein, a "cosmetic" refers to a product that is intended to enhance appearance. Cosmetic composition comprising one or more live bacterial strains as described herein can also be referred to as a "cosmeceuticals" (Draelos, 2009).

Aspects of the invention relate to administering compositions comprising two or more live *P. acnes* bacterial strains to the skin of a subject either alone, in combination with other therapies, or following another therapy. In some aspects, a composition comprising two or more live *P. acnes* bacterial strains can help the skin revert from a microbiome disease state to a healthy microbiome state. In some embodiments, the skin of the subject has already been treated with a standard acne therapy, such as with antibiotics, disinfectants, or hormones. Compositions comprising two or more live *P. acnes* bacterial strains described herein can be used as complementary recovery methods to standard treatments for acne, whereby the composition comprising two or more live *P. acnes* bacterial strains can reduce the relapse rate of acne after antibiotic treatment. For example, a composition comprising two or more live *P. acnes* bacterial strains can be applied after an antibiotic or disinfectant treatment when the skin of a subject is cleared of the majority of its natural bacteria. The live bacteria in the composition can displace pathogenic bacterial strains and help to recover a diverse, healthy and balanced skin microbiome. Accordingly, in some embodiments, methods described herein involve eradicating pathogenic bacterial strains from the skin and then adding live *P. acnes* bacteria to the skin to create a healthy skin microbiome.

Compositions comprising two or more live *P. acnes* bacterial strains as described herein can be used to decrease or increase the volume of the sebum production of an individual. Compositions comprising two or more live *P. acnes* bacterial strains as described herein can also be used to produce trans-10, cis-12 linoleic acid in the follicles or sebaceous glands and thereby deliver this active compound to the environment of the sebaceous glands. These methods circumvent problems associated with the standard topical application of trans-10, cis-12 linoleic acid.

Compositions comprising two or more live *P. acnes* bacterial strains as described herein can also be used to increase or decrease the bacterial density on the skin by providing a bacterial strain to the skin which will increase or decrease the sebum production on the skin, thereby indirectly changing the bacterial density.

Compositions comprising two or more live *P. acnes* bacterial strains as described herein can also be used to modify the ratio of select bacterial species compared to other bacterial species or compared to other components of the microbiota such as fungi or mites by administering a live bacterial strain to the skin that alters the sebum production, thereby indirectly altering the bacterial density of *P. acnes* on the skin.

Compositions comprising two or more live *P. acnes* bacterial strains as described herein can be used to maintain healthy skin, such as skin that is free of acne. In some embodiments, administration of such compositions can assist in preventing formation of acne. In some embodiments, such compositions can be used to treat acne or can be used to prevent reoccurrence of acne in a subject who has received a standard acne treatment.

The compositions comprising two or more live *P. acnes* bacterial strains include one or more strains of live bacteria that naturally colonise the skin. In some embodiments, the one or more strains are naturally occurring. However, the composition comprising the two or more bacterial strains is not naturally occurring. The composition comprising the two or more bacterial strains has different properties than the individual strains in nature.

*Propionibacterium acnes* (*P. acnes*)

*P. acnes* is a species of anaerobic Gram-positive rod bacteria that is associated with acne as well as other conditions such as chronic blepharitis and endophthalmitis. *P. acnes* strains are present on the skin of most people. It has been reported that some strains of *P. acnes* are pathogenic, while other strains of *P. acnes* are not. (Fitz-Gibbon et al., 2013; Lomholt et al., 2010.) As used herein, "pathogenic" *P. acnes* strains refers to *P. acnes* strains that are associated with acne. Disclosed herein are assays by which pathogenic and non-pathogenic strains of *P. acnes* can be identified and selected.

Strains of *P. acnes* have been shown to differ significantly in their metabolism and phenotypic behavior (Lomholt and Kilian, 2010). These differences include but are not limited to expressing neuraminidase, α-glucosidase or hyaluronidase and the ability to perform hemolysis of horse blood, ribose fermentation, erythritol fermentation or sorbitol fermentation. Further it has been shown that *P. acnes* express an active linoleic acid isomerase, which specifically converts cis 9, c-12 linoleic acid into trans-10, cis-12 linoleic acid (Rosson et al., 2004). Linoleic acid is a key molecule in the regulation of sebum production and a reduction of linoleic acid has been linked in multiple studies to the onset of acne (Downing et al., 1986; Letawe et al., 1998).

Further it has been shown that *P. acnes* dead cells or supernatants are able to increase lipid production in hamster sebocytes (Iinuma et al., 2009a).

Species of *P. acnes* have been classified into Clades I-III, further including subtypes: IA and IB. (Lomholt et al.) IA has been further subdivide into $IA_1$ and $IA_2$ (McDowell et al., 2012). Genetic analysis of *P. acnes* strains has been conducted to determine which strains may be pathogenic and associated with acne, and which strains may be non-pathogenic and not associated with acne. (Fitz-Gibbon et al., 2013, Lomholt et al., 2010, and Kasimatis et al., 2013). In some embodiments, a non-pathogenic *P. acnes* strain is a strain from one of the following classes of *P. acnes*: 1-2, II and IB. In some non-limiting embodiments, a non-pathogenic strain of *P. acnes* is selected from the group of non-pathogenic strains consisting of: D1, A5, C3, H1, H2, H3, K1, K2, K4, K6, K8, K9, L1, and F4 SLST type strains, as described in Scholz et al. (2014) *PLOS ONE* 9(8) e104199.

Figure 1:
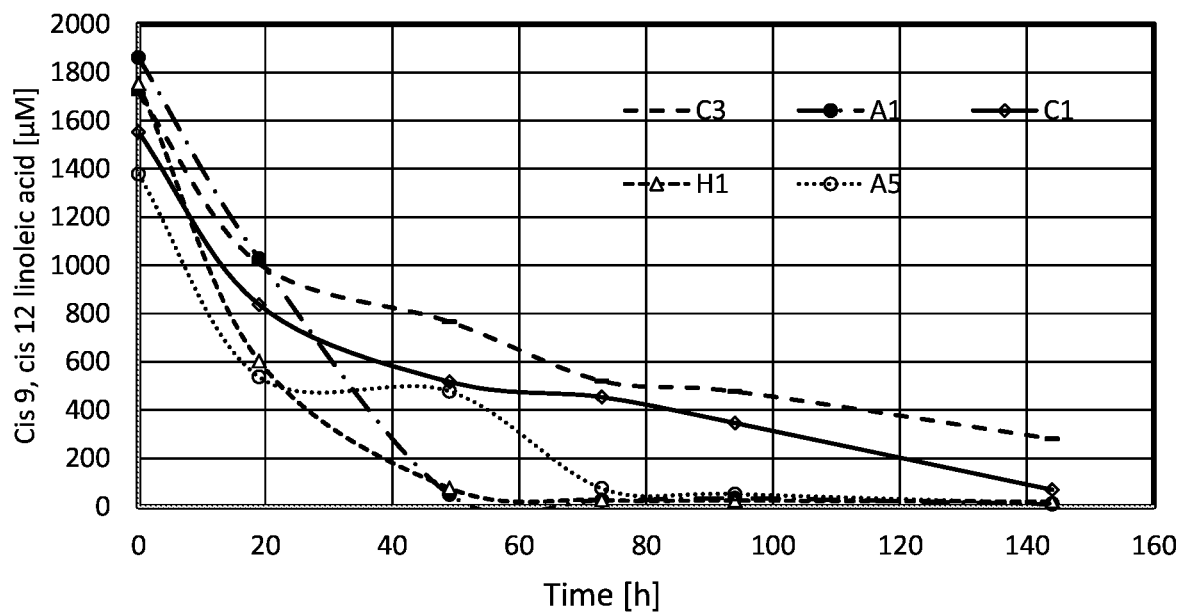
FIG. 1 depicts the consumption of cis-9, cis-12 linoleic acid of different *P. acnes* strains in RCM media.

As described in Scholtz et al., and as would be understood by one ordinary skill in the art, strains of *P. acnes* can be identified using single-locus sequence typing (SLST), involving PCR amplification and DNA sequencing of a target locus. An SLST scheme for *P. acnes* was developed and described in Scholz et al. using the target locus PPA2385 (referred to in Scholtz et al. as the "SLST target sequence"). A *P. acnes* database associated with the SLST scheme described in Scholtz et al. is available online at medbac.dk/slst/pacnes. Exemplary SLST type strains include A1-A24, B1, C1-C4, D1-D3, E1-E9, F1-F10, G1, H1-H5, K1-K14, and L1-L6. Users can enter a *P. acnes* sequence into the online database to identify SLST type strains. Other *P. acnes* strain identification and naming systems include MLST9 and MLST8 schemes, ribotyping, and type assignments based on recA and tly sequence analysis. FIG. 1 of Scholtz et al. demonstrates these different naming conventions. One of ordinary skill in the art would understand how a *P. acnes* strain could be identified and classified according to the different naming systems known in the art.

As used herein, "typing" a bacterial strain refers to identifying the bacterial strain, such as by using SLST. Table 1 lists allelic sequences used in SLST to identify strains described herein, such as *P. acnes* SLST type D1, A5, C3, H1, H2, H3, K1, K2, K4, K6, K8, K9, L1, and F4 strains. One of ordinary skill in the art would understand the strain designations used herein, corresponding to those disclosed in Scholtz et al., and would understand how to identify whether a *P. acnes* strain corresponds to any of these specific strains by using, e.g., SLST.

Accordingly, the *P. acnes* strains are described herein based on SLST-type designation using the target locus PPA2385 described in Scholtz et al. For example, "*P. acnes* strain C3" refers to *P. acnes* SLST type C3, using the target locus PPA2385 described in Scholtz et al. "*P. acnes* strain K8" refers to *P. acnes* SLST type K8, using the target locus PPA2385 described in Scholtz et al. "*P. acnes* strain A5" refers to *P. acnes* SLST-type A5, using the target locus PPA2385 described in Scholtz et al. and "*P. acnes* strain F4" refers to *P. acnes* SLST-type F4, using the target locus PPA2385 described in Scholtz et al.

Bacterial compositions described herein comprise two or more strains of *P. acnes*. For example, a bacterial composition can comprise 2, 3, 4, 5, 6, 7, 8, 9, 10, 11, 12, 13, 14, 15, 16, 17, 18, 19, 20 or more than 20 strains of *P. acnes*. In some embodiments, the composition comprises 2, 3, 4, or 5 different strains of *P. acnes*. One or more of the strains of *P. acnes* can be non-pathogenic strains. In some embodiments, all of the strains of *P. acnes* in a bacterial composition are non-pathogenic strains. In some embodiments strains of *P. acnes* are genotyped in order to identify the strain and to make a selection as to whether to include the strain in a composition. Strains of *P. acnes* included in bacterial compositions described herein can be selected to increase or decrease lipid production.

In some embodiments, a composition comprising two or more different *P. acnes* bacterial strains comprises *P. acnes* strain C3, *P. acnes* strain K8, or both *P. acnes* strain C3 and *P. acnes* strain K8. In some embodiments *P. acnes* strain C3 and *P. acnes* strain K8 are at approximately equal concentrations within the composition. In other embodiments, *P. acnes* strain C3 is at a higher concentration than *P. acnes* strain K8 within the composition. In other embodiments, *P. acnes* strain C3 is at a lower concentration than *P. acnes* strain K8 within the composition.

In some embodiments, a composition comprising two or more different *P. acnes* bacterial strains comprises *P. acnes* strain A5 and/or *P. acnes* strain F4. For example, a composition can include *P. acnes* strain C3 and/or *P. acnes* strain K8, and/or *P. acnes* strain A5 and/or *P. acnes* strain F4. In some embodiments, a composition includes *P. acnes* strain C3 and *P. acnes* strain K8 and *P. acnes* strain A5 and *P. acnes* strain F4.

In some embodiments, mixtures of *P. acnes* strains include one or more Clade I strains and one or more Clade II strains. Without wishing to be bound by any theory, Clade II strains may be less pathogenic; however, these strains can also be slower-growing than Clade I strains, and less likely to be able to colonize the skin on their own. Accordingly, aspects of the invention relate to mixtures of strains that include both Clade I and Clade II strains and which allow for colonization of the skin by Clade II strains.

In some aspects, compositions comprising one or more live *P. acnes* bacterial strains described herein include the *P. acnes* strain H1 (6609). (Hunyadkurti et al.) The genome of this *P. acnes* strain has been sequenced and is available at GenBank accession number CP002815. (Hunyadkurti et al.) In some embodiments, compositions comprising one or more live *P. acnes* bacterial strains described herein include strains of *P. acnes* that have certain CRISPR/CAS9 sequences. (Bruggemann, 2012, Fitz-Gibbon 2013). In some embodiments, compositions comprising one or more live *P. acnes* bacterial strains described herein include comprise one or more of *P. acnes* strains K1, K4 and H1 (6609). In some embodiments, compositions comprising one or more live *P. acnes* bacterial strains described herein comprise each of *P. acnes* strains K1, K4, D1, A5, C3 and H1 (6609).

Aspects of the invention relate to mixtures of *P. acnes* strains. Selection of *P. acnes* strains can involve, at least in part, a determination of whether the strain is pathogenic. This determination can be based on public information, prior reports, and/or experimental testing to determine whether a *P. acnes* strain is pathogenic or not. In some embodiments, only non-pathogenic *P. acnes* strains are selected.

Selection of *P. acnes* strains can also involve, at least in part, a determination of which strains, or combinations of strains, are stable in conditions that would be appropriate for use in a cosmetic or pharmaceutical composition. In some embodiments, *P. acnes* strains that exhibit increased stability are selected. Stability can be assessed using methods known in the art, such as by measuring a change in colony-forming units (CFU).

Strains of *P. acnes* included in bacterial compositions described herein can be naturally occurring or can be genetically modified. Strains that are genetically modified can be modified by natural mutagenesis and/or by genetic engineering. In some embodiments, the genetic modification of the *P. acnes* strain influences the production of trans-10, cis-12 linoleic acid and/or increases or decreases its linoleic acid isomerase activity. In some embodiments, *P. acnes* strains show different level of linoleic acid isomerase, which can be used to classify bacterial strains and/or to select specific bacterial strains.

In some embodiments, one or more of the *P. acnes* bacterial strains is selected based on its ability to produce trans-10, cis-12 linoleic acid. In some embodiments, one or more of the *P. acnes* bacterial strains is selected based on the amount of trans-10, cis-12 linoleic acid it produces in its natural environment. In some embodiments, one or more of the *P. acnes* bacterial strains is selected based on the maximum concentration of trans-10, cis-12 linoleic acid it produces. In some embodiments, one or more of the *P. acnes* bacterial strains is selected based on the activity of the enzyme linoleic acid isomerase it produces. In some embodiments, a *P. acnes* strain with no linoleic acid activity is selected. In other embodiments, a *P. acnes* strain with low levels of linoleic acid activity is selected. In other embodiments, a *P. acnes* strain with high levels of linoleic acid activity is selected.

In some embodiments, production of trans-10, cis-12 linoleic acid by *P. acnes* strains is detected using methods described in and incorporated by reference from U.S. Pat. No. 6,743,609, entitled "Linoleate isomerase," which granted on Jun. 1, 2004. In some embodiments, the amount of trans-10, cis-12 linoleic acid produced is detected using FAME (Fatty acid methyl esters) and/or GC (Gas Chromatography).

In some embodiments, a *P. acnes* strain can convert from 500 pm linoleic acid up to 250 ppm trans-10, cis-12 linoleic acid and then can keep this concentration constant. In some embodiments, a *P. acnes* strain is selected that has higher capacity for conversion of linoleic acid to trans-10, cis-12 linoleic acid. In other embodiments, a *P. acnes* strain is selected that has lower capacity for conversion of linoleic acid to trans-10, cis-12 linoleic acid.

Without wishing to be bound by any theory, in some embodiments, a bacterial composition in which the *P. acnes* strains have zero to low levels of linoleic acid isomerase may be beneficial for preventing or treating acne because such compositions may reduce sebum secretion. In some embodiments, such a composition may be helpful in avoiding relapse of acne after finishing standard acne treatment (such as disinfection or antibiotics).

In some embodiments, bacterial compositions can be used to increase levels of trans-10, cis-12 linoleic acid in the skin follicles. In other embodiments, bacterial compositions can be used to decrease levels of trans-10, cis-12 linoleic acid in the skin follicles. In some embodiments, a combination of *P. acnes* strains is used to deliver trans-10, cis-12 linoleic acid directly to the sebaceous glands either for cosmetic or medical purposes.

In some embodiments, a bacterial composition described herein is used to reduce sebum production on skin that has high levels of sebum production, such as oily skin. In other embodiments, a bacterial composition described herein is used to increase sebum production on skin that has low levels of sebum production, such as dry skin. In some embodiments, a combination of strains with high linoleic acid isomerase activity is applied to the skin of individuals who lack sufficient sebum production. In some embodiments, such individuals are elderly people who may experience a decrease in sebum production.

In some embodiments, the amount of trans-10, cis-12 linoleic acid produced by a *P. acnes* strain is evaluated by comparing production of trans-10, cis-12 linoleic acid in the strain being tested to a *P. acnes* strain that is known not to produce trans-10, cis-12 linoleic acid or that produces negligible or lower than average amounts of trans-10, cis-12 linoleic acid. In other embodiments, the amount of trans-10, cis-12 linoleic acid produced by a *P. acnes* strain is evaluated by comparing production of trans-10, cis-12 linoleic acid in the strain being tested to a *P. acnes* strain that is known to produce average or higher than average amounts of trans-10, cis-12 linoleic acid. In some embodiments, the relative amount of trans-10, cis-12 linoleic acid produced is measured or evaluated. In other embodiments, the absolute amount of trans-10, cis-12 linoleic acid produced is measured or evaluated.

In some embodiments, the amount of cis-9, cis-12 linoleic acid degraded by a *P. acnes* strain is evaluated by comparing the degradation rate of cis-9, cis-12 linoleic acid in the strain being tested to a *P. acnes* strain that is known not to degrade cis-9, cis-12 linoleic acid or that degrades negligible or lower than average amounts of cis-9, cis-12 linoleic acid. In other embodiments, the amount of cis-9, cis-12 linoleic acid degraded by a *P. acnes* strain is evaluated by comparing degradation rate of cis-9, cis-12 linoleic acid in the strain being tested to a *P. acnes* strain that is known to have an average or higher degradation rate than average of cis-9, cis-12 linoleic acid. In some embodiments, the relative amount of cis-9, cis-12 linoleic acid degraded is measured or evaluated. In other embodiments, the absolute amount of cis-9, cis-12 linoleic acid degraded is measured or evaluated.

In some embodiments, one or more of the *P. acnes* bacterial strains within the composition exhibits slow or negligible degradation or conversion of cis-9, cis-12 linoleic acid. In some embodiments, all of the *P. acnes* bacterial strains within the composition exhibit slow or negligible degradation or conversion of cis-9, cis-12 linoleic acid.

In some embodiments, one or more of the *P. acnes* bacterial strains within the composition is selected based on its slow or negligible degradation or conversion of cis-9, cis-12 linoleic acid. In some embodiments, one or more of the *P. acnes* bacterial strains within the composition is selected based on the amount of cis-9, cis-12 linoleic acid it degrades in its natural environment. In some embodiments, one or more of the *P. acnes* bacterial strains within the composition is selected based on the maximum concentration of cis-9, cis-12 linoleic acid it degrades.

In some embodiments, one or more of the *P. acnes* bacterial strains within the composition is genetically modified to degrade less cis-9, cis-12 linoleic acid or to degrade cis-9, cis-12 linoleic acid more slowly.

Individual and combinations of strains can be tested using routine methods to determine which combinations lead to stable compositions. In some embodiments, such compositions are stable at room temperature for at least 1 week, 2, weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or more than 30 weeks. In some embodiments, such compositions are stable at room temperature for at least 1 month, 2 months, 3 months, 4 months, 5 months, 6 months or more than 6 months.

In some embodiments, compositions are stable when refrigerated, at approximately 4° C. for at least 1 week, 2, weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or more than 30 weeks. In some embodiments, compositions are stable when refrigerated, at approximately 4° C. for at least 1 month, 2 months, 3 months, 4 months, 5 months, 6 months or more than 6 months.

In some embodiments, a bacterial composition is formulated by taking a sample from the skin microbiome of a donor subject. For example, the sample can be taken from a subject who does not have acne. In other embodiments, a sample is taken from a subject who has mild, moderate or severe acne. In some embodiments, the sample is taken from a subject who has acne or is susceptible to acne, but bacterial strains associated with causing acne are removed from the sample. A sample can be cultured and can optionally be combined with other components to form a bacterial composition. In other embodiments, a bacterial composition can be formed from one or more isolated bacterial strains.

A sample taken from a donor subject can be tested to see if it contains non-pathogenic *P. acnes* strains. In some embodiments, one or more non-pathogenic *P. acnes* strains from the skin of a donor subject are selected and are administered to a recipient subject. The recipient subject can be the same subject as the donor subject or can be a different subject from the donor subject.

In some embodiments, a bacterial composition can include one or more strains of other bacteria, such as other non-pathogenic bacteria, in addition to one or more strains of *P. acnes*. In some embodiments, the one or more strains of other non-pathogenic bacteria have antibiotic properties. In some embodiments, a bacterial composition can include one or more *S. epidermidis* strains.

In some embodiments, a *P. acnes* strain described herein comprises a sequence selected from SEQ ID NOs: 1-76. In some embodiments, a *P. acnes* strain described herein comprises a sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a sequence selected from SEQ ID NOs: 1-76.

In some embodiments, a composition comprises a *P. acnes* strain that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:27 and/or a *P. acnes* strain that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:64. In some embodiments, a composition comprises a *P. acnes* strain that comprises SEQ ID NO:27 and/or a *P. acnes* strain that comprises SEQ ID NO:64.

In some embodiments, a composition described herein does not include a ribotype 6 (RT6) strain of *P. acnes*. In some embodiments, a composition described herein does not include a Phylotype III strain of *P. acnes*.

TABLE 1

Sequences used to identify *P. acnes* strains by SLST

| SEQ ID NO: | *P. Acnes* Strain | Sequence |
|---|---|---|
| 1 | A1 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 2 | A2 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT |

TABLE 1-continued

Sequences used to identify P. acnes strains by SLST

| SEQ ID NO: | P. Acnes Strain | Sequence |
|---|---|---|
|  |  | TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATTCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 3 | A3 | GTTGCACACCAGGGGGTCAACTTGGCGTCCTCAGTTCAAAATTGATTCAAACTAACAGTTCCAT GTCGGGAAACAGCACCAGGAAGCTCGTGACATATGGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAATAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 4 | A4 | GTTGCACACCAGGGGGTCAACTTGGCGTCCTCAGTTCAAAATTGATTCAAACTAACAGTTCCAT GTCGGGAAACAGCACCAGGAAGCTCGTGACATATGGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 5 | A5 | GTTGCACACCAGGGGGTCAACTTGGCGTCCTCAGTTCAAAATTGATTCAAACTAACAGTTCCAT GCCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 6 | A6 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAT |
| 7 | A7 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGCCATCACGAAGGC CACCACAATCTATCCCAGAACAGCCGGCACTTCACTCACGATGCCCCGATTCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 8 | A8 | GTTGCACACCAGGGGGTCAACTTGGCGTCCTCAGTTCAAAATTGATTCAAACTAACAGTTCCAT GTCGGGAAACAGCACCAGGAAGCTCGTGACATATCGCCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT GTCGCCCTTATTAGGGCAAGCGGTGCCAGTAGCAGAATATGTCACCTCAACAACTCGATCCACC CCTGCCCATTACATGGGTAACATATCCATGGAGGTTCGATGTATACTCGAGGATACAGTCGTCC ATCACGCCCGCCTACATACCCATTACATCAGCATAG |
| 9 | A9 | GTTGCACACCAGGGGGTCAACTTGGCGTCCTCAGTTCAAAATTGATTCAAACTAACAGTTCCAT GCCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCATGAAGGCC ACCACAATCTATCCCAGAACAGCCGGCACTTCACTCACGATGCCCCGATGCTGGATTCCACCC TGCCCATTACATGGGTAACATATCCATGGAGGTTCGATGTATACTCGAGGATACAGTCGTCCA TCACGCCCGCCTACATACCCATTACATCAGCATAG |
| 10 | A10 | GTTGCACACCAGGGGGTCAACTTGGCGTCCTCAGTTCAAAATTGATTCAAACTAACAGTTCCAT GCCGGGAAACAGCACCAGGAAGCTCGTGACATATCGTCTTTCATTGCGAGAAACATCTTACTTA TGTACATTTCTAAGCTATAGCGTCTACCCTTGTCAGACCCAGGACGATGGGTGTCACATCTCCTT TCTAGTCAACCTAAGAGAGGAGGAAATGCCGCGATATATGTTCCACCCTGTCATCACGAAGGC CACCACAATCTATCCCAGAACAGCCGGCACTTCACTCACGATGCCCCGATGCTGGATTCCTATT |

TABLE 1-continued

Sequences used to identify P. acnes strains by SLST

| SEQ ID NO: | P. Acnes Strain | Sequence |
|---|---|---|
|  |  | GTCGCCCTTATTAGGGCAAGCGGTGCCAGTAGCAGAATATGTCACCTCAACAACTCGATCTACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 11 | A11 | GTTGCACACCAGGGGGTCAACTTGGCGTCCTCAGTTCAAAATTGATTCAAACTAACAGTTCCAT<br>GCCGGGAAACAGCACCAGGAAGCCCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 12 | A12 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATATTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 13 | A13 | GTTGCACACCAGGGGGTCAACTTGGCGTCCTCAGTTCAAAATTGATTCAAACTAACAGTTCCAT<br>GTCGGGAAACAGCACCAGGAAGCTGGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 14 | A14 | GTTGCACACCAGGGGGTCAACTTGGCGTTTTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 15 | A15 | GTTGCACACCAGGGGGTCAACTTGGCGTCCTCAGTTCAAAATTGATTCAAACTAACAGTTCCAT<br>GCCGGGAAACAGTACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 16 | A16 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATCCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 17 | A17 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCGGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 18 | A18 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGCCACCTCAACAACTCGATCCACC |

TABLE 1-continued

Sequences used to identify P. acnes strains by SLST

| SEQ ID NO: | P. Acnes Strain | Sequence |
|---|---|---|
| | | CCTGCCCATTACATGGGTAACATATCCATGGAGGTTCGATGTATACTCGAGGATACAGTCGTCC<br>ATCACGCCCGCCTACATACCCATTACATCAGCATAG |
| 19 | A19 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCGACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 20 | A20 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>TTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 21 | A21 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACAATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 22 | A22 | GTTGCACACCAGGGGGTCAACTTGGCGTCCTCAGTTCAAAATTGATTCAAACTAACAGTTCCAT<br>GCCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTGGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 23 | A23 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCCAAGAGAGGAGGAAATGCCGCGATATATGTTCCACCCTGTCATCACGAAGGC<br>CACCACAATCTATCCCAGAACAGCCGGCACTTCACTCACGATGCCCCGATTCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 24 | B1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAGCAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 25 | C1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 26 | C2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCTCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |

TABLE 1-continued

Sequences used to identify *P. acnes* strains by SLST

| SEQ ID NO: | *P. Acnes* Strain | Sequence |
|---|---|---|
| 27 | C3 | GTTGCACACCAGGGGGTCAACTTGGCGTCCTTAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 28 | C4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCTGCATAG |
| 29 | D1 | GTTGCACACCAGGGGGTCAACTTGGCGTCCTCAGTTCAAAATTGATTCAAACTAACAGTTCCAT<br>GTCGGGAAACAGCACCAGGAAACTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCGCCCTGTCATCACGAAGAC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTTGAGGATACAGTCGTCC<br>ATCACGCCCACCTACATACCCATTACATCAGCATAG |
| 30 | D2 | GTTGCACACCAGGGGGTCAACTTGGCGTCCTCAGTTCAAAATTGATTCAAACTAACAGTTCCAT<br>GTCGGGAAACAGCACCAGGAAACTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAACGCCGCGATATATGTTCCGCCCTGTCATCACGAAGAC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTTGAGGATACAGTCGTCC<br>ATCACGCCCACCTACATACCCATTACATCAGCATAG |
| 31 | D3 | GTTGCACACCAGGGGGTCAACTTGGCGTCCTCAGTTCAAAATTGATTCAAACTAACAGTTCCAT<br>GTCGGGAAACAGCACCAGGAAACTCGTGACATATCGTCTTTCATTGCGAGAAACATCTTACTTA<br>TGTACATTTCTAAGCTATAGCGTCTACCTTTGTCAGACCCAGGACGATGGGTGTCACATCCCCTT<br>TCTAGTCAACCTAAGAGAGGAGGAAATGCCGCGATATATGTTCCGCCCTGTCATCACGAAGAC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTTGAGGATACAGTCGTCC<br>ATCACGCCCACCTACATACCCATTACATCAGCATAG |
| 32 | E1 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGAATACAGTCGTCC<br>ATCACGCCCGCCTACATACCCATTACATCAGCATAG |
| 33 | E2 | GTTGCACACCAGGGGGTCAACTTGGCGTCCTCAGTTCAAAATTGATTTAAACTAACAGTTCCAT<br>GTCGGGAAACAGCACCAGAAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 34 | E3 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |

TABLE 1-continued

Sequences used to identify *P. acnes* strains by SLST

| SEQ ID NO: | *P. Acnes* Strain | Sequence |
|---|---|---|
| 35 | E4 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGAAGGTTCGATGTATATTCGAGGATACAGTCGTCC<br>ATCACGCCCGCCTACATACCCATTACATCAGCATAG |
| 36 | E5 | GTTGCACACCAGGGGGTCAACTTGGCGTCCTCAGTTCAAAATTGATTTAAACTAACAGTTTCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 37 | E6 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATTCCGCGATATATGTTCCACCCTGTCATCACGAAGGCC<br>ACCACAATCTATCCCAGAACAGCCGGCACCTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATATTCGAGGATACAGTCGTCCA<br>TCACGCCCGCCTACATACCCATTACATCAGCATAG |
| 38 | E7 | GTTGCACACCAGAGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 39 | E8 | GTTGCACACCAGGGGGTCAACTTGGCGTCCTCAGTTCAAAATTGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCGCCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 40 | E9 | GTTGCACACCAGGGGGTCAACTTGGCGTCCTCAGTTCAAAATAGATTTAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACCTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 41 | F1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 42 | F2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACACCAGCATAG |
| 43 | F3 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA |

TABLE 1-continued

Sequences used to identify P. acnes strains by SLST

| SEQ ID NO: | P. Acnes Strain | Sequence |
|---|---|---|
|  |  | TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTAAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 44 | F4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 45 | F5 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTAGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 46 | F6 | GTTACACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 47 | F7 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTATATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATTCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCAAGCCCGCCTACATACCCATTACATCAGCATAG |
| 48 | F8 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 49 | F9 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC<br>ACCACAATCTATCCCAGAACAGCCGGCACTTCACTCACGATGCCCCGATGCTGGATTCCTATTG<br>TCGCCCTTATTAGGGCAAGCGATGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 50 | F10 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATAGCGTCTACCCTTGTCAGACCCAGGACGATGGGTGTCACACCCCCT<br>TTCTAGTCAACCTAAGAGAGGAGGAAATGCCGCGATATATGTTCCACCCTGTCATCACGAACGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATACTCGAGGATACAGTCGTCC<br>ATCACGCCCGCCTACATACCCATTACATCAGCATAG |
| 51 | G1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGCCTTTCATTGCGAGAAACATCTTACTTA<br>TGTACATTTCTAAGCTATAGCGTCTACCCTTGTCAGACCCAGGACGATGGGTGTCACATCCCCTT<br>TCTAGTCAACCTAAGAGAGGAGGAAATGCCGCGATATATGTTCCACCCTGTCATCACGAACGCC |

TABLE 1-continued

Sequences used to identify P. acnes strains by SLST

| SEQ ID NO: | P. Acnes Strain | Sequence |
|---|---|---|
| | | ACCACAATCGATCCCAGAACAGCCGGCACTTCACTCACGATGCCCCGATGCTGGATTCCTATTG<br>TCGCCCTTATTAGGGCAAGCGGTGCCAGTAGCAGAATATGTCACCTCAACAACTCGATCCACCC<br>CTGCCCATTACATGGGTAACATATCCATGGAGGTTCGATGTATACTCGAGGATACAGTCGTCCA<br>TCACGCCCGCCTACATACCCATTACATCAGCATAG |
| 52 | H1 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 53 | H2 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTCATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 54 | H3 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCCACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 55 | H4 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCGGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 56 | H5 | GTTGCACACCAGGGGGTCAACTTGGCGTCCTCAGTTCAAAATTGATTCAAACTAACAGTTCCAT<br>GTCGGGAAACAGCACCAGGAAGCTCGTGACATATCGTCTTTCATTGCGAGAAACATCTTACTTA<br>TGTACATTTCTAAGCTATATCGTCTACCCTTGTCAGACCCAGGACGATGGATGTCACATCCCCTT<br>TCTAGTCAACCTAAGAGAGGAGGAAATGCCGCGATATATGTTCCACCCTGTCATCACGAAGGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAACAACTCGATCCACC<br>CCTGCCCATTACATGGGTAACATATCCATGGAGGTTCGATGTATATTCGAGGATACAGTCGTCC<br>ATCACGCCCGCCTACATACCCATTACATCAGCATAG |
| 57 | K1 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 58 | K2 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 59 | K3 | GTTGCACACCAGGGGGTCAACTTGGTGTCCTCAGTTCAAAATTGATTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATATGTCTACCCCTGTCAGACCCAGGACGATGGGTGTCATATCCCTTT<br>CCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC |

TABLE 1-continued

Sequences used to identify P. acnes strains by SLST

| SEQ ID NO: | P. Acnes Strain | Sequence |
|---|---|---|
| | | TGCCCATTACATGGGTAACATATCCATGGAGGTACGATGTATGCATCGAGGATGCAGTCGTCTA CTATGCCCGCCTACATACCCATTCCATCAGCATAG |
| 60 | K4 | GTTGCACACCAGGGGGTCAACTTGGTGTCCTCAGTTCAAAATTGATTCAAACTAACGGTTCCGT GTCGGGAAACAGCACCAGAAAACTCGTAACATATCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 61 | K5 | GTTGCACACCAGGGGGTCAACTTGGTGTCCTCAGTTCAAAATTGATTCAAACTAACGGTTCCGT GTCGGGAAACAGCACCAGAAAACTCGTGACATATCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCTCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 62 | K6 | GTTGCACACCAGGGGGTCAACTTGGTGTCCTCAGTTCAAAATTGATTCAAACTAACGGTTCCGT GTCGGGAAACAGCACCAGAAAACTCGTGACATATCGTCTTTCATTGCGAGAAACATCTTATTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 63 | K7 | GTTGCACACCAGGGGGTCAACTTGGTGTCCTCAGTTCAAAATTGATTCAAACTAACGGTTCCGT GTCGGGAAACAGCACCAGAAAACTCGTGACATATCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGAAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGTTAACATATCCATGGAGGTACGATGTATGCATCGAGGATGCAGTCGTCTA CTATGCCCGCCTACATACCCATTCCATCAGCATAG |
| 64 | K8 | ATTGCACACCAGGGGGTCAACTTGGTGTCCTCAGTTCAAAATTGGTTCAAACTAACGGTTCCGT GTCGGGAAACAGCACCAGAAAACTCGTGACATATCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 65 | K9 | GTTGCACACCAGGGGGTCAACTTGGTGTCCTCAGTTCAAAATTGGTTCAAACTAACGGTTCCGT GTCGGGAAACAGCACCAGAAAACTCGTGACATATCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATGGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 66 | K10 | GTTGCACACCAGGGGGTCAACTTGGTGTCCTCAGTTCAAAATTGATTCAAACTAACGGTTCCGT GTCGGGAAACAGCACCAGAAAACTCGTGACATATCATCTTTCATTGCGAGAAACATCTTACTTA TACACATTTCTAAGCTATATGTCTACCCCTGTCAGACCCAGGACGATGGGTGTCATATCCCCTTT CCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |
| 67 | K11 | GTTGCACACCAGGGGGTCAACTTGGTGTCCTCAGTTCAAAATTGATTCAAACTAACGGTTCCGT GTCGGGAAACAGCACCAGAAAACTCGTGACATGTCGTCTTTCATTGCGAGAAACATCTTACTTA TACACATTTCTAAGCTATATTGTCTACCCCTGTCAGACCCAGGACGATGGGTGTCATATCCCCTT TCCAGTCAACCTAAGAAGGGAGGAAATGCCGCGATATATGTTCCGCCCTGTCATCATGAATGCC ACCACAATCTATCCCGGAACAGCCGTACTTCACCCACCATGCCCCGATGCTGGATTCCTATTGT CGCCCTTATTAGAGCAAGCGGTGCCAGCAGCAGAATATTTCACCTCAGCAACTCGATCCGCTCC TGCCCATTACATGGGTAACATATCCATGGAGGTACGATGTATGCATCGAGGATGCAGTCGTCTA CTATGCCCGCCTACATACCCATTCCATCAGCATAG |

TABLE 1-continued

Sequences used to identify P. acnes strains by SLST

| SEQ ID NO: | P. Acnes Strain | Sequence |
|---|---|---|
| 68 | K12 | GTTGCACACCAGGGGGTCAACTTGGTGTCCTCAGTTCAAAATTGGTTCAAACTAACGGTTCCGT<br>GTCGGGAAACAGCACCAGAAAACTCGTGACATATCGTCTTTCATTGCGAGAAACATCTTACTTA<br>TACACATTTCTAAGCTATACTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 69 | K13 | GTTGCACACCAGGGGGTCAACTTGGTGTCCTCAGTTCAAAATTGGTTCAAACTAACGGTTCCGT<br>GTCGGGAAACAGCACCAGAAAACTTGTGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 70 | K14 | GTTGCACACCAGGGGGTCAACTTGGTGTCCTCAGTTCAAAATTGGTTCAAACTAACGGTTCCGT<br>GTCGGGAAACAGCACCAGAAAACTCATGACATATCGTCTTTCATTGCGAGAAACATCTTACTTA<br>TACACATTTCTAAGCTATATTGTCTACCCCTGTCAGACCCAGGACGATGGGTGTCATATCCCCTT<br>TCCAGTCAACCTAAGAAGGGAGGAAATGCCGCGATATATGTTCCGCCCTGTCATCATGAATGCC<br>ACCACAATCTATCCCGGAACAGCCGTACTTCACCCACCATGCCCCGATGCTGGATTCCTATTGT<br>CGCCCTTATTAGAGCAAGCGGTGCCAGCAGCAGAATATTTCACCTCAGCAACTCGATCCGCTCC<br>TGCCCATTACATGGGTAACATATCCATGGAGGTACGATGTATGCATCGAGGATGCAGTCGTCTA<br>CTATGCCCGCCTACATACCCATTCCATCAGCATAG |
| 71 | L1 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |
| 72 | L2 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGCCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |
| 73 | L3 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATATCGTCTACCCTTGCCAGACCCAGGACGATGAGTGTCACATCCCCTT<br>TCCAGTCAACCTAAGAGAGGAGGAAATGCCGCGATATATGCTCCGCCCTGTCATCACGAAAGC<br>CACCACAATCTATCCCAGAACAGCCGGCACTTCACTCACGATGCCCCGATGCTGGATTCCTATT<br>GTCGCCCTTATTAGGGCAAGCGGTGCCAGTAGCAGAATATGTCACCTCAGCAACTCGATCCGCC<br>CCTGCCCATTACATGGGTAACATATCCATGGAGGTTCGATGTATACTCGAGGATACAGTCGCCC<br>ATCACGCCAGCCTACATACCCATTACATCAGCATAG |
| 74 | L4 | GTTGCACACCAGGGGGTCAACTTGGTGTCCTCAGTTCAAAATTGATTCAAACTAACGGTTCCGT<br>GTCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGTTAACATATCCATGGAGGTTCGATGTATACTCGAGGATACAGTCGCC<br>CATCACGCCAGCCTACATACCCATTACATCAGCATAG |
| 75 | L5 | GTTGCACACCAGGGGGTCAACTTGGTGTCCTCAGTTCAAAATTGATTCAAACTAACGGTTCCGT<br>GTCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCTGCCCATTACATGGGTAACATATCCATGGAGGTTCGATGTATACTCGAGGATACAGTCGCC<br>CATCACGCCAGCCTACATACCCATTACATCAGCATAG |

TABLE 1-continued

Sequences used to identify P. acnes strains by SLST

| SEQ ID NO: | P. Acnes Strain | Sequence |
|---|---|---|
| 76 | L6 | GTTGCACACCAGGGGGTCAACTTGGTGTCCTCAGTTCAAAATTGATTCAAACTAACGGTTCCGT<br>ATCGGGAAACAGCACCAGAAAACTCGGGACATATCGTCTTTCATTGCGAGAAAAATCTTACTTA<br>TGCGCATTTCTAAGCTATAGCGTCTACCCTTGTCAGACCCAGGACGATGAGTGTCACATCCCCT<br>TTCCAGTCAACCTAAGAGAGGAGGAAATGCCGCGATATATGCTCCGCCCTGTCATCACGAAAG<br>CCACCACAATCTATCCCAGAACAGCCGGCACTTCACTCACGATGCCCCGATGCTGGATTCCTAT<br>TGTCGCCCTTATTAGGGCAAGCGGTGCCAGTAGCAGAATATGTCACCTCAGCAACTCGATCCGC<br>CCCCGCCCATTACATGGGTAACATATCCATGGAGGTTCGATGTATACTCGAGGATACAGTCGCC<br>CATCACGCCAGCCTACATACCCATTACATCAGCATAG |

TABLE 2

Primer sequences used to type bacterial colonies

| SEQ ID NO: | Description | Sequence |
|---|---|---|
| 77 | Forward primer | CAGCGGCGCTGCTAAGAACTT |
| 78 | Reverse primer | CCGGCTGGCAAATGAGGCAT |
| 79 | SLST-Adapter-FW | TCGTCGGCAGCGTCAGATGTGTATAAGAGACAGCAGCGGCGCTGCTAAGAACTT |
| 80 | SLST-Adapter-RV | GTCTCGTGGGCTCGGAGATGTGTATAAGAGACAGCCGGCTGGCAAATGAGGCAT |

Linoleic Acid and its Isomer Trans-10, Cis-12 Linoleic Acid

Linoleic acid is a C18 fatty acid with two unsaturated double bonds. Usually, the main isomer is cis-9, cis-12. This isomer is also secreted as free fatty acid in the sebum. In vitro, linoleic acid stimulates the lipid production in sebocytes and may be involved in a feedback loop regulating sebum production. It also has antibacterial properties, with different P. acnes strains exhibiting different susceptibility to linoleic acid (Hong Lioe Ko et al., 1978; Madli Puhvel and Reisner, 1970). However linoleic acid also serves as a stimulant for sebum production, which represents the food source of P. acnes. Without wishing to be bound by any theory, an equilibrium may exist, represented by the linoleic acid concentration in the sebum determined by the bacterial population and the host's sebum production. This equilibrium depends on the degradation/conversion rate of cis, cis-12 linoleic acid by the P. acnes population colonizing the follicle.

Conjugated isomers of linoleic acid, namely cis-9, cis-11 linoleic acid and trans-10, cis-12 linoleic acid, have attracted attention as food supplements (Churruca et al., 2009). Linoleic acid trans-10, cis 12 acts on the PPAR receptor family (peroxisome proliferator-activated receptor) (Moya-Camarena et al., 1999). Activation of PPAR-α activates lipid synthesis in epidermal skin models, including cholesterol (Rivier et al., 2000). It has also been reported that trans-10, cis-12 linoleic acid increases ROS (reactive oxygen species) and has anticancer activity (Pierre et al., 2013).

Staphylococcus epidermidis (S. epidermidis)

S. epidermidis is a Gram-positive bacteria that is a normal component of human skin. S. epidermidis can produce 5 lantibiotics, including: epidermin, Pep5, epicidin 280, epilancin K7, and epidermicin NI01. A lantibiotic refers to an antibiotic-like peptide that contains the non-protein amino acids lanthionin and 3-methyllanthionine (Schnell et al., 1988). Epidermin is highly active against P. acnes (Allgaier et al., 1985). Gotz et al. describe epidermin in further detail. Wang et al. report that S. epidermidis can mediate fermentation of glycerol to inhibit the growth of P. acnes.

Strains of S. epidermidis included in bacterial compositions described herein can be naturally occurring or can be genetically modified. Strains that are genetically modified can be modified by natural mutagenesis and/or by genetic engineering. In some embodiments, the genetic modification of the S. epidermidis strain increases its antibiotic properties. In some aspects a bacterial composition can contain one or more strains of P. acnes and one or more strains of S. epidermidis. The one of more strains of P. acnes can be resistant to the antibiotic properties of the one or more strains of S. epidermidis. In some embodiments, the one or more strains of P. acnes are genetically modified to increase their resistance to antibiotic properties of one or more other bacterial strains, such as one or more strains of S. epidermidis. In some embodiments, the one or more P. acnes strains are modified by natural mutagenesis and/or by genetic engineering to increase their resistance to the antibiotic properties of one or more other bacterial strains.

In some embodiments, compositions comprising one or more live P. acnes bacterial strains described herein can contain one or more of an antibiotic, a disinfectant (e.g., BPO), or salicylic acid. One of ordinary skill in the art would appreciate that any antibiotic or disinfectant may be compatible with certain embodiments of the invention.

Skin Microbiome Transplantation

Aspects of the invention relate to modulation of a skin microbiome, such as by transplantation. Transplantation can occur between one or more subjects. In some embodiments, transplantation occurs in one subject and the same subject is the donor and the recipient. In other embodiments, transplantation occurs between two or more subjects. In some embodiment, there is one donor subject and one recipient subject. In other embodiments, there are multiple donor subjects and/or multiple recipient subjects. Multiple methods of transplantation can be used, resulting in different formulations of a bacterial composition. In some embodiments, a non-modified microbiome is transplanted, meaning that a donor microbiome is isolated, and prepared for delivery to a recipient. In other embodiments, a formulated microbiome is transplanted, meaning that a donor microbiome is isolated, optionally genotyped, and specific strains are selected for a formulation (e.g., strains with specific genotypes). In some embodiments a formulated and gene edited microbiome is transplanted, meaning that a donor microbiome is isolated, genotyped, specific strains are selected, genetic mutants are isolated from the strains, and a formulation is generated.

In some embodiments, methods comprise: obtaining one or more live bacterial strains from the skin of a donor subject, wherein the live bacterial strains are *P acnes* strains; determining whether the one or more live bacterial strains are pathogenic; and administering the one or more live bacterial strains to the skin of a recipient subject in need thereof following administration of a disinfectant or antibiotic to the skin of the subject if the one or more live bacterial strains are not pathogenic. In some embodiments, an assay is conducted to determine whether the one or more live *P acnes* strains are pathogenic. For example, an assay can be conducted to assess how the live bacterial strains convert or degrade cis-9, cis-12 linoleic acid. In some embodiments, one or more of the *P. acnes* bacterial strains within the composition is selected based on its slow or negligible degradation or conversion of cis-9, cis-12 linoleic acid.

Other Skin Conditions

In addition to acne, compositions described herein may be used to treat or prevent other skin conditions such as dandruff, progressive macular hypomelanosis, atopic dermatitis or rosacea.

Dandruff is associated with a disequilibrium in the proportion of the skin microbiome. Dandruff can be experienced chronically or as a result of certain triggers, which can be accompanied by redness and irritation. The main contributors are *Propionibacterium acnes* and *Staphylococcus epidermidis*, and can also include *Malassezia restricta*. With dandruff, there is a lower incidence rate for *P. acnes* in comparison to *Staphylococcus epidermidis* and *Malassezia restricta* (Clavaud et al., 2013; Wang et al., 2015). This indicates that supplementation therapy with *P. acnes* bacteria may be beneficial for a dandruff treatment.

*P. acnes* is known to be involved in progressive macular hypomelanosis, which is a common hypopigmentation mainly on the central parts of the trunk, predominantly in young adults, and especially in women (Westerhof et al., 2004). As it is manifested through white spots on the skin, it is mostly diagnosed in patients with darker skin color. Recently, a report showed that progressive macular hypomelanosis is associated with Clade III of *P. acnes* (Barnard et al., 2016). Compositions described herein contain Clade I and II strains and not Clade III strains. Therefore, compositions described herein may be used to treat or prevent progressive macular hypomelanosis.

Atopic dermatitis (also known as atopic eczema) is associated with flares exhibiting a strong dysbiosis of the skin microbiome. The inflammation results in red, swollen, itchy, and cracked skin. The backs of knees, front of the elbows, hands, and feet are the most affected areas. Emollient treatments have been shown to be effective in the treatment of atopic dermatitis. Patients receiving bacterial compositions herein display a generally improved skin condition. Therefore, compositions described herein may be used to treat or prevent atopic dermatitis.

Rosacea is a skin condition that is characterized by facial redness, small and superficial dilated blood vessels on facial skin, pustules, papules, and swelling. There are four types of rosacea, three of which affect the skin. The disorder can be confused or co-exist with acne vulgaris or seborrheic dermatitis. The presence of rash on the scalp or ears suggests a different or co-existing diagnosis because rosacea is primarily a facial diagnosis, although it may occasionally appear in these other areas. Treating rosacea varies depending on severity and subtypes. Supplementation therapy with *P. acnes* using compositions described herein may be used for treating or preventing rosacea.

Treatment

As used herein, the term treat, treated, or treating when used with respect to a disorder such as acne refers to improving at least one symptom of acne, such as a reduction or improvement of lesions associated with acne. As used herein, preventing acne refers to preventing formation of symptoms of acne such as lesions, and/or preventing at least one symptom of acne from getting worse, such as preventing further lesions or preventing existing lesions from becoming worse.

Aspects of the invention relate to improving the appearance of skin and/or maintaining healthy skin. Further aspects of the invention relate to treating or preventing a condition selected from the group consisting of: acne, oily skin, progressive macular hypomelanosis (Barnard et al., 2016), dandruff, atopic eczema, atopic dermatitis, and rosacea.

Subjects

Compositions described herein can be administered to human or non-human subjects. In some embodiments, a subject is a human or non-human who has acne or is at risk of developing acne. In some embodiments, the subject is a human. In some embodiments, the subject is a domestic animal such as a house pet, such as a cat or a dog. In some embodiments, the subject is a farm animal such as a cow, goat, horse, pig or sheep. It should be appreciated that any animal that has skin could be compatible with aspects of the invention.

In some embodiments, a subject who has acne has inflamed lesions and/or non-inflamed lesions. In some embodiments, subjects with high counts of non-inflamed lesions are selected. In some embodiments, subjects are randomized based on the number of non-inflamed lesions.

Effective Amounts

Compositions described herein can be administered in effective amounts. The term "effective amount" of a composition of the invention refers to the amount necessary or sufficient to realize a desired biologic effect. For example, an effective amount of a composition for treating acne is that amount sufficient to improve at least one symptom of acne, such as a reduction or improvement in lesions. The effective amount for any particular application can vary depending on such factors as the condition being treated, the particular composition being administered, the size of the subject, or the severity of the condition. One of ordinary skill in the art can empirically determine the effective amount of a particular composition of the invention without necessitating undue experimentation.

Compositions

Compositions, including cosmetic or pharmaceutical compositions, for topical administration, include transdermal patches, ointments, lotions, creams, gels, drops, sprays, including aerosol sprays, suppositories, liquids, serums or powders. In some embodiments, the preparation is a two-component dispensing system. In addition, conventional pharmaceutical carriers, aqueous, powder or oily bases, or thickeners may be used in pharmaceutical preparations for topical administration. Examples of such ingredients include various hydroxylated compounds, such as monomeric glycols, e.g., propylene glycol, ethyl alcohol, glycerin and butylene glycol, polymeric moisturizers such as polyglycerylmethacrylate, derivatives of palmitates and stearates, triglycerides of fatty acids, lanolin, vegetable or mineral oils, and waxes.

It was surprisingly found herein that an efficient way to establish nonpathogenic *P. acnes* strains on the skin is within a mixture of multiple strains. Within a mixture of strains, slow-growing strains can be established on the skin. In some embodiments, strains are selected so that the resulting population established on the skin will have low linoleic acid isomerase activity. While in the natural context, new strains are occasionally added to the skin microbiome (Oh et al., 2016), it is unlikely that a population with a high isomerase activity would be replaced by one with a low isomerase activity. The approach described herein (involving the combination of disinfection and inoculation) provides an unnatural replacement of a population with high isomerase activity with a low isomerase activity population.

As disclosed herein, some slow-growing strains, such as the non-pathogenic *P. acnes* K8 strain, were unexpectedly found to grow more efficiently within a mixture of strains and in some embodiments to become the dominant strain within a mixture of strains. Accordingly, in some embodiments, a mixture of different *P. acnes* strains can be used to more efficiently colonize the skin with slow growing strains by mixing them with other faster growing strains.

In some embodiments, compositions include media for stabilizing bacterial count. Media can include pure water, PBS, peptone, and/or a diluted or undiluted version of a suitable growth medium or any combination thereof. In some embodiments, the bacterial composition (e.g., a gel) contains a low percentage of peptone which assists in stabilizing the bacteria. In some embodiments, the percentage of peptone in the bacterial composition is about 0.05% or about 0.1%. The percentage of peptone can range in some embodiments from 0.005%-1%, or from 0.05%-1%. For example, the percentage of peptone can be about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9 or 1.0%. In some embodiments, the percentage of peptone is less than 0.005%. In some embodiments, the percentage of peptone is greater than 1%. In some embodiments, the percentage of peptone is about 0.25%.

In other embodiments, a suitable growth medium is used in place of peptone.

In some embodiments, the source of peptone is from casein, such as trypsin-digested peptone from casein. However, it should be appreciated that any form or source of peptone can be compatible with aspects of the invention. For example, in some embodiments, the peptone is acid-digested, rather than trypsin-digested. In some embodiments the peptone is from meat.

In some embodiments, the composition contains a buffer component to help stabilize the pH. In some embodiments, the pH is between 4.5-8. For example, the pH can be approximately 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, including any value in between. In some embodiments, the pH is approximately 7.0.

Non-limiting examples of buffers can include ACES, acetate, ADA, ammonium hydroxide, AMP (2-amino-2-methyl-1-propanol), AMPD (2-amino-2-methyl-1,3-propanediol), AMPSO, BES, BICINE, bis-tris, BIS-TRIS propane, borate, CABS, cacodylate, CAPS, CAPSO, carbonate (pK1), carbonate (pK2), CHES, citrate (pK1), citrate (pK2), citrate (pK3), DIPSO, EPPS, HEPPS, ethanolamine, formate, glycine (pK1), glycine (pK2), glycylglycine (pK1), glycylglycine (pK2), HEPBS, HEPES, HEPPSO, histidine, hydrazine, imidazole, malate (pK1), malate (pK2), maleate (pK1), maleate (pK2), MES, methylamine, MOBS, MOPS, MOPSO, phosphate (pK1), phosphate (pK2), phosphate (pK3), piperazine (pK1), piperazine (pK2), piperidine, PIPES, POPSO, propionate, pyridine, pyrophosphate, succinate (pK1), succinate (pK2), TABS, TAPS, TAPSO, taurine (AES), TES, tricine, triethanolamine (TEA), and Trizma (tris).

In some embodiments the formulation includes a thickener. Non-limiting examples of thickeners can include hydroxyethylcelluloses (e.g. NATROSOL®), starch, gums such as gum arabic, kaolin or other clays, hydrated aluminum silicate, fumed silica, carboxyvinyl polymer, sodium carboxymethyl cellulose or other cellulose derivatives, ethylene glycol monostearate and sodium alginates.

In some embodiments, the thickener is hydroxyethyl cellulose. In some embodiments, the hydroxyethyl cellulose comprises NATROSOL® hydroxyethylcellulose (HEC) (Ashland Inc.). In some embodiments, the NATROSOL® is NATROSOL® HX (Caesar & Loretz GmbH, order no 4482, CAS: 9004-62-0) or NATROSOL® G (Caesar & Loretz GmbH, order no 4484, CAS: 9004-62-0). It should be appreciated that any form of hydroxyethyl cellulose can be compatible with aspects of the invention. In some embodiments, the viscosity type is HHR-P, HH, H4, H, MH, M, K, G, E or L.

In some embodiments, the concentration of the thickener, such as hydroxyethyl cellulose, is between approximately 1%-5%. For example, the concentration can be about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0%. In other embodiments, the concentration of thickener, such as hydroxyethyl cellulose, is less than 1% or more than 5%. In some embodiments, the concentration of thickener, such as hydroxyethyl cellulose, is approximately 1.5%. In some embodiments, the concentration of thickener, such as hydroxyethyl cellulose, is approximately 2.5%.

In some embodiments, a composition comprises one or more live *P. acnes* strains at colony-forming units (CFU) of at least $10^4$-$10^9$/ml. For example, the CFU can be at least $10^4$, at least $10^5$, at least $10^6$, at least $10^7$, at least $10^8$, at least $10^9$ or more than $10^9$/ml. In some embodiments, all of the *P. acnes* strains are present in a composition at colony-forming units (CFU) of at least $10^4$-$10^9$/ml. In some embodiments, the bacterial composition exhibits a stable CFU over at least three months at room temperature. In some embodiments, the CFU count shortly fluctuates in the initial storage phase (e.g., 2 weeks) and then stabilizes.

In some embodiments, a composition comprises about 2.5% of a thickener, such as NATROSOL® hydroxyethylcellulose (HEC); about 0.25% peptone, such as trypsin-digested peptone from casein; and a CFU of about $10^4$-$10^9$/ml of two or more live *P. acnes* strains (e.g., about $10^7$/ml of each live *P. acnes* strain).

Aspects of the invention relate to compositions comprising mixtures of different live *P. acnes* strains. Mixtures can include two or more strains. In some embodiments, the composition includes at least two different live *P. acnes* strains. The two different strains can be present at equal concentrations or at unequal concentrations. In some embodiments, the composition comprises a 2-strain mixture of *P. acnes* strain C3 and *P. acnes* strain K8. In certain embodiments, both strains are present at equal concentrations. In certain embodiments, both strains are present at a CPU of approximately $5 \times 10^6$/ml.

In some embodiments, the composition comprises at least 4 different live *P. acnes* strains. In certain embodiments, the composition comprises a 4-strain mixture of *P. acnes* strain C3, *P. acnes* strain A5, *P. acnes* strain F4 and *P. acnes* strain K8. The four different strains can be present at equal concentrations or at unequal concentrations. In certain embodiments, the relative concentrations of strains C3, A5, F4, and K8 are approximately 55%, 30%, 10%, and 5%, respectively. In some embodiments the CPU values for strains C3, A5, F4, and K8 are approximately $5.5 \times 10^6$/ml, $5.5 \times 10^6$/ml, $1 \times 10^6$/ml, and $5 \times 10^5$/ml, respectively.

In some embodiments, each live *P. acnes* bacterial strain constitutes at least approximately 5% of the composition.

In some embodiments, the compositions further include salicylic acid. In some embodiments, the compositions include 0.05-10% salicylic acid. For example, the compositions can include approximately 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10% salicylic acid. In other embodiments, compositions include less than 0.05% salicylic acid or more than 10% salicylic acid. In some embodiments, in a composition that is kept on the face for an extended time, the percentage of salicylic acid is less than or equal to 2%. In some embodiments, in a composition that is washed off the face and not kept on the face for an extended time, the percentage of salicylic acid is less than or equal to 3%. *P. acnes* strains are surprisingly not inhibited by salicylic acid, allowing the inclusion of salicylic acid within compositions described herein for treatment of skin conditions (e.g., acne or dandruff).

In some embodiments, the bacterial composition is combined with one or more anti-inflammatory compounds. Without wishing to be bound by any theory, the anti-inflammatory compound may reduce the inflamed lesions in the short term, while the bacterial composition may address the underlying problem and produce a long-term effect.

In some embodiments, compositions comprise emollients such as those disclosed in an incorporated by reference from U.S. Pat. No. 5,525,336. Non-limiting examples of emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polthylene glycol, triethylene glycol, lanolin, sesame oil, coconut oil, arrachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

In some embodiments, a protein stabilizing agent such as those disclosed in an incorporated by reference from U.S. Pat. No. 5,525,336 is included in the composition. Non-limiting examples include glycerol, ethylenediaminetetraacetic acid, cysteine, and proteinase inhibitors such as leupeptin, pepstatin, antipain, and cystatin.

In some embodiments, a humectant such as those disclosed in an incorporated by reference from U.S. Pat. No. 5,525,336 is included in the composition. Non-limiting examples of humectants include glycerin, sorbitol, sodium 2-pyrrolidone-5-carboxylate, soluble collagen, dibutylphthalate, gelatin.

In some embodiments, an astringent agent such as those disclosed in an incorporated by reference from U.S. Pat. No. 5,525,336 is included in the composition. Non-limiting examples of astringent agents include *arnica* flowers or extracts thereof, lower alkyl alcohols, witch hazel, boric acid, lactic acid, methol, camphor, zinc phenol sulphonate, aluminum acetate, aluminum sulfate, and zinc chloride or sulfate.

In some embodiments, a pigment such as those disclosed in an incorporated by reference from U.S. Pat. No. 5,525,336 is included in the composition. Non-limiting examples of pigments include titanium dioxide, micas, iron oxides, barium lake, calcium lake, aluminum lake, bismuth oxychloride, zirconium lake and calcium oxides.

In some embodiments, a coloring agent such as those disclosed in an incorporated by reference from U.S. Pat. No. 5,525,336 is included in the composition. Non-limiting examples of coloring agent include shikonin, (3-carotene, paprika, monascus, safflower red, safflower yellow, red cabbage color, purple sweet potato color, lycopene, cacao color, grape color, cochineal, lac color, beet red, hematein, Red. No. 215, Red. No. 218, Red. No. 223, Red. No. 225, Orange No. 201, Orange No. 206, Yellow No. 201, Green No. 202, and Purple No. 201, Red. No. 2, Red. No. 3, Red. No. 102, Red. No. 104 (1), Red. No. 105 (1), Red. No. 106, Yellow No. 4, Yellow No. 5, Green No. 3, Blue No. 1, Blue No. 2, Red. No. 201, Red. No. 213, Red. No. 214, Red. No. 227, Red. No. 230 (1), Red. No. 230 (2), Red. No. 231, Red. No. 232, Orange No. 205, Orange No. 207, Yellow No. 202 (1), Yellow No. 202 (2), Yellow No. 203, Green No. 201, Green No. 204, Green No. 205, Blue No. 202, Blue No. 203, Blue No. 205, and Brown No. 201.

In some embodiments, UV-A and UV-B radiation filters, sunscreens, free-radical blockers, vitamin extracts, or antioxidants such as those disclosed in an incorporated by reference from U.S. Pat. No. 5,525,336 are included in compositions.

In some embodiments, a surfactant or a solvent such as those disclosed in an incorporated by reference from U.S. Pat. No. 5,525,336 is included in the composition. Non-limiting examples of solvents include water, ethyl alcohol, toluene, methylene chloride, isopropanol, n-butyl alcohol, castor oil, ethylene glycol monoethyl ether, diethylene glycol monobutyl ether, diethylene glycol monoethyl ether, dimethyl sulphoxide, dimethyl formamide and tetrahydrofuran. i) Anionic surfactants, such as metallic or alkanolamine salts of fatty acids for example sodium laurate and triethanolamine oleate; alkyl benzene sulphones, for example triethanolamine dodecyl benzene sulphonate; alkyl sulphates, for example sodium lauryl sulphate; alkyl ether sulphates, for example sodium lauryl ether sulphate (2 to 8 EO); sulphosuccinates, for example sodium dioctyl sulphonsuccinate; monoglyceride sulphates, for example sodium glyceryl monostearate monosulphate; isothionates, for example sodium isothionate; methyl taurides, for example Igepon T; acylsarcosinates, for example sodium myristyl sarcosinate; acyl peptides, for example Maypons and lamepons; acyl lactylates, polyalkoxylated ether glycollates, for example trideceth-7 carboxylic acid; phosphates, for example sodium dilauryl phosphate; Cationic surfactants, such as amine salts, for example sapamin hydrochloride;

quartenary ammonium salts, for example Quaternium 5, Quaternium 31 and Quaternium 18; Amphoteric surfactants, such as imidazol compounds, for example Miranol; N-alkyl amino acids, such as sodium cocaminopropionate and asparagine derivatives; betaines, for example cocamidopropylebetaine; Nonionic surfactants, such as fatty acid alkanolamides, for example oleic ethanolamide; esters or polyalcohols, for example Span; polyglycerol esters, for example that esterified with fatty acids and one or several OH groups; Polyalkoxylated derivatives, for example polyoxy:polyoxyethylene stearate; ethers, for example polyoxyethe lauryl ether; ester ethers, for example Tween; amine oxides, for example coconut and dodecyl dimethyl amine oxides. In some embodiments, more than one surfactant or solvent is included.

In some embodiments, preservatives, antiseptics, pigments or colorants, fragrances, masking agents, and carriers, such as water and lower alkyl, alcohols, such as those disclosed in an incorporated by reference from U.S. Pat. No. 5,525,336 are included in compositions.

In some embodiments wherein a composition is in a powder, the powders may include chalk, talc, fullers earth, colloidal silicon dioxide, sodium polyacrylate, tetra alkyl and/or trialkyl aryl ammonium smectites and chemically modified magnesium aluminum silicate as disclosed in an incorporated by reference from U.S. Pat. No. 5,525,336. In some embodiments, a composition can include a perfume.

When administered, the compositions of the invention are applied in a therapeutically effective, pharmaceutically acceptable amount as a pharmaceutically acceptable formulation. Any of the compositions of the present invention may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation.

In some embodiments, one or more of the following agents is included in compositions described herein: topical antibiotics (e.g., clindamycin, erythromycin, tetracycline, metronidazole), oral antibiotics (e.g., tetracycline, erythromycin, minocycline, doxycycline, clindamycin), topical retinoids (e.g., adapalene, tazarotene, tretinoin), oral retinoids (e.g., isotretinoin), benzoyl peroxide, salicylic acid, sulfur, azelaic acid, and antimicrobial peptides and derivatives thereof (e.g., lipohexapeptide HB1345, oligopeptide-10, magainins (e.g., pexiganan), protegrins (e.g., iseganan), indolicidins (e.g., omiganan, MBI 594AN), histatins (e.g., P113 P113D), human bactericidal/permeability-increasing proteins (e.g., XMP.629, neuprex), cathelicidins (e.g., cathelicidin-BF).

In some embodiments, compositions are administered in a topical form, such as in a cream or ointment. In some embodiments, administration of compositions described herein comprises part of a combination treatment or follows from an earlier treatment of the skin of a subject.

The appropriate amount of a composition to be applied can depend on many different factors and can be determined by one of ordinary skill in the art through routine experimentation. Several non-limiting factors that might be considered include biological activity and bioavailability of the agent, nature of the agent, mode of administration, half-life, and characteristics of the subject to be treated.

In some embodiments, the bacterial composition is not applied to subjects with sensitive skin. In some embodiments, when using a bacterial composition for the treatment or prevention of acne, the subject being treated avoids unnecessary sun exposure and uses a sunscreen. In some embodiments, if the treated skin is irritated, characterized by redness, swelling, burning, itching, or peeling, the product is used less frequently or in a lower concentration.

In some embodiments, a composition described herein is administered to the skin of a subject to maintain healthy skin. A composition can be administered once or multiple times. In some embodiments, a composition is administered at regular intervals while in other embodiments it is administered in irregular intervals. For example, a composition can be administered about every 15 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 3 days, 4 days, 5 days, 1 week, 2 weeks, 3 weeks, 4 weeks, 5 weeks, 6 weeks, 7 weeks, 8 weeks or more or less frequently including all values in between.

In some embodiments, a composition is administered to a subject who also receives or has previously received a standard acne treatment, such as a disinfectant or an antibiotic, as would be recognized by one of ordinary skill in the art. In some embodiments, the composition is administered in parallel with the standard acne treatment. In other embodiments, the composition is administered after the standard acne treatment. The composition can be administered either immediately after the previous treatment or there can be a delay between the previous treatment and administration of the composition. The composition can be administered once or multiple times after the previous treatment. In some embodiments, a composition is administered at regular intervals after the previous treatment while in other embodiments it is administered in irregular intervals after the previous treatment. For example, a composition can be administered about every 15 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 3 days, 4 days, 5 days, 1 week, 2 weeks, 3 weeks, 4 weeks, 5 weeks, 6 weeks, 7 weeks, 8 weeks or more or less frequently including all values in between after a previous treatment.

Aspects of the invention encompass mutating bacterial strains, such as in *S. epidermis* strains. Mutations can be made in some embodiments by selecting an amino acid substitution, or by random mutagenesis of a selected site in a nucleic acid or polypeptide. Variant polypeptides can be expressed and tested for one or more activities to determine whether a mutation provides a variant polypeptide with desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or eukaryotic expression vector, introducing the vector into an appropriate host cell, expressing the variant polypeptide, and testing for a functional capability of the polypeptides as disclosed herein.

Bacterial cells according to the invention can be cultured in a variety of media, including rich or minimal media. As would be understood by one of ordinary skill in the art, routine optimization would allow for use of a variety of types of media. Media can be supplemented with various additional components, including sugar sources. Some non-limiting examples of supplemental components include glucose, amino acids, antibiotics and ATCC Trace Mineral Supplement. Similarly, other aspects of the medium, and growth conditions of the cells of the invention can be optimized through routine experimentation. For example, pH, temperature, and concentration of components within the compositions are non-limiting examples of factors which can be optimized.

Liquid and/or solid cultures used to grow cells associated with the invention can be housed in any of the culture vessels known and used in the art.

In some embodiments, the bacterial strains are grown in batches. In some embodiments, the bacterial strains are grown in fermenters. In some embodiments, compositions comprising the bacterial strains are packaged. In certain embodiments, compositions comprising the bacterial strains are packaged in enteral syringes or sachets.

Kits

The present invention also provides any of the above-mentioned compositions in kits. In some embodiments, a kit comprises a container housing live bacteria or a container housing freeze-dried live bacteria. Kits can include a second container including media such as peptone. In some embodiments, kits can include antibiotic(s), disinfectant(s) (e.g., BPO) and/or salicylic acid. In some embodiments, the antibiotic(s), disinfectant(s) and/or salicylic acid are used to pre-treat the skin before application of the composition comprising live bacteria. Kits can also include instructions for administering the composition. In certain embodiments, instructions are provided for mixing the bacterial strains with other components of the composition. In some embodiments, a kit further includes an applicator to apply the bacterial composition to a subject.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Different P. acnes Strains have Different Levels of Linoleic Acid Isomerase Activity or Final Thresholds of Concentration of Trans-10, Cis-12 Linoleic Acid Experiments were performed to characterize the linoleic acid isomerase activity of multiple different P. acnes strains. The P. acnes strains were grown in a growth medium lacking linoleic acid (Rosson et al., 2004). Cis-9, cis-12 linoleic acid was added to the growth medium and then the amount of cis-9, cis-12 and trans-10, cis-12 linoleic acid isomer was determined at different time points, using an assay involving conversion to fatty acid methyl esters and subsequent gas chromatography. Established methods for distinguishing cis and trans isomers of unsaturated fatty acids are described in Kramer et al., 2004, which is herein incorporated by reference in its entirety.

Surprisingly, the choice of media and incubation conditions were found to be important variables for conducting these experiments. To measure the degradation of linoleic acid in the media, reinforced clostridial media (RCM) was used because it was observed that in some other types media, the linoleic acid precipitated.

Results showing degradation of cis-9, cis-12 linoleic acid are shown in FIG. 1. A very rapid decrease of cis-9, cis-12 linoleic acid was observed, with most of the degradation occurring in the first 48 h of the experiment. It was also observed that while strain A1 depletes the linoleic acid completely from the medium, the strain C3 surprisingly slows down in degradation of linoleic acid reaching an equilibrium concentration. Without wishing to be bound by any theory, acne patients usually have a lower linoleic acid concentration in the sebum compared to healthy subjects. Accordingly, a population of slow degrading strains will result in a higher concentration of linoleic acid in sebum, which may be advantageous.

Only small amounts of trans-10, cis-12 linoleic acid isomer were detected in rich media, such as RCM, likely because rich medias such as RCM do not represent the environment encountered in sebaceous glands. In particular, glucose is normally limited in the sebaceous glands and could influence the metabolic program of the bacteria (Im and Hoopes, 1974). All previous commonly used media for P. acnes (e.g., RCM, BHI, GAM) contain at least 3 g/L of glucose, whereas in the sebaceous glands, glucose only occurs at comparably low concentrations (e.g., ~0.6-1.4 g/kg dry weight (Im and Hoopes, 1974)).

Therefore, a glucose-free media in which all P. acnes strains grow was designed herein and used to test and characterize 11 P. acnes strains. A minimal media was established out of peptone and yeast extract (PY-media) which allows the growth of bacteria and the measurement of the production of trans-10, cis-12 linoleic acid isomer since it resembles the natural environment encountered by the bacteria.

Figure 2:
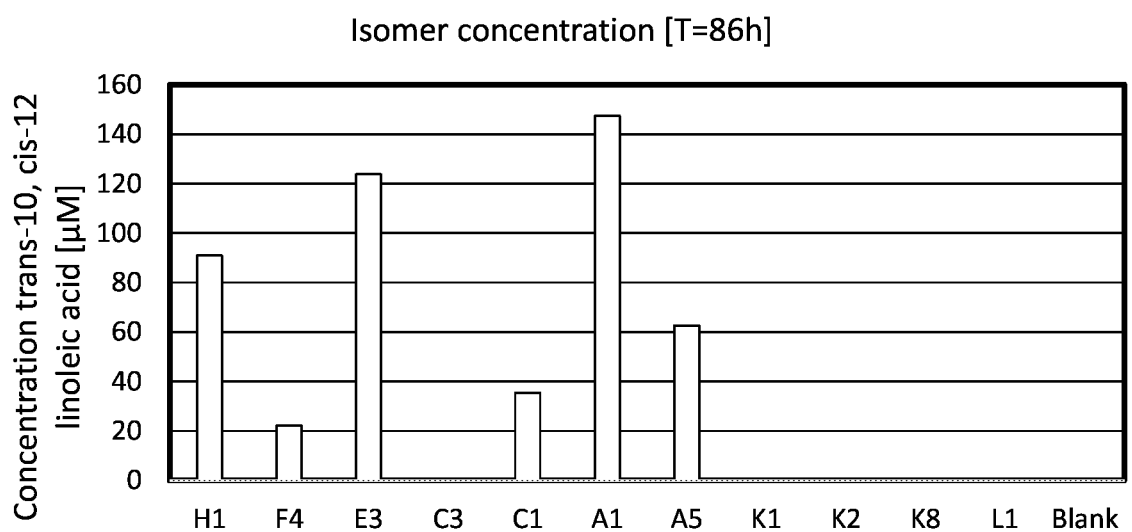
FIG. 2 depicts the concentration of the trans-10, cis-12 linoleic acid isomer after 86 h shaking incubation of different strains in glucose free medium. The concentrations are normalized for growth by OD (600 nm).
Figure 3:
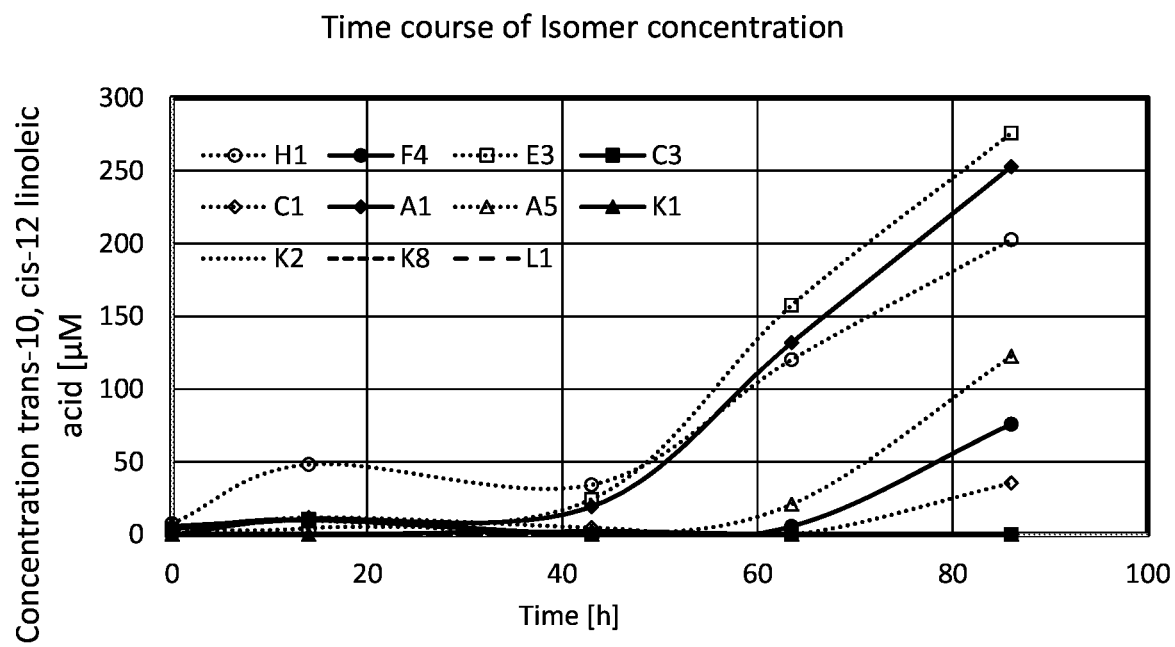
FIG. 3 depicts a time course of isomer concentration in a variety of strains.

Conditions were developed for assessing production of trans-10, cis-12 linoleic acid isomer involving shaking samples in a minimal media. A time course analysis conducted with multiple strains is shown in FIG. 3. As the growth of the individual strains varied, the reading was normalized corrected by the Optical Density (OD) measured at 600 nm, which was confirmed by CFU counts on agar plates. To normalize the OD, the OD of each culture was used as a measure for the biomass of each strain. All OD measurements were then divided by the highest measured value, providing a factor representing relative growth. The measured trans-10, cis-12 linoleic acid concentration was then multiplied with this factor for each strain. The underlying assumption is that a strain that will have grown to high optical density might have still produced less isomerase per cell than a slow growing strain. The corrected concentrations of trans 10, cis 12 linoleic acid isomer is shown in FIG. 2. Strain A1, which is generally associated with acne (McDowell et al., 2012, PLoS ONE 7, e41480), produced the most trans-10, cis-12 linoleic acid isomer. Strains with very little production of trans-10, cis-12 linoleic acid isomer were C3, C1, F4, A5, K1, K2, K8 and L1. The K strains and L1 strain showed very little growth. These strains also grow very slowly in rich media and are rarely occurring in nature. Unexpectedly, as discussed below, in certain combinations with other strains, the K8 strain shows improved growth.

Materials and Methods

Each strain was grown as a pre-culture and the pre-cultures were normalized by OD. A fresh media containing 1.7 mM cis 9, cis 12 linoleic acid was prepared before each experiment. The cultures were then incubated at 37° C. either still or shaking at 220 rpm. The samples were taken at various time points and immediately frozen at −80° C. until the lipid extraction and gas chromatography (GC) analysis.

For the GC analysis, the lipids in the media were extracted and converted to their methyl esters. For this, 100 µl of a media sample was diluted with 900 µl $H_2O$. 20 µg of Heptadecanoic acid was added as an internal standard and the complete lipid fraction was extracted with ethylacetate. The organic phase was then separated and dried under nitrogen. The lipids were then converted with a 14% Borontrifluoride-Methanol solution (Sigma-Aldrich, St. Louis, Mo., catalog number B1252), extracted with hexane, dried under nitrogen and resuspended in 100 µl of hexane. The samples were then analyzed on a Varian CP 3800 Gas chromatograph with FID detector. The column used was a CP-WAX 58 (FFAP) Capillary column 25 m×0.32 mm I.D from Agilent Technologies, Santa Clara, Calif. and the temperature program was 120° C. (1 min)-120° C. to 250° C. (20° C./min)-250° C. (12 min).

Example 2: Optimization of Mixtures of Bacterial Strains

Example 1 demonstrates that isolated *P. acnes* strains differed significantly in their growth behavior. Generally, strains from Clade I were found to be fast growers, while strains from Clade II were found to be slow growers (see, e.g., FIG. 5). In general, strains which are considered not to be associated with acne are more likely to originate from Clade II (Lomholt and Kilian, 2010; Yu et al.). This slow growth indicates that these strains are less likely to colonize the skin after a disinfection. Strains from Clade II are also less commonly found in human subjects. In nature, skin tends to be colonized by fast growing strains from Clade I. By contrast, described herein are mixtures of strains that allow for colonization of the skin by Clade II strains.

Further growth curve experiments showed that mixtures of 2 or 4 strains grow similarly as fast as the fastest pure isolates in the mixtures. Surprisingly, when compositions of mixtures consisting of 6 strains grown for 5 days on agar were analyzed, the majority of the bacteria was found to originate from the strain K8 (FIG. 7), which was a strain that was observed to grow slowly when grown individually. Accordingly, mixtures of strains can be created which have advantageous growth properties even though they contain individual strains that grow slowly in nature and would likely be outcompeted in nature.

Strains within Clade IA1 have been reported to be associated with acne vulgaris (Lomholt and Kilian, 2010, PLoS One 5; McDowell et al., 2012, PLoS ONE 7, e41480). To select strains from Clade IA1 to mix with strains from Clade II to co-colonize the skin, the criteria of conversion of cis 9, cis 12 linoleic acid to the trans 10, cis 12 isomer was used for strain selection. Colonization of the skin with such a mixture of strains is unlikely to occur naturally in part because the increased use of cosmetics with preservatives and hygienic products leads to natural selection of fast growing strains, which become the dominant occupants on the skin. Accordingly, in a naturally occurring transfer of *P. acnes* strains (e.g., by close body contact), the vast majority of transferred bacteria would be from only one strain.

Based on both growth behavior and production of trans 10, cis 12 linoleic acid, strain C3 was selected as a strain for colonization to use in the compositions comprising mixtures of bacterial strains. The effect of varying starting concentrations of the composition on the skin was then tested. 6 different strains were mixed in equal amounts and one of the 6 strains was added in excess. After 5 and 6 days of growth, the composition of the mixture was then assessed. Based on this data in conjunction with growth curves, the final concentration of strains in the compositions comprising mixtures of bacterial strains was selected.

A high concentration (e.g., less than or equal to 60%) of a strain from Clade I was added, which exhibited a low conversion rate of cis 9, cis 12 linoleic acid, grew to medium high ODs and showed a decrease in relative amount of the mixture from day 5 to day 6.

A mixture was prepared in which a given strain maximally represents 50% of the population. In nature, most of the time one *P. acnes* strains likely represents more than 90% of the observed *P. acnes* population on one host.

It was observed that the growth behavior of *P. acnes* is for some strains heavily dependent on the starting CFU count. Therefore, it was investigated how the relative proportion of one strain in a mixture develops once the culture has reached a stationary phase. Surprisingly, it was found that the underlying dynamics by which a strain becomes a dominant strain is determined at least in part by the starting amount of bacteria and varies from strain to strain.

Pre-cultures were grown in RCM media and, after centrifugation, were resuspended in PBS. The cultures were normalized to OD 0.5. Then 1 ml of medium was inoculated with 50 µl of the normalized suspension. The plates were airtight sealed and the cultures were then incubated at 37° C. in a Tecan Spark. The cultures were shaken every 30 min and the OD at 600 nm was measured. RCM media was obtained from BD (BD/Difco catalog no. 218081). PY media is a custom media, which only consists of 2% yeast extract (Sigma catalog number Y1625-250G) and 3% peptone (Sigma 70172-500G). This media contains no glucose and thereby more accurately reflects the low glucose environment encountered by *P. acnes* in the sebaceous glands than rich media with a high glucose content like RCM or BHI.

Figure 4:
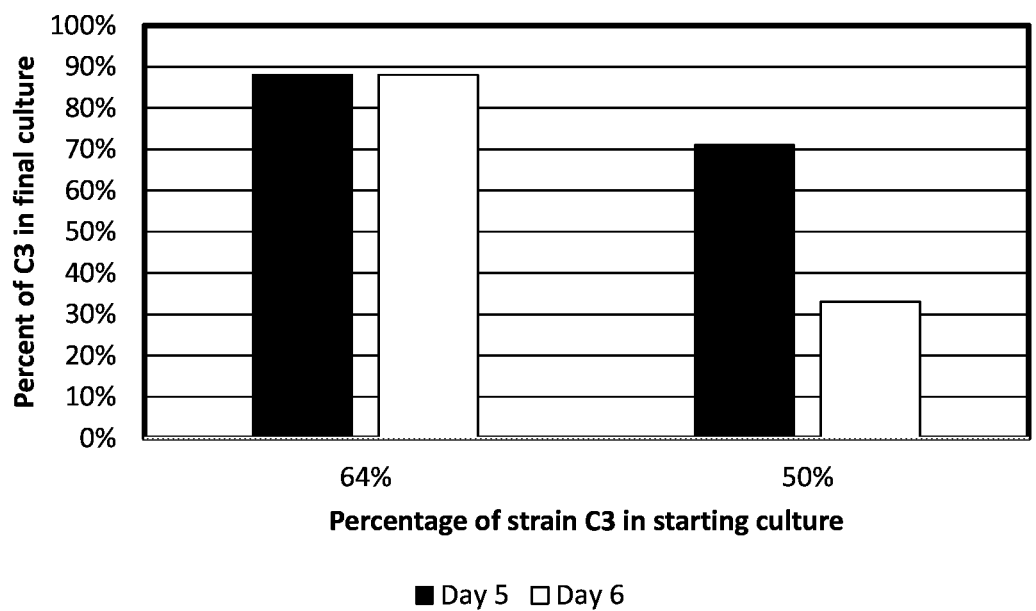
FIG. 4 depicts the relative amount of C3 strain in a mixture at day 5 or day 6 after inoculation. When present at a high percentage in the starting mixture, C3 stays the dominant strain. Surprisingly, when present at lower starting concentration, the overall percentage of C3 is reduced in the late stationary phase.

FIG. 4 shows the relative amount of C3 strain in a mixture at day 5 or day 6 after inoculation. When there is a high percentage of C3 in the starting mixture, C3 stays the dominant strain. Surprisingly, a lower starting concentration of C3 reduces the overall percentage in the late stationary phase.

Figure 5:
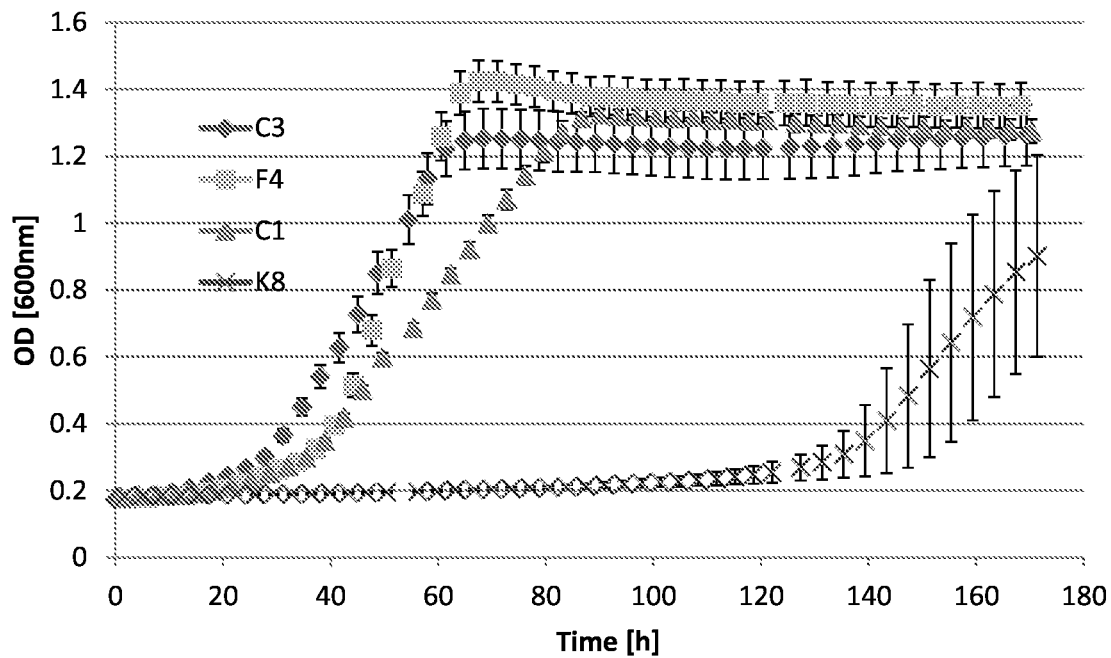
FIG. 5 depicts a growth curve of the strains C3, F4, C1 and K8 in RCM media at 37° C.

FIG. 5 shows a growth curve of the strains C3, F4, C1 and K8 in RCM media at 37° C.

Figure 6:
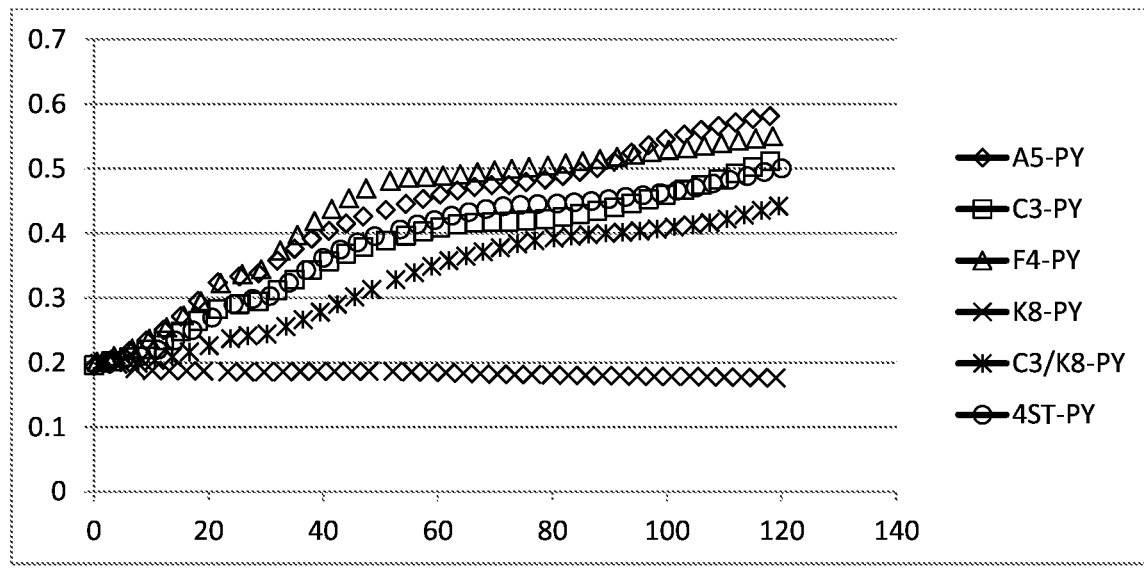
FIG. 6 depicts a growth curve of the strains C3, F4, C1, K8, a 2-strain mixture (C3 and K8) and a 4-strain mixture (A5, C3, F4, and K8) in glucose free PY media at 37° C.

FIG. 6 shows a growth curve of the strains C3, F4, C1, K8, a 2-strain mixture (strains C3 and K8) and a 4-strain mixture (A5, C3, F4, and K8) in glucose-free PY media at 37° C.

Example 3: Competition Experiments with Combinations of Strains

An in vitro experiment was performed to determine the synergistic effect of various bacterial mixtures. Fresh bacterial cultures were revived from −80° C. stocks and were grown on RCM agar plates. From the agar plates, a BHI liquid medium was inoculated and grown for 5 days until stationary phase. Then the cultures were harvested by centrifugation (4000 g for 10 min at 4° C.) and resuspended in 1.4 ml of 0.1% Peptone (trypsin-digested peptone from casein). The bacterial suspensions in peptone were then normalized to an OD of 0.8. The strains were stored overnight at room temperature (RT) in the peptone solution to simulate storage before application. The next morning, all strains were then mixed in equimolar concentrations and this mixture was diluted further 1.6 fold with the peptone solution. Accordingly, each strain was at a 1:10 dilution in the mixture compared to the stock solution. Then a 96-well master plate was generated which contained different combinations (Table 3).

TABLE 3

| | Strains | | |
|---|---|---|---|
| | Dominant strain | Mix | 0.1% Peptone |
| A | 100 µl | 100 µl | 0 µl |
| B | 80 µl | 100 µl | 20 µl |
| C | 60 µl | 100 µl | 40 µl |
| D | 40 µl | 100 µl | 60 µl |
| E | 20 µl | 100 µl | 80 µl |
| F | 10 µl | 100 µl | 90 µl |
| G | 0 µl | 100 µl | 100 µl |
| H | 50 | 0 | 100 µl |

This resulted in the following concentrations (Table 4):

TABLE 4

| | Concentrations | | | | | | | |
|---|---|---|---|---|---|---|---|---|
| | % A5 | % Rest | % C3 | % Rest | % E3 | % Rest | % K8 | % Rest |
| A | 68.8% | 6.3% | 68.8% | 6.3% | 68.8% | 6.3% | 68.8% | 6.3% |
| B | 64.3% | 7.1% | 64.3% | 7.1% | 64.3% | 7.1% | 64.3% | 7.1% |
| C | 58.3% | 8.3% | 58.3% | 8.3% | 58.3% | 8.3% | 58.3% | 8.3% |
| D | 50.0% | 10.0% | 50.0% | 10.0% | 50.0% | 10.0% | 50.0% | 10.0% |
| E | 37.5% | 12.5% | 37.5% | 12.5% | 37.5% | 12.5% | 37.5% | 12.5% |
| F | 28.6% | 14.3% | 28.6% | 14.3% | 28.6% | 14.3% | 28.6% | 14.3% |
| G | 16.0% | 16.0% | 16.0% | 16.0% | 16.0% | 16.0% | 16.0% | 16.0% |
| H | A5 100% | A5 100% | C3- 100% | C3- 100% | E3- 100% | E3- 100% | K8- 100% | K8- 100% |

The 10 µl of each mixture was added in the middle of a 96-well agar plate and incubated for 4 days. The media used was RCM-agar supplemented with 0.5 mg/ml linoleic acid.

The plate was harvested according to the following protocol. To each well, 10 µl sterile PBS was added. After a short incubation time, the bacteria in each well was individually resuspended and transferred to a fresh plate. The cells were then pelleted by centrifugation and washed twice with MilliQ water. The pellets were then resuspended in 90 µl freshly prepared 0.05 M NaoH (100 µl of 30% NaOH in 20 ml of MilliQ Water). The plates were then incubated in a PCR machine at 60° C. for 45 min. Then the reaction was neutralized by adding 9.2 µl Tris pH 7 and 5 µl of the supernatant was used as template in a 20 µl PCR reaction. PCR was conducted to amplify the SLST allele in order to characterize the population. The Primer sequences used were:

```
SLST FW:
                                       (SEQ ID NO: 81)
TCGTCGGCAGCGTCAGATGTGTATAAGAGACAGCAGCGGCGCTGC
TAAGAACTT
and SLST-RV:
                                       (SEQ ID NO: 82)
GTCTCGTGGGCTCGGAGATGTGTATAAGAGACAGCCGGCTGGCAA
ATGAGGCAT (Scholz et al., 2014).
```

Samples were amplified using a Kappa polymerase (5 min 95° C.; 35 cycles of: (98° C. 20 s, 62° C. 25 s, 72° C. 30 s); 1 min 72° C.). The sequencing library was constructed using two rounds of PCR. The first round used SLST primers which included sequences compatible with Illumina sequencing. The second round (10 cycles) was used to barcode the different samples for sequencing in a single Illumina flowcell. The PCR reactions and the 3-S-Biokit DNA extractions were purified using Magnetic beads which were prepared according to (Rohland and Reich, 2012). The indexed reactions were pooled and purified from an agarose gel using the promega WIZARD® SV Gel and PCR Clean-Up System. The final libraries were then quality controlled on an Agilent TapeStation and quantified by qPCR using the KAPA library quantification kit KK4854 on a Roche Light-Cycler 480. Illumina MiSeq sequencing was conducted using a MiSeq Reagent Kit v3 with 2*300 Bp reads (MS-102-3003).

Samples were analyzed using an internally developed computational pipeline (S-genotyping). Quality filtering; samples were mapped into an internal database using bwa software; data processing and visualization was conducted with R statistical language. The latest library of the *P. acnes* SLST types was downloaded from medbac.dk/slst/pacnes.

This experiment showed that the growth behavior of individual strains differs from their growth behavior as mixtures. It was expected that strains which grow fast in isolation like A5 would take over the culture. Surprisingly a slow growing strain (K8) which would have been expected to contribute only a minor amount to the final mixture was the main contributor to the final biomass if grown in the presence of other strains. FIG. 7 shows the change of relative composition of a mixture of different *P. acnes* strains determined by sequencing reads before and after 5 days of growth on RCM agar. Surprisingly, the strain K8 which was very slow-growing when used as insolate took over most of the culture in the 5 days of the experiment. Before the experiment, all strains were normalized according to their OD to represent 16% of the biomass in the starting culture. After the experiment, K8 was the most dominant strain with 69%. Only E3 was also able to increase its share in the biomass. The portion of C3 reduced to 8% while A5, C1 and F4 reduced to below 1%.

Example 4: Determination of Minimum Bactericidal Concentration (MBC) and Minimum Inhibitory Concentration (MIC) for Isolated Strains and Mixtures of Strains with DMDM Hydantoin and Benzoic Acid, Common Preservatives Found in Cosmetic Products Experiments were conducted to simulate the application of a cosmetic product containing preservatives on the skin of a human subject and to assess the effect of those preservatives on the skin microbiome of the subject. It was investigated whether there is any difference between the effect of the preservative on a single strain or on a mixture of multiple strains.

Four individual strains of P. acnes were grown in separate cultures as inoculum. Subsequently, each culture was normalized according to its OD and challenged with DMDM Hydantoin or benzoic acid, which are two preservatives commonly used in cosmetics. Each strain was tested alone and in combination with other strains. Individual strains and combinations of strains were exposed for 24 h to the preservative and then subsequently plated on agar to determine minimum bactericidal concentration (MBC) and minimum inhibitory concentration (MIC) of the preservative.

The strains A5, C3, F4 and K8 were grown from −80° C. stocks in Reinforced Clostridial Medium (RCM) (Becton-Dickinson, catalog number 218081, Franklin Lakes, N.J.). For each strain, 50 ml of RCM was inoculated with 0.5 ml of an OD 1.0 stock. The OD was measured in regular intervals while the bacteria were incubated at 37° C. For the MIC testing, the bacteria were harvested in exponential phase and normalized as described below. For the MBC testing, the bacteria were grown until reaching stationary phase and incubated at 37° C. for another 24 h before they were processed for the experiment. The samples were then normalized to an OD of 0.5, using RCM media as a diluent.

Working solutions of DMDM Hydantoin (Sigma-Aldrich, St. Louis, Mo., catalog number PHR1358-1 ML) and Benzoic acid (Sigma-Aldrich, St. Louis, Mo., catalog number 242381-25G) were prepared in RCM media, with test concentrations of 1%, 0.25%, 0.125%, and 0.1% for DMDM Hydantoin, and 2.5%, 0.63%, 0.31 and 0.25%, as blank control consisting of only RCM. These concentrations represent dilutions corresponding to commonly used amounts in cosmetics. DMDM Hydantoin is limited by the EU to concentrations up to 1% in cosmetics and Benzoic acid is limited by the FDA in "rinse-off-products" to 2.5% and in "leave-on-products" to 0.5%. The exposure was performed in 96-well plates, and each condition was tested in triplicate. For each sample, 200 μl of media containing the preservative was inoculated with 20 μl of normalized bacteria solution.

Strains were added either individually to the challenge media or as a mixture. For each strain, the same overall bacterial count (determined by OD measurement) was used when the strain was added individually or when the strain was added as a component of a mixture. The mixtures consisted of either 2 strains or 4 strains. The two-strain mixture included strains C3 and K8, with each strain representing approximately 50% of the bacterial mass. The four-strain mixture included strains A5 (~35%), C3 (~55%), F4 (~10%) and K8 (~5%). Both the MBC and MIC test were set up in a 96-well plate. To avoid a plate effect, the outermost wells were filled with water. For the MIC test, the bacteria were grown in the presence of the preservative for 5 days in liquid culture under anaerobic conditions before they were analyzed (Table 5).

For the MBC test, the bacteria were exposed to the preservative in the RCM medium for 24 h in an anaerobic environment at 37° C. After 24 h, 10 μl of each test well was transferred to a agar plate (96-well plate) which had each well filled with 200 μl of RCM agar (Sigma-Aldrich, St. Louis, Mo., catalog number 91365-500 g) and was incubated for four days at 37° C. in the absence of oxygen. After 4 days, each plate was analyzed for visible growth of colonies to determine the MBC (Table 6).

TABLE 5

MIC concentrations of different preservatives in liquid RCM medium

MIC DMDM Hydantoin

|  | Blank | 0.10% | 0.13% | 0.25% | 1% |
| --- | --- | --- | --- | --- | --- |
| A5 | +/+/+ | −/−/− | −/−/− | −/−/− | −/−/− |
| C3 | +/+/+ | −/−/− | −/−/− | −/−/− | −/−/− |
| F4 | +/+/+ | −/−/− | −/−/− | −/−/− | −/−/− |
| K8 | +/+/+ | −/−/− | −/−/− | −/−/− | −/−/− |
| C3/K8 | +/+/+ | −/−/− | −/−/− | −/−/− | −/−/− |
| A5/C3/F4/K8 | +/+/+ | −/−/− | −/−/− | −/−/− | −/−/− |

MIC Benzoic acid

|  | Blank | 0.25% | 0.31% | 0.63% | 2.50% |
| --- | --- | --- | --- | --- | --- |
| A5 | +/+/+ | −/−/− | −/−/− | −/−/− | −/−/− |
| C3 | +/+/+ | −/−/− | −/−/− | −/−/− | −/−/− |
| F4 | +/+/+ | −/−/− | −/−/− | −/−/− | −/−/− |
| K8 | +/+/+ | −/−/− | −/−/− | −/−/− | −/−/− |
| C3/K8 | +/+/+ | −/−/− | −/−/− | −/−/− | −/−/− |
| A5/C3/F4/K8 | +/+/+ | −/−/− | −/−/− | −/−/− | −/−/− |

TABLE 6

MBC after 24 h exposure to DMDM Hydantoin and benzoic acid

MBC DMDM Hydantoin

|  | Blank | 0.10% | 0.13% | 0.25% | 1% |
| --- | --- | --- | --- | --- | --- |
| A5 | +/+/+ | +/−/− | −/−/− | −/−/− | −/−/− |
| C3 | +/+/+ | +/+/+ | −/−/− | −/−/− | −/−/− |
| F4 | +/+/+ | −/−/− | −/−/− | −/−/− | −/−/− |
| K8 | +/+/+ | −/−/+ | −/−/+ | −/−/− | −/−/− |
| C3/K8 | +/+/+ | +/+/+ | +/+/+ | −/−/− | −/−/− |
| A5/C3/F4/K8 | +/+/+ | +/+/+ | +/+/+ | −/−/− | −/−/− |

MBC Benzoic acid

|  | Blank | 0.25% | 0.31% | 0.63% | 2.50% |
| --- | --- | --- | --- | --- | --- |
| A5 | +/+/+ | +/+/+ | +/+/+ | −/−/− | −/−/− |
| C3 | +/+/+ | +/+/+ | +/+/+ | −/−/− | −/−/− |
| F4 | +/+/+ | +/+/+ | −/−/− | −/−/− | −/−/− |
| K8 | +/+/+ | +/+/+ | −/−/− | −/−/− | −/−/− |
| C3/K8 | +/+/+ | +/+/+ | +/+/+ | −/−/− | −/−/− |
| A5/C3/F4/K8 | +/+/+ | +/+/+ | +/+/+ | −/−/+ | −/−/− |

Results

The in vitro test simulated two scenarios. The MIC test represented a scenario in which P. acnes contaminates a classical cosmetic product. The MBC test simulated a scenario in which bacteria living on the skin are exposed to a preservative from topically applied cosmetics.

As expected, in the MIC test, both preservatives efficiently inhibited growth when present in the liquid growth media. Even at significantly lower concentrations than commonly used in cosmetics, no growth of the individual P. acnes strains or mixtures was detected.

In the MBC test, the results were surprisingly different from the MIC test. Benzoic acid, a common preservative, affected the growth of all strains at concentrations greater than 0.31% vol/vol. However, differences were observed between the different strains. Strains A5 and C3 survived 24 h exposure to 0.31% benzoic acid, while strains F4 and K8 were not able to grow after this exposure. The mixtures of strains grew only to the maximum concentration of benzoic acid 0.31% that was tolerated by the individual strains. "Leave-on" products contain a maximum concentration of 0.5% of benzoic acid. Based on the data, such a concentration might affect only some of the P. acnes strains while others will survive such a concentration.

Surprising results were obtained when performing the same test with DMDM Hydantoin. Unexpected growth of the mixture of strains was observed at concentrations higher (0.13%) than those tolerated by any individual strains alone (0.1%). This indicates that a bacterial community of P. acnes strains established on the skin will have improved survival against the exposure to products containing preservative such as DMDM Hydantoin compared to single bacterial strains established on the skin. This provides an unexpected advantage for bacterial mixtures compared to individual strains for the establishment and long term persistence on the skin of a human subject. The combinations of two strains provided a better resistance against a formaldehyde releasing agent like DMDM Hydantoin than any individual strains tested.

Example 5: Clinical Study in Acne Patients (ACBAC)

A clinical pilot study in acne patients was performed. The pilot study evaluated bacterial engraftment of the microbiome as well as safety and efficacy trends. Based on the pilot study, including criteria such as safety, stability and responder rate, one of the mixtures tested in the pilot study was chosen for a larger clinical study.

Pilot Study Schedule

Figure 25:
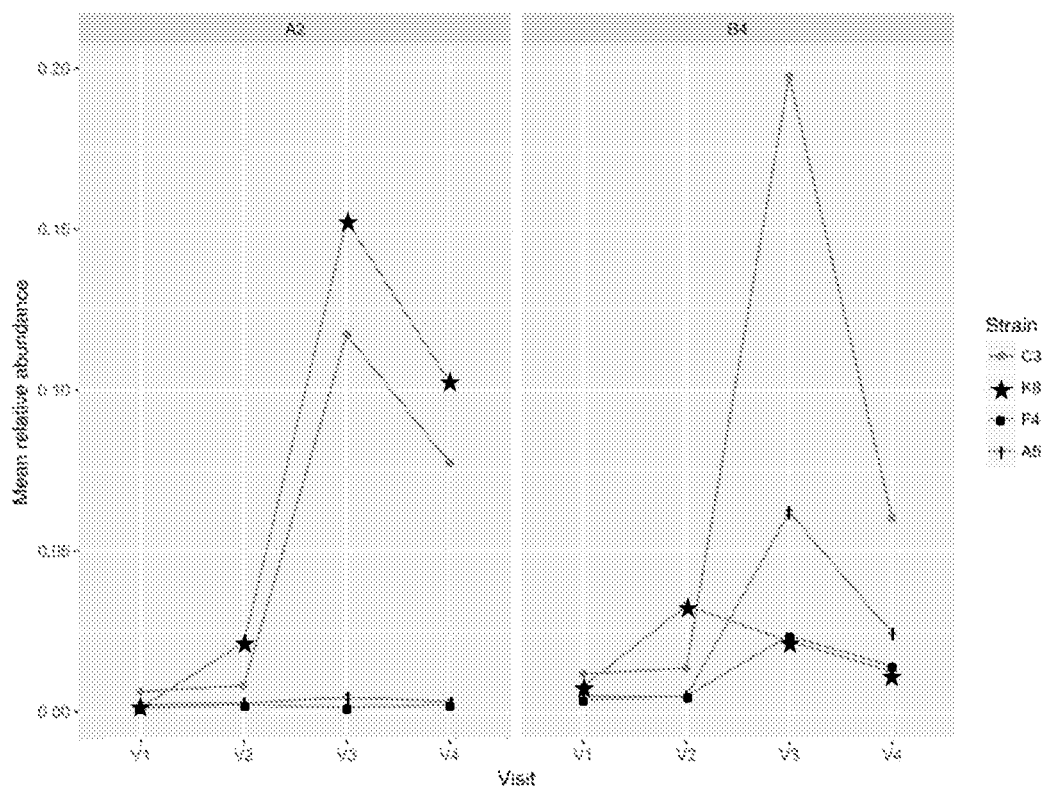
FIG. 25 depicts the change of relative concentrations of different P. acnes strains following administration of formulations A2 and B4.

The pilot study was performed for 6 weeks with 14 subjects between 18-23 years. The primary endpoints were safety and efficacy trends. Two different bacterial formulations: A2 (a 2-strain mixture comprising strains C3 and K8 of P. acnes) and B4 (a 4-strain mixture comprising strains C3, K8, A5, and F4 of P. acnes) were tested. Consistent with the data described in Example 2, the subjects receiving the A2 formulation showed a higher or equal relative abundance of K8 on the skin relative to C3, suggesting that strain C3 helps the slower growing K8 strain to colonize the skin (FIG. 25).

Both formulations showed an excellent safety profile with no adverse effects. A significant reduction in non-inflamed lesions and a slight trend in reduction of inflamed lesions were observed. Further, a decrease in the skin pH, which is generally considered as a positive development in healthy skin, was observed. Due to noisy sebumeter measurement, potential changes in the sebum production are still being investigated. The analysis of the more sophisticated sebutape measurement is still ongoing. In some of the subjects, the increase of the applied strains was clear and significant (e.g., an increase by at least 15% on both Day 21 and Day 42 compared to Day 1). The relative abundance of strains was measured with amplicon sequencing of the SLST (NGS). These subjects were defined as acceptors. As discussed below, the acceptor subjects exhibited effects, for example, on non-inflamed lesions and pH. Therefore, the results from the pilot study were positive and led to a larger clinical study.

Pilot Study Design

Figure 8A:
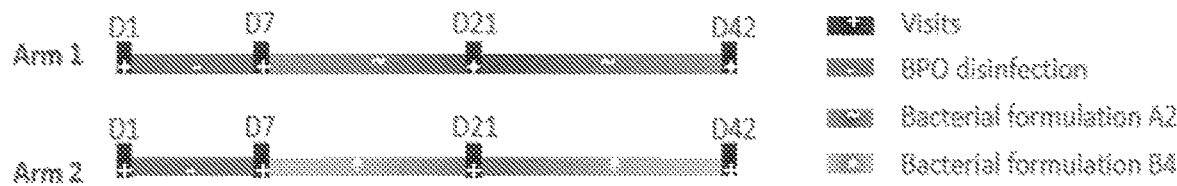
FIG. 8A depicts the administration schedule used in a pilot clinical study. 14 subjects were split into two arms where each arm received a different bacterial formulation.

Subjects were randomly distributed into two arms with different bacterial formulations administered to the subjects in each arm. Bacterial formulations were double-blinded: Arm 1: n=8 subjects received formulation A2. Arm 2: n=6 subjects received formulation B4. Subjects were evaluated on Day 1, Day 7, Day 21, and Day 42. In the first week, between Day 1 and Day 7, all subjects received Benzoyl peroxide (BPO) treatment (applied once a day). In the following 5 weeks, between Day 7 and Day 42, all subjects received bacterial formulation (gel applied 2× per day). FIG. 8A depicts the design of the pilot study.

Subjects were examined during 4 visits—on Day 1, Day 7, Day 21, and Day 42. Table 7 shows measurements taken and documented during each visit.

Safety

The safety of the administered formulations was evaluated, for example, by visual evaluation of the redness, irritation or any other skin problems during each visit. No safety issues were observed during the study. Seven subjects reported dry or red skin during the use of BPO (Day 1-Day 7). However, the skin of the subjects did not get red, irritated or otherwise disturbed during the administration of live bacteria. No adverse effects were observed associated with the administration of live bacteria.

TABLE 7

| | Pilot Study | | | | | | | |
|---|---|---|---|---|---|---|---|---|
| | Lesion count | Safety | Image | Micro-biome sample | Sebu-tabe | Sebu-meter | pH | Self-evaluation |
| V1 (D1) | X | X | X | X | X | X | X | X |
| V2 (D7) | | X | X | X | | X | X | |
| V3 (D21) | | X | X | X | | X | X | X |
| V4 (D42) | X | X | X | X | X | X | X | X |

Microbiome Samples
Bacterial Species Resolution (16S)

Figure 9:
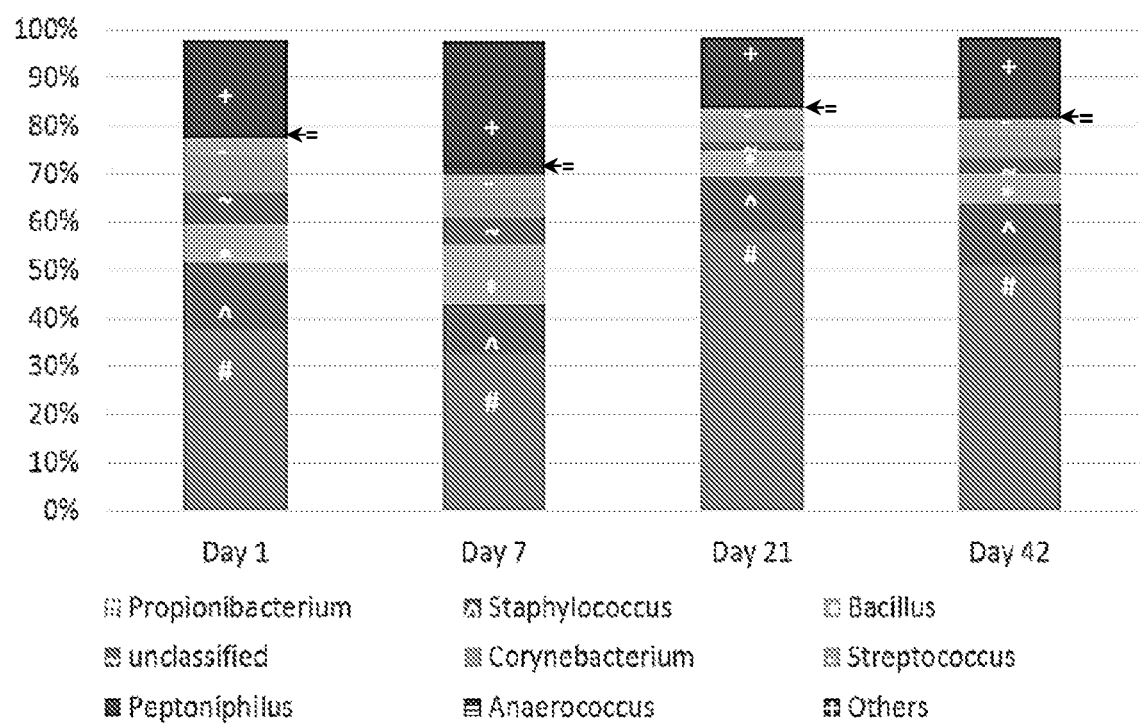
FIG. 9 depicts averaged relative ratios of the nine most abundant bacteria in the skin microbiome of all subjects in the 14 subject pilot study.
Figure 11A:
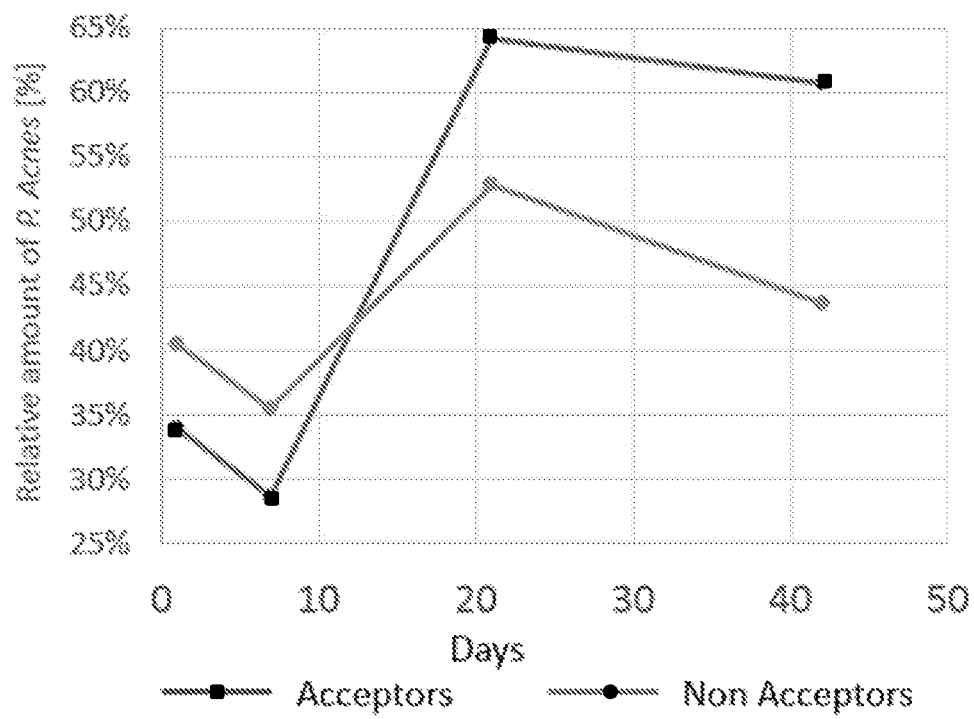
FIGS. 11A and 11B depict the relative amount of *P. acnes* within the complete bacterial skin microbiome.
Figure 11B:
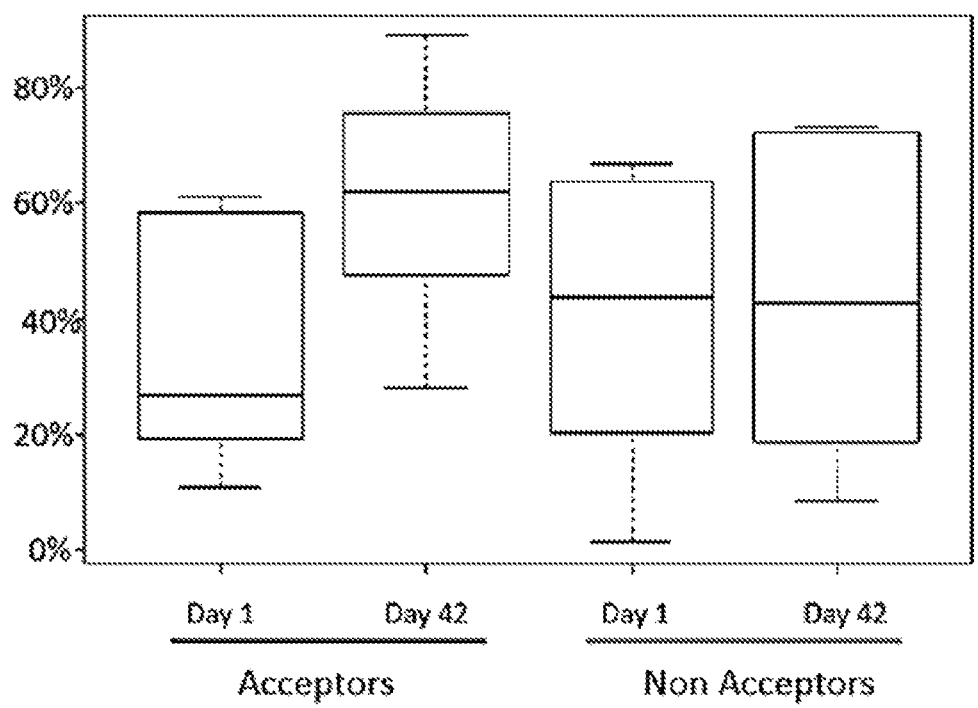

The composition of bacterial species (16S) in the microbiome samples were analyzed on each visit. FIG. 9 depicts the relative ratios of the nine most abundant bacteria in the skin microbiome of all of the subjects in the study. A decrease in the total P. acnes population was observed after BPO application (Day 7) (FIG. 11A). A significant increase in the total P. acnes population was then observed after two weeks of bacterial application (Day 21) (FIG. 11A). A slight decrease in the total P. acnes proportion was observed after five weeks of bacterial application (Day 42). Without wishing to be bound by any theory, this decrease may represent a balanced state of the microbiome and/or an increase in the diversity of the bacterial population. FIG. 11B shows the relative ratios of P. acnes as box plots. These observations show a positive trend in the microbiome composition development following administration of formulations described herein.

Strain Level Resolution of P. acnes (SLST)

Using Single Locus Sequence Typing (SLST), the P. acnes strain level composition of microbiome samples taken on each visit (Day 1, 7, 21 and 42) was determined.

Figure 10:
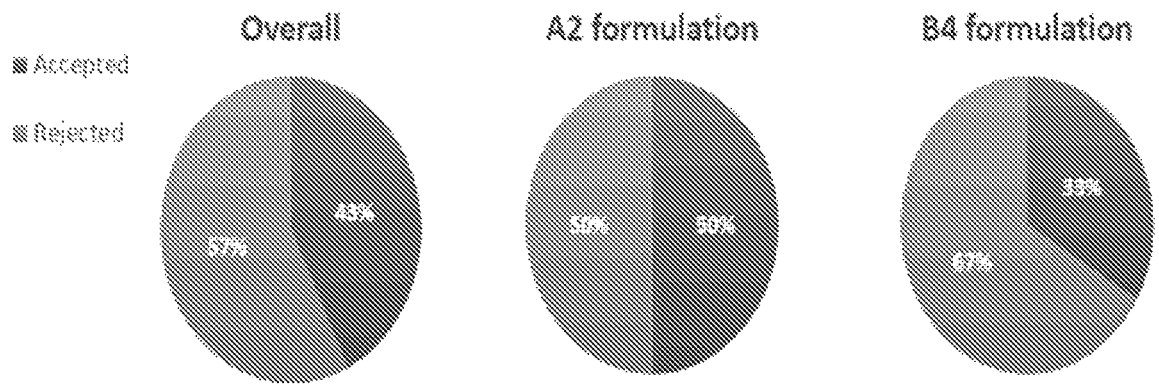
FIG. 10 depicts the relative ratios of subjects classified as acceptors or non-acceptors.

Commonly found strains were dominant in most samples on Day 1 (ground state). Following administration of the bacterial formulations, in most subjects, a shift in the composition of the skin microbiome towards the applied strains was observed. In some subjects, the increase of the applied strains was clear and significant (increased amount of defined strain by at least 15% on both Day 21 and Day 42 compared to Day 1). These subjects were classified as acceptors. In some subjects, the increase of the applied strains was less noticeable. These subjects were classified as non-acceptors. FIG. 10 depicts the relative ratios of subjects classified as acceptors and non-acceptors.

Overall, 43% of subjects were classified as acceptors and 57% were classified as non-acceptors. Split by formulation, 50% acceptors and 50% non-acceptors were observed in the A2 formulation group, while 33% acceptors and 67% non-acceptors were observed in the B4 formulation group. Due to the small size of both groups, the difference between the two groups is not statistically significant.

No other confounding factors, such as age, gender, use of anti-bacterial products, or showering pattern, that would be likely to significantly influence the probability of being an acceptor were observed.

Bacterial Species (16S) and Strain Level (SLST) Analysis

When relating the bacterial species (16S) data with the strain level data (SLST) of P. acnes, it was observed that on Day 1 (ground state) the relative abundance of P. acnes was lower in acceptors (34%) compared to non-acceptors (41%). During the study, the average relative abundance of P. acnes in acceptors increased almost twice (60%) towards the Day 42 (final visit). Relative abundances were determined using classical 16S amplicon sequencing. In this method, which is well-known in the art, a specific part of the 16S ribosomal subunit is amplified out of all bacterial DNA in the sample by PCR. Different bacterial species present in the sample are identified by sequencing the amplicon. Next generation sequencing allows for assessment of the complete relative distribution of all sequences/species in the sample.

The non-acceptor group exhibited only a minor and not statistically significant increase of P. acnes during the study as analyzed by a t-test (FIG. 11).

Summary of Microbiome Results

In a subset of patients, the applied bacteria was effectively established following administration. This subset of subjects was characterized by a lower proportion of P. acnes at the beginning of the study and a significantly increased P. acnes proportion at the end of the study.

Acne Lesion Count

During the visit on Day 1 (ground state) and Day 42 (final visit), a dermatologist counted the number of lesions on the face of the subjects. Lesion counts were split into inflamed and non-inflamed lesions.

Non-Inflamed Lesions

Non-inflamed lesions are also known as comedones. Comedones may be open (blackheads) or closed (whiteheads).

Figure 12:
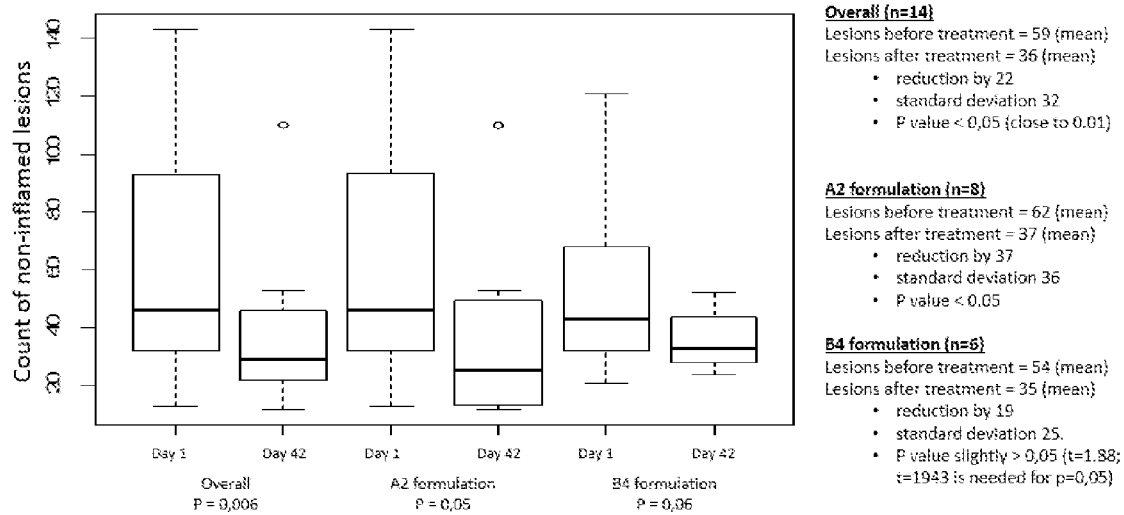
FIG. 12 depicts counts of non-inflamed lesions represented as box plots. Three pairs of boxplots are shown: overall; A2 formulation; and B4 formulation. The p-value for statistical significance is given below the plots.

A substantial reduction of non-inflamed lesion (by 37%, P=0.006) in both formulations was observed. The reduction in the A2 formulation corresponded to 55%, P=0.05, and in the B4 formulation corresponded to 35%, P=0.06. (FIG. 12).

Figure 13:
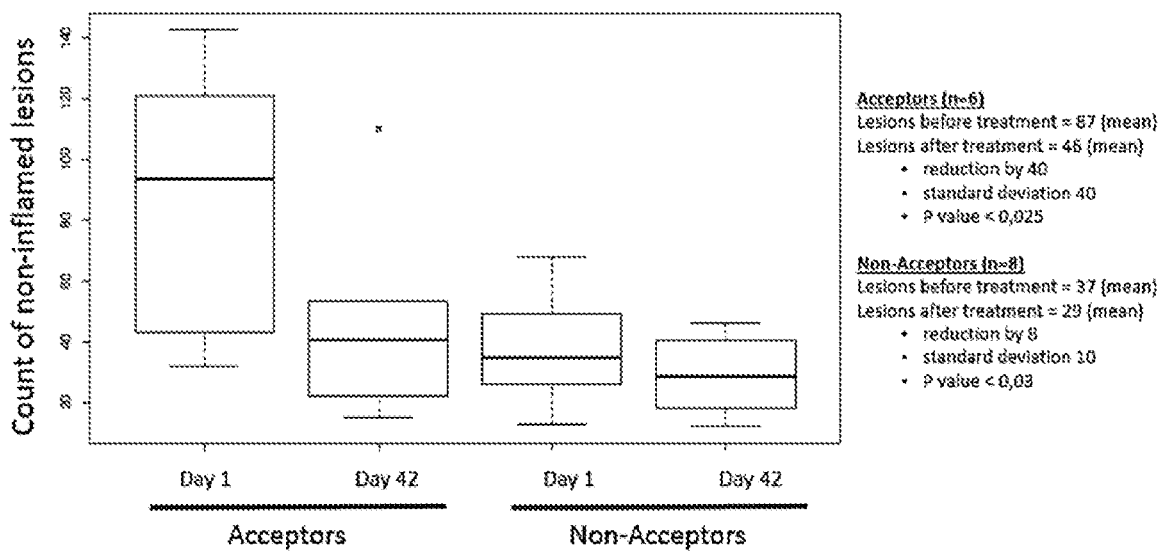
FIG. 13 depicts the number of non-inflamed lesions for acceptors and non-acceptors. For both groups, the reduction is statistically significant.

Comparing the reduction of non-inflamed lesions between acceptors and non-acceptors (subjects who changed/not changed their skin microbiome composition), most of the lesion reduction was observed within the acceptor group (FIG. 13).

After stratifying the groups into acceptors and non-acceptors, the effect was statistically significant in both groups, with p-values below 0.03. The non-acceptors had overall less non-inflamed lesions in the ground state (Day 1); however, because of the smaller spread and less pronounced lesion reduction, the result was still highly statistically significant (FIG. 13)

Inflamed Lesions

An inflamed lesion usually follows rupture of the wall of a closed comedone (non-inflamed lesion). It may also arise from normal-appearing skin Inflammatory lesions in acne can include in some embodiments small red bumps (papules), pustules, large red bumps (nodules) and pseudocysts (fluctuant nodules).

Figure 14:
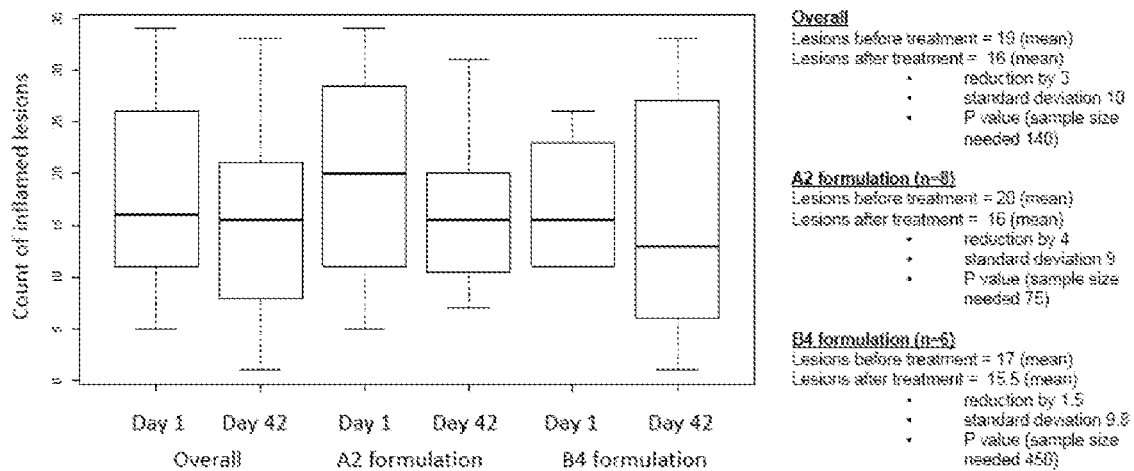
FIG. 14 depicts the count of inflamed lesions represented as box plots. Three pairs of boxplots are shown: overall; A2 formulation; and B4 formulation.
Figure 15:
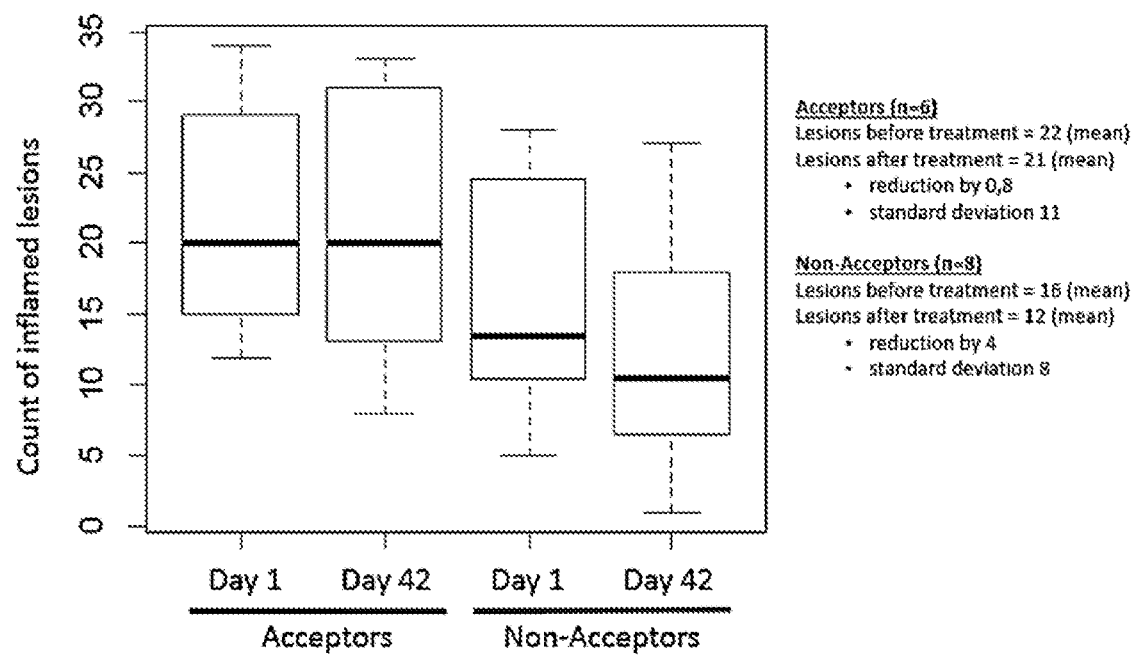
FIG. 15 depicts the number of inflamed lesions for acceptors and non-acceptors.

A reduction in the number of inflamed lesions was observed following administration of bacterial formulations. The average of all subjects (across both formulations) was 19 inflamed lesion before the treatment and 16 afterwards, corresponding to a reduction of approximately 15% after the treatment. The A2 formulation produced an approximate 20% reduction (20/16), while the B4 formulation produced an approximate 9% reduction (17/15.5) (FIG. 14). While this difference was not statistically significant, and a significant difference was not noted between acceptors vs. non-acceptors (FIG. 15), the lack of statistical significance was likely due at least in part to the short duration of the study, the small sample size, and the low number of total lesions, leading to a high standard deviation. Without wishing to be bound by any theory, treatment with live bacteria may exhibit a slower effect on inflamed lesions relative to non-inflamed lesions because non-inflamed lesions are precursors to inflamed lesions. Based on the observed data, a statistically significant effect on reduction of inflamed lesions is expected in a study of longer duration.

Sebum Measurement

Two types of assays were used to assess the sebum production of the subjects. Sebumeter measurement was conducted during each visit (Day 1, 7, 21 and 42), while sebutape measurement was only conducted on Day 1 (ground state) and Day 42 (final visit) as the sampling is time-consuming. Initial readings with a sebumeter did not reveal a general trend. However, the sebumeter simply provides a quick measurement but is less reliable than some other assays because it is strongly influenced by external factors like washing, sweating etc.

Skin pH Measurement

The pH of the subjects' skin was measured during each visit (Day 1, 7, 21, and 42) using a pH meter. A decrease in skin pH of the subjects was observed by 0.4 points between Day 1 and Day 42. Decrease in pH is considered a positive development towards healthy skin.

Figures 16, 17:
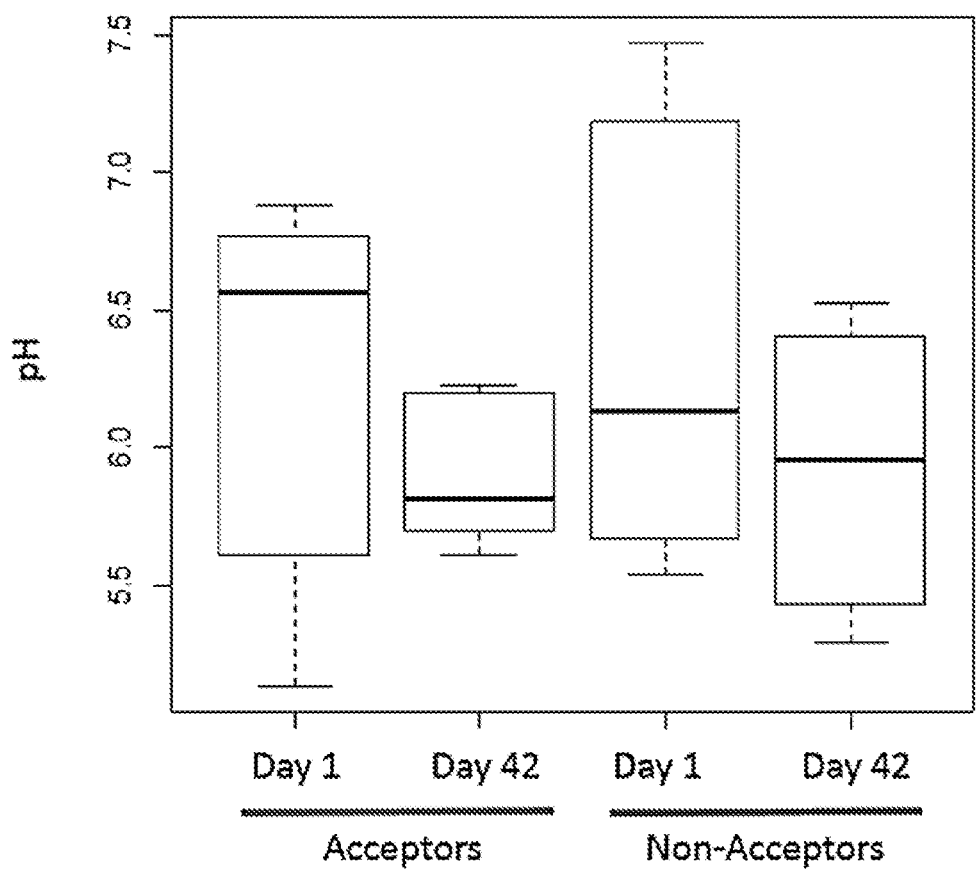
FIG. 16 depicts development of the skin pH throughout the pilot study for acceptors and non-acceptors.
FIG. 17 depicts distribution of subject counts based on the average value of their answers.

Similar to the non-inflamed lesions, the effect was more pronounced in subjects classified as acceptors and less pronounced in subjects classified as non-acceptors (FIG. 16). A correlation based on the specific formulation administered was not observed. The observed effect is in the same magnitude as reported by Nodake et al. (2015).

Self-Evaluation

Subjects answered a questionnaire during each visit. The questionnaire related to self-evaluation of their skin and about the use of the product. The following skin aspects were reviewed: appearance of pimples, number of pimples, appearance of redness associated with the pimples, size of pimples, severity of pimples, oiliness of skin, shininess of skin, dryness of skin, flakiness of skin, skin smoothness, and overall appearance of skin.

Using the average of the above-mentioned questions, 85% of subjects reported improvement and 15% of subjects reported no change between Day 1 and Day 42. The average improvement overall (average of all questions among all subjects on Day 1 versus Day 4) was by 1.62 points (on scale 1-10). Higher satisfaction was observed among the A2 formulation users (2.05 points) and among the acceptors (1.75 points).

Among all subjects, the most improvement was observed in "Dryness of skin" (by 2.21 points) followed by "Overall appearance of skin" (2.07 points) and "Skin smoothness" (2.00 points).

Based on top-box analysis, the scale was split into three boxes: Bottom=points 1-3, Middle=points 4-7 and Top=points 8-10. FIG. 17 shows a distribution of subjects based on their average value of all answers for each visit (Day 1, 7, 21 and 42). A clear shift towards higher scores is visible throughout the study. A high acceptance rate of the product and a general positive feedback from the subjects in the self-evaluation was observed.

Figure 18:
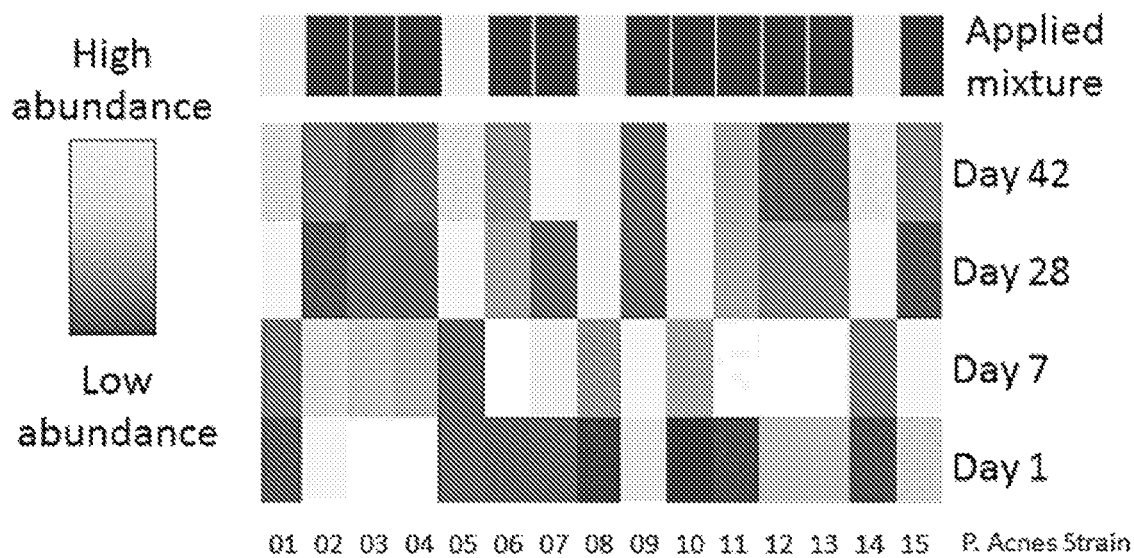
FIG. 18 depicts a heatmap showing the relative abundance of the 15 most commonly found *P. acnes* strains. The heatmap represents the average of 6 subjects classified as acceptors who showed very good establishment of the new bacteria. A clear change in the composition of the microbiome is visible between Day 1 and Day 42.
Figure 19:
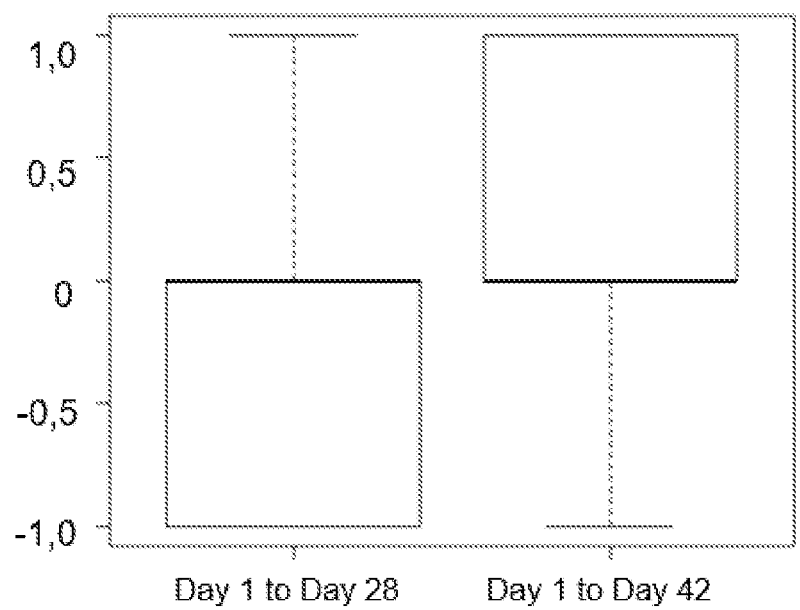
FIG. 19 depicts a graph showing results of a picture based comparison. Results from Day 1 to Day 28 were compared with results from Day 1 to Day 42. Each Picture was rated with +1 if the subject improved, 0 if the subject appeared not to change and −1 if the subject worsened. The averages are Day 1 to 28: −0.17 and Day 1 to 42: 0.29. The difference is statistically significant, p<0.05.
Figure 20:
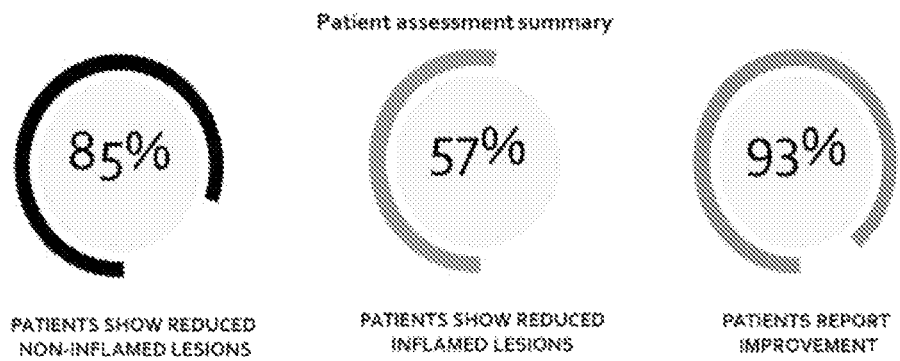
FIG. 20 shows results of a patient assessment summary, demonstrating improvement of inflamed and non-inflamed lesions during the 42 day clinical study.
Figure 21:
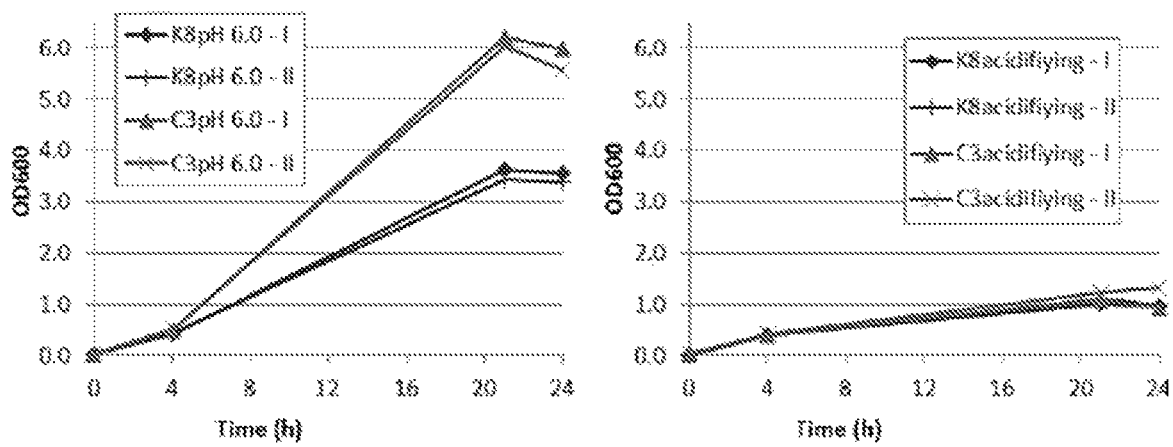
FIG. 21 depicts $OD_{600}$ of pH-controlled cultures and cultures without pH control ("acidifying") of P. acnes K8 and C3 strains, as described in Experiment 1.2. The graphs show data from duplicate cultures.

FIG. 18 shows a heatmap of the relative abundance of the 15 most commonly found *P. acnes* strains. FIG. 19 shows data from a picture-based comparison. FIG. 20 shows data from a patient assessment summary. Some subjects exhibited an initial decline on visit 3 but showed a general improvement by visit 4. Without wishing to be bound by any theory, adapting to newly established strains could contribute to a temporary flare up. At the beginning and the end of the study a lesion count was performed. The majority of subjects showed a decrease in acne lesions.

Summary of Pilot Study

A statistically significant decrease in the number of non-inflamed lesions was observed. This was surprising because in standard-of-care treatments, a reduction of non-inflamed lesions is generally only observed over the long term. In a comprehensive meta-analysis comparing BPO and other state-of-the-art treatments (Seidler and Kimball, 2010) the placebo arm showed a decrease by 6.7% in non-inflamed lesions. In the study described herein, the acceptor group had a reduction of nearly 50%, indicating that an effect beyond the placebo could be observed. The magnitude of the effect could potentially outperform current state-of-the-art treatments in the ability to target non-inflamed lesions.

Based on analysis of the 16S microbiome data and correlation with the strain-level resolution of the *P. acnes* population, it was apparent that the subjects who accepted the applied bacterial strains (classified as acceptors) exhibited an increase in the relative proportion of *P. acnes* compared to all other bacteria. The non-acceptors maintained their relative ratio of *P. acnes* throughout the study, but were characterized by a higher relative percentage of *P. acnes* at the baseline visit (Day 1). Without wishing to be bound by any theory, the non-acceptors may have already been fully colonized by *P. acnes*, such that the disinfection treatment which was administered before the bacterial strains were administered may not have been sufficient to eliminate the resident *P. acnes* population, which may have remained hidden in the follicles. By contrast, the acceptors may not have yet been fully colonized allowing the disinfection treatment to reduce or eliminate the resident *P. acnes* population before administration of the bacterial strains. Modified disinfection procedures may allow for an increase in the acceptor rate.

The effect observed for the skin pH was on the same magnitude as that reported by other randomized double blinded clinical trials using skin bacteria (Nodake et al., 2015). It is also encouraging that not only did the pH drop, but it also decreased its variance throughout the study, suggesting a normalization of the subjects' skin pH.

Many subjects in the pilot study reported a smoother skin, which is in correlation with the decrease of non-inflamed lesions as documented by the dermatologists participating in the pilot study. In addition, many subjects noted a less greasy skin, which could be an indicator of reduced sebum production.

The data show that modulation of the skin microbiome at the strain level was well tolerated. The majority of the subjects experienced an overall improvement of their skin condition. Specifically a decrease in itchiness, less noticeable acne lesions, and better overall skin appearance was reported. None of the subjects experienced a significant deterioration or a prolonged flare-up. There were no drop-outs in this clinical study.

Materials and Methods

Materials used for *P. acnes* production included: 1 L schott bottles; Cell Culture flasks Magnet; Serological pipets; Pipet tips with filter, 10000; Falcons; Cups for spinning large batches; Petri dishes; Syringes 2.5 ml; Straw for syringes; Caps for syringes; and Eppendorfs. Chemicals used include: NATROSOL® 250 Hx Pharm., Hydroxyethylcellulosum; Kat-Hefe Media; Dextrose (α-D-Glucose), anhydrous 96%, Aldrich, ref:158968; Sodium Chloride (NaCl); Reinforced Clostridial Agar; and Peptone from Casein, tryptic digest.

Bacterial media preparation: RCM Agar was prepared by following the supplier instructions, including for each liter: autoclaving the mixture in a Liquids program; adding 200 μl of Furazilidone 100 mg/ml to each 1 L final volume before distributing the agar; and distributing the prepared RCM Agar to Petri dishes and flat-bottom 96 well plates (200 μl each well).

The following solutions were prepared:

1) Media based solution mix in a 1 L Schott bottle which includes: 20 g of Kat-Hefe protein; 5 g of NaCl; and 900 ml of water 2) 10× Dextrose solution mix in a 100 ml Schott Bottle, which includes: 30 g of Dextrose (α-D-Glucose) and 100 ml of water.

Both solutions were autoclaved. After cooling aseptically, 100 ml of 10× Dextrose solution was added to the media based solution (1 L bottle) forming the final media. The final media contained the following concentrations: 20 g/L of Kat-Hefe protein; 5 g/L NaCl; and 30 g/L of Dextrose.

A peptone solution mix was prepared in a 1 L Schott Bottle, which includes: 2.5 g of peptone from casein, tryptic digestion and 1 L water. This solution was autoclaved in a liquids program. The final solution contained 0.25% peptone.

Bacteria Culture

Bacterial pre-culture preparation was started from a confirmed pure strain. Each falcon was filled with 50 ml of RCM media. A syringe containing the desired strain at room temperature is thawed and 0.5 ml gel is transferred into the corresponding falcon, according to strain. The bacterial cultures are grown at 37° C.

Steps to create the bacteria culture are outlined below:
- 50 ml pre-culture was added to 450 ml Kat-Hefe media in 750 ml sterile cell culture flask (main culture). The samples were placed in the incubator at 37° C. and growth was monitored by regular OD measurements
- Samples were spun down for 10 min and the supernatant was removed
- Samples were washed once in 50 ml of 0.25% Peptone from casein, tryptic digestion
- Samples were spun down for 10 min and supernatant was removed
- Each pellet was re-suspended in 50 ml of 0.25% Peptone from casein, tryptic digestion
- Bacteria suspensions were normalized
- Bacterial mixtures were prepared according to the desired formulation
- Sterile Hec powder was added to prepare the gel and it was allowed to rest
- Syringes were filled A *P. acnes* C3 strain and a *P. acnes* K8 strain were each deposited on Oct. 19, 2017 at DSMZ (Leibniz-Institut DSMZ-Deutsche Sammlung von Mikroorganismen and Zellkulturen GmbH), Inhoffenstraße 7 B, 38124 Braunschweig, Germany.

Example 6: Production of *P. acnes* for Large Scale Clinical Study

Samples of bacterial strains to be used in a large scale clinical trial were produced, as well as placebo samples without bacteria, using Food Grade procedures. The samples produced included 9000 1-ml aliquots of a gel medium containing a 1:1 blend of two *P. acnes* strains in a concentration of at least $1 \times 10^7$ cfu per aliquot, packed aseptically in sealed laminated aluminum foil sachets and stored at −80° C., and 5500 1-ml aliquots of the gel medium without bacteria, packed in the same sachets and stored at −80° C. (placebo samples). Methods used for the production of the *P. acnes* bacterial strains and associated results are described herein. The work was divided in two phases. In Part 1, protocols for growth, harvesting, and storage of the bacteria were developed and evaluated. Part 2 consisted of production and packaging of the blend of bacteria and the placebo samples.

Materials and Methods
Strains, Media and Cultivation Conditions

*P. acnes* strains K8 and C3 were obtained as cultures diluted in 2.5% hydroxyethylcellulosum (HEC) in sterile 1-ml syringes. The syringes were stored at −80° C.

Stock cultures: strains K8 and C3 were prepared by inoculating about 0.05 ml from the syringe cultures on Brain Heart Infusion Agar (BHIA; Tritium Microbiologie, Eindhoven, Netherlands) plates and overnight incubation at 37° C. in an anaerobic jar. Bacterial material from the plates after incubation was diluted and spread on fresh BHIA plates to obtain single colonies. After overnight anaerobic incubation at 37° C., a single colony from each strain was inoculated in BHI broth (Tritium Microbiologie) and incubated anaerobically overnight at 37° C. The resulting cultures were mixed with a sterile 60% glycerol solution to a final glycerol concentration of 15%, divided into multiple subsamples and stored at −80° C. These stock cultures were used to inoculate precultures in BHI medium used in fermentation Experiments 1.1, 1.2, 1.3 and 2.1. Fresh stock cultures were produced starting from the syringe cultures prior to execution of Experiment 2.2.

The media used in the studies were: Brain Heart Infusion broth (BHI) and Brain Heart Infusion Agar (BHIA); Medium A: 3% dextrose, 0.5% sodium chloride, 2% yeast extract (Ohly Kat, Germany), pH 6.7; Medium B: Medium A plus 1% soy peptone (AM41, Organotechnie, La Courneuve, France), pH 6.7; Medium C: 3% dextrose, 0.5% sodium chloride, 2% yeast extract (Springer 0251/0-MG-L, Biospringer, Maisons-Alfort, France), pH 6.7; Medium D: Medium C plus 1% soy peptone, pH 6.7; and Medium E: Medium D, adjusted to pH 6.3.

A total of five fermentation experiments were conducted, three in Part 1 and two in Part 2, as described below.

Experiment 1.1

*P. acnes* K8 and C3 were cultivated in 100-ml flasks containing 100 ml Medium A, B, C or D. The media were inoculated with 10 ml from overnight cultures in BHI. The flasks were stored in anaerobic jars incubated without shaking for 24 h at 37° C.

Experiment 1.2

*P. acnes* K8 and C3 were cultivated in 400 ml medium D in 0.5-L volume fermentor vessels, equipped with units to control temperature, stirring, and pH (Multifors 2 system, Infors, Bottmingen Switzerland). The medium was inoculated with 40 ml of overnight cultures in medium D (10% inoculation), which were prepared by inoculation of 1 ml of overnight cultures in BHI. The cultivation conditions were: temperature of 37° C.; stirring speed of 150 rpm; pH controlled at pH 6.0 with 2.5 N sodium hydroxide or without pH control; head space flushed with 95% N2/5% CO2 (flow 125 ml/min).

Experiment 1.3

Same set-up and cultivation conditions as described for Experiment 1.2, except that the medium was inoculated with 8 ml of overnight cultures in medium D (2% inoculation).

Experiment 2.1

*P. acnes* K8 and C3 were cultivated in 2.0 L medium D, in 3-L volume fermenter vessels, equipped with units to control temperature, stirring and pH (Applikon Biotechnology, Delft Netherlands). The inoculation procedure and cultivation conditions were the same as described for Experiment 1.3.

Experiment 2.2

Set-up, inoculation procedure and cultivation conditions were the same as described for Experiment 2.1, except that the medium was adjusted to pH 6.0 (medium E; see paragraph 2.1.2) and the stirring speed was increased to 250 rpm.

Harvesting

Experiment 2.2 was used for the production of sachets with *P. acnes* strains. For both strains, a volume of 2.0 L of culture was harvested by means of centrifugation for 10 min at 16,000×g in 1-L centrifugation bottles at ambient temperature. Pellets were resuspended in 200 ml of 0.25% soy peptone (AM41, Organotechnie, La Courneuve, France) solution and centrifuged once more. The bacteria were resuspended in 200 ml of 0.25% soy peptone solution of ambient temperature and processed within 30 min. The optical density at 600 nm ($OD_{600}$) of these concentrated suspensions was 54.3 for *P. acnes* C3 and 48.4 for *P. acnes* K8.

Gel Medium with *P. Acnes* and Placebo Gel Medium

Volumes of 19 ml and 21 ml of concentrated suspension of *P. acnes* C3 and K8, respectively were diluted in 0.25% soy peptone solution to a final volume of 2.0 L. The $OD_{600}$ of this suspension was 1.1 and the ratio between the strains 1:1 on $OD_{600}$ basis. Sterilized HEC was dissolved in this suspension to a final concentration of 1.5% (w/v) under vigorous mixing. This was repeated nine times in total. The batches were mixed to give a total volume of 18 L of gel medium with *P. acnes* K8 and C3. The gel medium was kept at ambient temperature for 1 h before starting packaging in foil sachets. The placebo gel medium consisted of 1.5% HEC in 0.25% peptone solution with iso-valeric acid to a final concentration of 10 µl/L. A total volume of 10 L was produced. The procedure to dissolve HEC was the same as described for the gel medium with *P. acnes*.

Sacheting, Packaging and Storage

Sachets containing gel medium with *P. acnes* or placebo gel medium were produced in independent runs using a sachet packaging machine. The machine consisted of a pump, a sacheting section and a thermo transfer printing unit. The gel medium was pumped from a container to the sacheting section. The sacheting section consisted of sterilized stainless steel tubing (one for gel medium and one for nitrogen gas), around which the sachets were folded, and vertical and horizontal sealing elements operating at a temperature of 130° C. The printing unit, located before the sacheting section, was used to label the sachets. Sachets were produced from 65×65 mm sheets of laminated aluminum foil, which were folded and heat-sealed along three sides (seal width approximately 12 mm). The final sachets were 65×30 mm in size and had a volume of approximately 2 ml. The machine was operated at a production speed of 28 sachets per min and a quantity of gel medium of 1.2 (±0.15) gram per sachet; the rest of the sachet volume is N2 headspace. During filling, the head space of the sachets was flushed with sterile nitrogen gas. At the start of the filling operation and after interruptions 10 to 20 sachets were discarded. At the end of the filling operation, samples of gel medium were taken for microbiological analyses (*P. acnes* viable count and pathogen analysis). Sachets containing gel medium with *P. acnes* were packed in plastic bags (18 sachets per bag). In the course of the filling operations, sachets were transferred to a −80° C. freezer in series of 1000 to 1500 sachets. The sachets were stored at −80° C. until shipment. Sachets with *P. acnes* and sachets with placebo sachets were produced in independent runs.

Analyses

Growth Measurement and Microbiological Analyses

Bacterial mass in cultures was determined by measurement of $OD_{600}$. Viable count of *P. acnes* in cultures and gel medium was determined by plating of serial dilutions on BHI agar, incubated anaerobically for 24 to 30 h at 37° C. To confirm the absence of pathogens in gel medium with *P. acnes* and placebo, gel medium samples were analyzed by an external laboratory (Merieux NutriSciences, Ede, Netherlands) for the following Pathogens listed in Table 9:

| | | |
|---|---|---|
| *Salmonella* | Equivalent to ISO 6579 | Absent in 25 g |
| *Listeria monocytogenes* | Equivalent to ISO 11290-1 | Absent in 25 g |
| *Enterobacteriaceae* | ISO 21528-2 | <10 cfu/g |
| Sulphite-reducing *clostridia* | ISO 15213 | <10 cfu/g |
| Coagulase-positive *staphylococci* | ISO 6888-2 | <10 cfu/g |

FAGS Flow Cytometry

Total counts and viability of cultures was determined using FACS flow cytometry. Viability was determined after staining of cells with a mixture of two nucleic acid stains (green-fluorescent SYTO™ 9 dye and red-fluorescent propidium iodide), using the LIVE/DEAD™ BACLIGHT™ Bacterial Viability and Counting Kit (ThermoFisher scientific cat# L34856).

Results

Part 1

The main objective of Part 1 was to evaluate and improve the protocol for growth of *P. acnes* strains. The protocol consisted of anoxic cultivation in flasks for 2 to 3 days, giving final biomass yields of $OD_{600}$ 0.6 to 1.2. The experiments aimed to increase the yield, to reduce the cultivation time, and to use an up-scalable cultivation system.

Experiment 1.1

Experiment 1.1 was conducted to optimize the medium composition with respect to yield. Two sources of yeast extract were compared and the effect of addition of soy peptone to the medium was determined. The bacteria were cultivated in flasks. Table 10 shows the viable count and $OD_{600}$ of the cultures. The data showed that higher $OD_{600}$ values and viable counts were achieved with Springer yeast extract than with Kat yeast extract. Furthermore, a beneficial effect of soy peptone on $OD_{600}$ and, to a lesser extent, viable count was detected. Higher $OD_{600}$ and viable counts were obtained with strain K8 than with strain C3. Based on these results, the subsequent experiments were conducted with medium containing peptone and Springer yeast extract.

TABLE 10

Effect of yeast extract source and presence of soy peptone in the medium on viable counts and $OD_{600}$ of cultures of *P. acnes* C3 and K8 after 24 h and 48 h incubation at 37° C.

| | | | 24 h | | | 8 h | | |
|---|---|---|---|---|---|---|---|---|
| Strain | Yeast extract | Pep. tone | $OD_{600}$ | cfu/ml | cfu/ml OD1* | $OD_{600}$ | cfu/ml | cfu/ml OD1[1] |
| C3 | Kat | No | 0.32 | 1.8E+06 | 5.6E+06 | 0.63 | 2.7E+07 | 4.3E+07 |
| C3 | Kat | Yes | 0.40 | 1.6E+05 | 4.0E+06 | 0.79 | 3.9E+07 | 4.9E+07 |
| C3 | Springer | No | 0.44 | 1.4E+06 | 3.2E+06 | 0.98 | 6.9E+07 | 7.0E+07 |
| C3 | Springer | Yes | 0.72 | 3.7E+06 | 5.2E+06 | 1.15 | 6.9E+07 | 6.0E+07 |
| K8 | Kat | No | 0.16 | 1.9E+07 | 1.2E+08 | 0.40 | 3.9E+07 | 9.8E+07 |
| K8 | Kat | Yes | 0.19 | 1.0E+07 | 5.2E+07 | 0.80 | 4.5E+07 | 5.6E+07 |
| K8 | Kat | No | 0.45 | 2.8E+07 | 6.2E+07 | 1.58 | >1.0E+08 | — |
| K8 | Springer | Yes | 0.38 | 3.8E+07 | 9.9E+07 | 1.97 | >1.0E+08 | — |

[1]Viable count normalized for culures with an $OD_{600}$ of 1.0

Experiment 1.2

Figure 22:
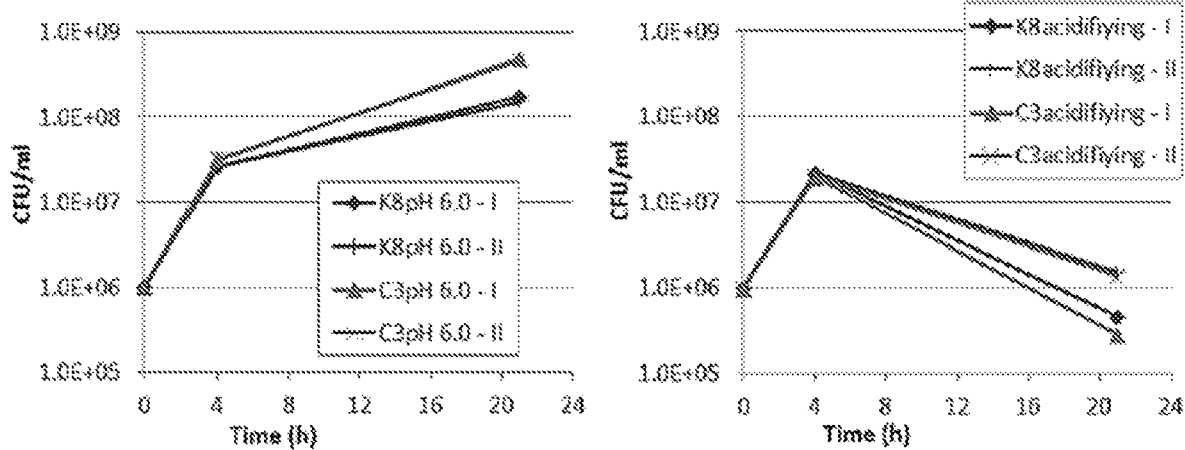
FIG. 22 depicts viable count of pH-controlled cultures and cultures without pH control ("acidifying") of P. acnes K8 and C3 strains, as described in Experiment 1.2. The graphs show data from duplicate cultures.
Figure 23:
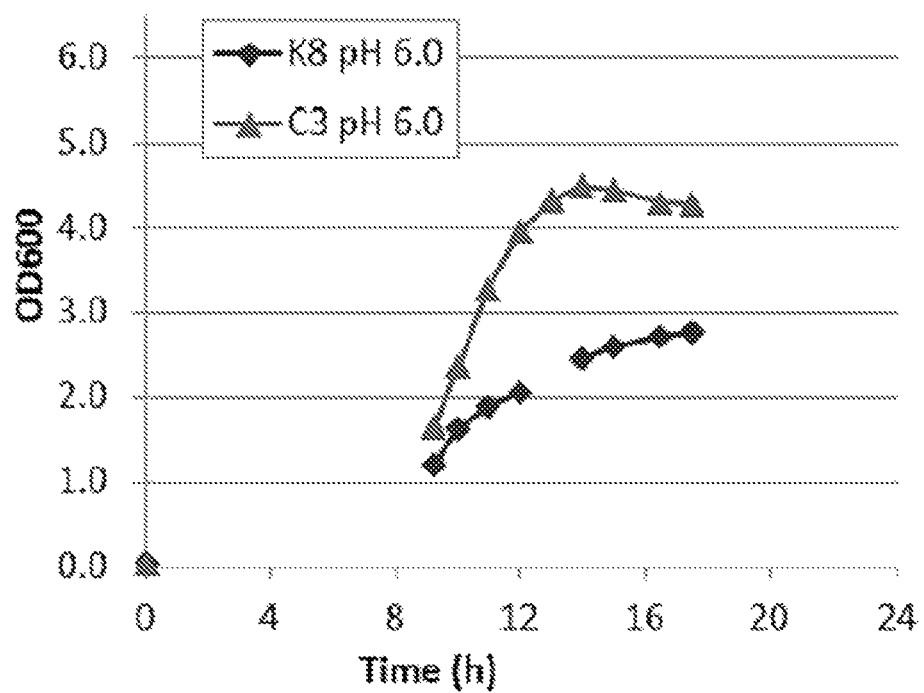
FIG. 23 depicts $OD_{600}$ of pH-controlled cultures ("acidifying") of P. acnes K8 and C3 strains, as described in Experiment 1.3.

Experiment 1.2 was conducted to test the growth characteristics of the strains during cultivation in fermenters and to determine the effect of cultivation at a constant pH of 6.0. Results of $OD_{600}$ and viable count measurements are shown in FIGS. 22 and 23, respectively. The pH-controlled cultures had substantially higher $OD_{600}$ and viable count than the cultures without pH control. Viable counts of cultures without pH control were approximately 25 times lower after 21 h incubation than after 4 h incubation. This finding indicates that in this embodiment, bacteria died, probably due the low pH of the cultures without pH control (pH 5.25). The results depicted in FIG. 22 also showed that the maximum $OD_{600}$ value was reached within 21 h cultivation. The recording of base titration during cultivation of the pH-controlled fermenters (not shown) indicated that the stationary phase was reached already about 14 h after inoculation. In contrast to the results of Experiment 1.1, higher $OD_{600}$ and viable counts were obtained for strain C3 than for strain K8. Based on these results, the subsequent fermentations were conducted with pH-control set at pH 6.0.

The stability of P. acnes C3 and K8 in gel medium during storage of bacteria at −80° C. was tested by measuring the viable count before storage and after 3 weeks of storage. The bacteria were harvested and suspended in gel medium (2.5% HEC). The pH-controlled culture of K8 and the cultures of C3 and K8 without pH control showed no or a small reduction of the viable count during the storage period. In contrast, the viable count of the pH-controlled culture of C3 declined by about 60% (Table 11).

TABLE 11

Effect of 3 weeks storage at −80° C. on the viable count (cfu/ml) of P. acnes strain C3 and K8 cultivated with or without pH control and suspended in 2.5% HEC gel medium.

| Culture | Before storage | After 3 weeks storage |
|---|---|---|
| C3 without pH control | 5.2E+05 | 6.2E+05 |
| K8 without pH control | 5.0E+05 | 6.4E+05 |
| C3 pH-controlled | 4.7E+07 | 1.8E+06 |
| K8 pH-controlled | 4.7E+07 | 1.9E+07 |

Experiment 1.3

Figure 24:
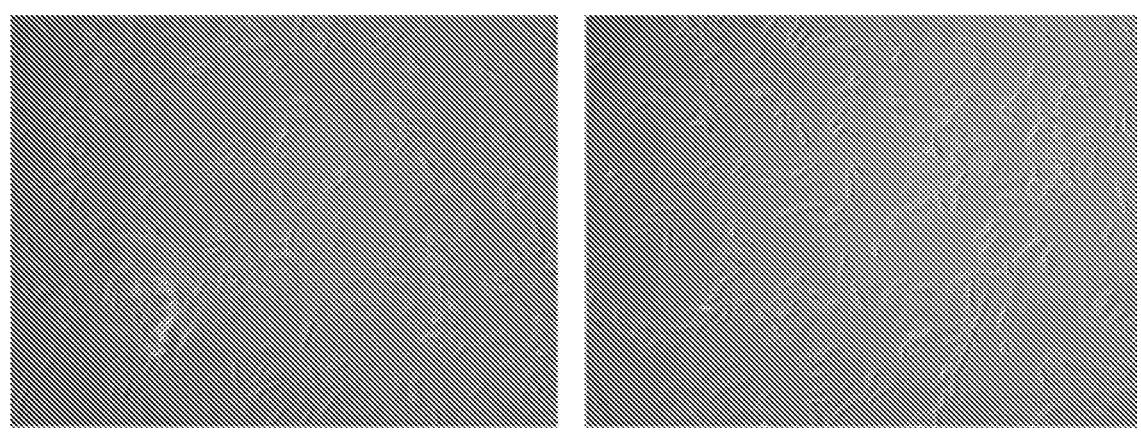
FIG. 24 depicts phase contrast microscopy (500×) of cultures of P. acnes K8 (left) and C3 (right) strains, as described in Experiment 2.2.

Experiment 1.3 was conducted to confirm the observations of Experiment 1.2 and to test whether the inoculation level could be reduced from 10% to 2%. $OD_{600}$ during cultivation is shown in FIG. 24. In agreement with the results of Experiment 1.2, a higher $OD_{600}$ was observed for strain C3 than for strain K8. The results also suggest that strain C3 grows slightly faster than strain K8. In addition, the results confirmed that it was possible to reduce the inoculation level to 2%. The $OD_{600}$ measurements indicated that the stationary phase was reached about 14 h and 18 h after inoculation for strain C3 and K8, respectively.

Part 2
Production of Placebo Sachets

Approximately 6000 sachets containing placebo gel medium were produced. The average quantity per sachet was 1.25 g (range 1.10 to 1.40 g). Microbiological analysis demonstrated that the material was free of Salmonella, Listeria monocytogenes, Enterobacteriaceae, sulphite-reducing clostridia and coagulase-positive staphylococci (Table 12).

TABLE 12

Results of analysis of pathogens in samples of gel medium with P. acnes and placebo gel medium.

| Pathogen | Gel with P.acnes | Placebo gel |
|---|---|---|
| Salmonella | Absent in 25 g | Absent in 25 g |
| Listeria monocytogenes | Absent in 25 g | Absent in 25 g |
| Enterobacteriaceae | <10 cfu/g | <10 cfu/g |
| Sulphite-reducing clostridia | <10 cfu/g | <10 cfu/g |
| Coagulase-positive staphylococci | <10 cfu/g | <10 cfu/g |

Production of Sachets with P. acnes

Strains C3 and K8 were cultivated. The fermentation period was 14 h. In agreement with Experiment 1.2 and 1.3, slightly higher $OD_{600}$ and viable count were observed for strain C3 than for strain K8. Based on $OD_{600}$ values, the concentrated cultures of strain C3 and K8 were mixed in a ratio of 47:53, to give a final ratio of 1:1 in the blend to which 1.5% HEC was added and which was packaged in sachets. Table 13 summarizes the results. Microscopic pictures of the bacteria (FIG. 24) showed the typical morphology of P. acnes. In addition to measurement of viable count, the concentration of bacteria was also determined by FACS flow cytometry (Table 4). This method can discriminate between live, damaged and dead cells by means of two different DNA dyes. The results for viable count and FACS-live cells were similar for both strains. The percentage of FACS-dead cells (percentage of the total) in the cultures of strain C3 and K8 was 18% and 40%. Unexpectedly, the percentage of FACS-dead cells in the concentrated cell suspensions were lower than in the cultures: 8% and 16% for C3 and K8, respectively.

TABLE 13

$OD_{600}$, viable count and FACS flow cytometry count of P. acnes strain C3 and strain K8 cultures before harvesting, after concentration of the bacteria in 0.25% peptone solution, after dilution and blending of the strains, and in gel medium from sachets (Experiment 2.2).

| | | Viable count | FACS (events/ml) | | | |
|---|---|---|---|---|---|---|
| Sample | $OD_{600}$ | (cfu/ml) | Live | Damaged | Dead | Total |
| Culture C3 | 4.9 | 5.4E+08 | 4.6E+08 | 3.3E+07 | 1.1E+08 | 6.1E+08 |
| Culture K8 | 3.8 | 4.5E+08 | 2.5E+08 | 3.3E+07 | 2.0E+08 | 4.9E+08 |
| Concentrate C3 | 54.3 | 5.3E+09 | 6.3E+09 | 1.0E+08 | 5.5E+08 | 7.0E+09 |
| Concentrate K8 | 48.4 | 5.6E+09 | 4.6E+09 | 3.5E+08 | 9.5E+08 | 5.9E+09 |
| Blend C3-K8[1] | 1.1 | — | — | — | — | — |
| Sachets #1000[2] | — | 3.8E+01 | — | — | — | — |
| Sachets #3500[2] | — | 3.8E+07 | — | — | — | — |
| Sachets #6000[2] | — | 4.3E+07 | — | — | — | — |
| Sachets #8500[2] | — | 4.3E+07 | — | — | — | — |
| Sachets, after 1 week at −80° C.[3] | — | 2.9E+07 | — | — | — | — |

[1]Prior to Addition of HEC
[2]Gel medium from 3 sachets, sampled after production of a 1000, 3500, 6000 and 8500 sachets
[3]Gel medium from 4 sachets A total of approximately 10,000 sachets were produced, of which 9000 sachets were packed in plastic bags (18 sachets per bag). The quantity of gel medium per sachet was adjusted to 1.2 g per sachet. This quantity enabled the removal of at least 1 mL from sachets upon regular opening and squeezing. The quantity of gel medium per sachets was measured every 500 to 1000 sachets (six replicates each time point). The quantity per sachet varied from 1.17 g to 1.38 g, with an average of 1.28 g. The total run time of the production of sachets was 7 h. The viable count of gel medium in sachets was determined four times in the course of the production run and varied between $3.8 \times 10^7$ and $4.3 \times 10^7$ cfu/ml, with an average of $4.0 \times 10^7$ cfu/ml (Table 13). Based on these results, the average viable count per sachet prior to storage at −80° C. was $5.1 \times 10^7$ cfu. The viable count of gel medium in sachets after 7 days storage at −80° C. was $2.9 \times 10^7$ cfu/ml (Table 4), corresponding to $3.7 \times 10^7$ cfu per sachet. Microbiological analysis demonstrated that the gel medium with the blend of P. acnes bacteria was free of Salmonella, Listeria monocytogenes, Enterobacteriaceae, sulphite-reducing clostridia and coagulase-positive staphylococci (Table 12). Table 14 shows the specifications of the laminated aluminum foil used for sachet production.

TABLE 14

Specifications of the laminated aluminum foil used for sachet production

| Article Number | Rev. | Valid from: | Aug. 14, 2014 |
|---|---|---|---|
| Article Description | DAKLAFILM ALU 12/7/15/100 | Specification no.: | 01 |

| Material Type | PET12/AL7/NY15/LDPE100 | | Material Specification | |
|---|---|---|---|---|
| PET | 12 μm | 16.44 g/m² | | |
| Adhesive | 2.5 μm | 3.0 g/m² | | |
| ALU | 7 μm | 18.9 g/m² | | |
| Adhesive | 2.5 μm | 3.0 g/m² | | |
| NY | 15 μm | 17.1 g/m² | | |
| Adhesive | 2.5 μm | 3.0 g/m² | | |
| LDPE | 100 μm | 92.3 g/m² | | |
| Total Thickness | 141.5 μm | Total Wt. | | |
| | | 153.74 g/m² | | |

| Characteristics | | | | | |
|---|---|---|---|---|---|
| Property | Value | Unit | Tolerance | Method | |
| Total Thickness | 141.5 | μm | +/−8% | DIN 53370 | |
| Material weight | 153.74 | g/m² | +/−8% | DIN EN ISO 2286-2 | |
| Seal Strength [before Steril] | >70.0 | N/15 mm | Min | DIN 55529 | |
| Laminating strength PET/ALU, | >3.0 | N/15 mm | Min | DIN 53357 | ASTM D-904-98 |
| Laminating strength ALU/NY, | >3.5 | N/15 mm | Min | DIN 53357 | ASTM D-904-98 |
| Laminating strength NY/LDPE, | >3.5 | N/15 mm | Min | DIN 53357 | ASTM D-904-98 |
| Oxygen transmission | 0.0 | cm³/m² × d × bar | Max | DIN 53380 | ASTM D-3985-81 |
| Water vapour transmission | 0.0 | g/m² × d | Max | ISO 15106 | ASTM F-1249 |
| Residual solvent | 8.0 | mg/m² | Max | DIN 13628-2 | |

Field of application
For Food; Non Food
Foodstuff Certificates
Confirmation must be listed on a Test Certificate according to EN 10204.
All materials must be listed in EG regulations 2000/72/EG and amendments, as well as in BlR and FDA.

Summary

The medium composition for cultivation of *P. acnes* C3 and K8 was modified by using an alternative source of yeast extract and inclusion of peptone. The *P. acnes* strains were grown in pH-controlled fermenters in 14 h to final biomass yields of $OD_{600}$ of 4.0 to 5.0, corresponding to approximately $5 \times 10^8$ cfu/ml. A total of more than 9000 sachets containing $5.1 \times 10^7$ cfu/sachet of a 1:1 blend of *P. acnes* strains C3 and K8 were produced and stored at −80° C.

The modifications of the cultivation procedure (alternative yeast extract source, inclusion of peptone in the medium, and cultivation in pH-controlled fermenters) resulted in 5 to 10 times higher yield of *P. acnes* C3 and K8.

The ratio between viable count and $OD_{600}$ was quite consistent throughout the experiments: $5 \times 10^7$ to $1 \times 10^8$ cfu/ml for cultures or suspensions with $OD_{600}$ 1.0. This cell concentration is low in comparison with cultures of many other bacteria, for instance *Lactobacillus* species, *Lactococcus* species and *Escherichia coli*. This suggests that the *P. acnes* cells are larger than cells of these species.

The concentration of *P. acnes* in sachets stored for 1 week at −80° C. was only slightly lower than the concentration prior to freezing ($4.0 \times 10^7$ and $2.9 \times 10^7$ cfu/ml respectively) (Table 4), indicating that the bacteria survived the freezing event well.

Example 7: Large Scale Clinical Study

Based on the analysis of the pilot study, the following aspects were incorporated into a large scale clinical study: formulation A2 was selected for testing; 23 subjects were allocated to the active arm and 23 to the placebo arm; strain-level analysis of some species in the microbiome is included; and an optimized disinfection protocol is included to increase the rate of acceptors. Acne patients were selected at least in part based on those that had higher counts of lesions, and higher acne grade, and if they were subjects with pure teenage acne (excluding hormonal acne, adult acne etc.).

Subjects are individuals with facial acne vulgaris grade 1.5-4 (Leeds scale). Subjects include both males and females, aged 16-23 years old.

Figure 8B:
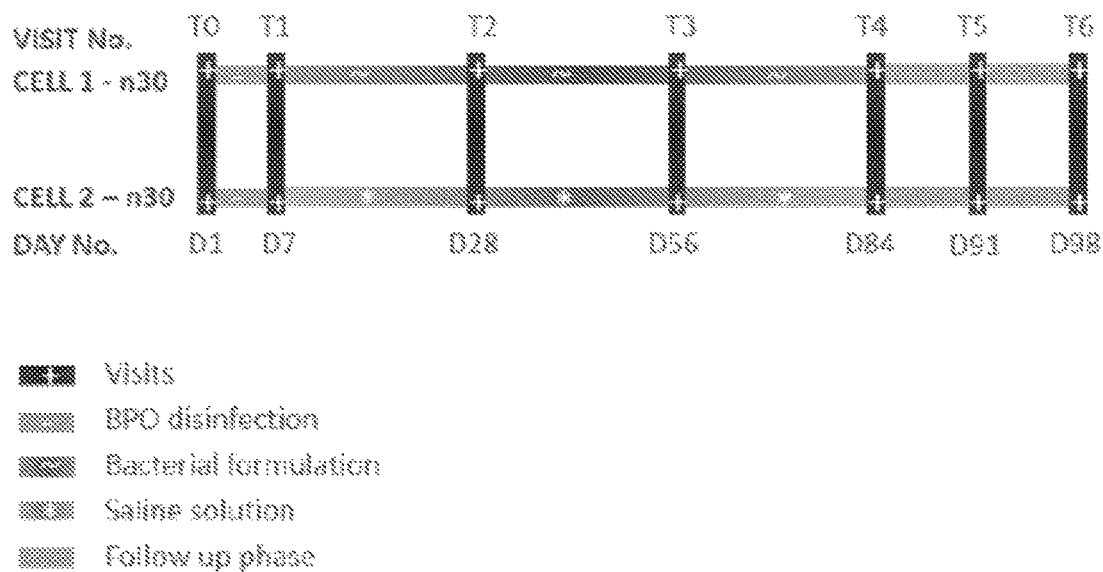
FIG. 8B depicts an administration schedule for a larger clinical study.

On day 1, all subjects receive a benzoyl peroxide product (Akneroxid gel 50 mg/g, Almirall) to apply once a day on the face for 7 days (day 1-7). On Day 8, subjects receive the test product (either bacterial product or placebo). Subjects apply the test product to the face twice a day (morning and evening) after washing the face. Subjects keep applying the product for 11 weeks (day 8-day 84). After this phase, there is a 2-week follow up phase without any application. Measurements and samples are taken on day 1, day 7, day 28, day 56, day 84, day 91 and day 98 (Table 8, FIG. 8B). In Table 8, "X" indicates which method of analysis is conducted on each indicated day of the study.

TABLE 8

| | Large Clinical Study | | | | | | |
|---|---|---|---|---|---|---|---|
| | Lesion count | Safety | Image | Microbiome sample | Sebu-tape | Sebu-meter | pH |
| D1 | X | X | X | X | X | X | X |
| D7 | | X | X | X | | X | X |
| D28 | X | X | X | X | X | X | X |
| D56 | X | X | X | X | X | X | X |
| D84 | X | X | X | X | X | X | X |

TABLE 8-continued

Large Clinical Study

|  | Lesion count | Safety | Image | Microbiome sample | Sebu-tape | Sebu-meter | pH |
|---|---|---|---|---|---|---|---|
| D91 |  | X | X | X |  | X | X |
| D98 | X | X | X | X | X | X | X |

Measurement Methods

Lesion count is conducted visually by a trained investigator. Safety evaluation is assessed by the investigator or a study nurse by visual evaluation of the redness, irritation or any other skin problems. An image is taken at each visit. During the pilot phase study discussed in Example 5, a normal camera was used, while in the larger clinical study, imaging is conducted by visible, cross-polarized or blue fluorescent light taken by a trained investigator or a study nurse to document the state of the skin.

Lipid analysis using a sebumeter is conducted by a study nurse. Lipid analysis using sebutape provides more details on the content and quantity of sebum in the skin. For the measurement, skin of the subject is prepared by degreasing the test area with 70% isopropanol impregnated swab or similar product. The sebutape is then placed for 30 minutes on the skin (forehead) of the subject to take the measurement.

The pH analysis is performed by using a skin pH-meter. It is a non-invasive instant method without any preparation of the skin.

Microbiome analysis using sterile swab is a non-invasive instant method in which a swab is moved over the skin, rotating for 30 seconds to collect the bacterial community living on the surface of the skin.

Microbiome analysis using a strip 3-S-Biokit (Skin surface Technology) allows for reaching bacterial communities in the follicles. It is a non-invasive method in which a plastic strip with a drop of skin-friendly cyanoacrylate is gently pressed on the skin and left to dry for 1 minute. Then it is gently removed. In reactive skin, redness can be observed for a few minutes after removing the strip. However, longer or more pronounced irritation is not expected.

Statistical Methods

For continuous variables, number, mean, median, standard error, minimum and maximum are assessed given. The significance threshold is 5%.

A descriptive analysis is performed on the inclusion data. The inclusion and non-inclusion criteria are described (number and percentage) and the deviation is listed. Withdrawal patients are also described (number and percentage) and reasons for stopping are listed.

The primary analysis is carried out in the intention-to-treat population which contains all patients that are randomized and have at least one post-baseline visit. Sensitivity analyses are carried out in the per-protocol population comprising all patients with complete data and without major protocol violations. Safety analyses are carried out in the safety population covering all patients that received at least one treatment with microbes (experimental or control).

Sample size calculation: The sample size calculation is based on the efficacy endpoint in total lesions, as data about the expected change in the bacterial population are not available. In a previous acne study at the University Clinic of Dermatology in Magdeburg (Thielitz et al., 2015) three different gels were compared. Over a treatment period of 12 weeks, averaged over the three treatments, a reduction of the count of total lesions of 40%±32% (mean±standard deviation) was observed. A similar effect in the active treatment group of the larger clinical study described herein is expected. In the control group, a residual effect (by trial attended measures and placebo effect) of up to about 15% reduction could be observed. Accordingly, a sample size of at least 27 patients per study arm is included to detect a difference in a two-sided t test with error level 0.05 and 80% power. Including an additional 10% of subjects to compensate for diluting effects of drop outs, 30 patients per treatment arm are included. If not all 60 patients can be recruited in one cohort, an adaptive design with an interim analysis is executed. A first cohort will be run, and after completion of this cohort, an analysis of the change of the microbiome composition is conducted. If already a clear and statistically significant signal for a change of the microbiome composition is observed, then the clinical parameters will be evaluated. If the clinical parameters also show a statistically significant result, then the study will be closed and a full analysis run. If the results are not statistically significant, or if the statistical significance of the results is unclear, then a second cohort of patients is tested.

Efficacy analysis: Efficacy is considered at two different levels—the change in the composition of bacteria and in clinical parameters (primary: total lesion count, secondary: sebum production).

Descriptive analyses: For both treated and not treated subjects, a descriptive analysis is performed at each time of evaluation (Pilot: Day 1, Day 7, Day 21 and Day 42; Larger clinical study: Day 1, Day 7, Day 28, Day 56, Day 84, and Day 112) and on the differences (Day of evaluation—D0). The number, mean, median, standard error, minimum and maximum are given.

Analysis for primary clinical endpoint: The total lesion counts are considered as percentages of the baseline measurement for each patient (or logarithm of it if the distribution is skewed). The difference from baseline to week 12 is compared between both study arms in a linear mixed model for repeated measures including all visits after baseline until week 12, enabling the inclusion of patients with missing values at some visits without explicit imputation techniques. Fixed factors are the treatment arm and gender and the absolute baseline count of total lesions and age as co-variables. If the test for the treatment effect is significant ($p<0.05$) then the analog test is carried for the difference in the counts from baseline to week 16 also at level 0.05. This hierarchical procedure ensures error level control over both steps. As secondary analysis, the whole procedure is carried out in the per-protocol population.

Analysis of secondary clinical endpoints: The secondary clinical endpoints are treated analogously to the primary clinical endpoint.

Analysis of bacterial composition: The primary analysis of the bacterial composition comprises the relative abundances of the four bacterial strains that are compounds of the active treatment. The analysis is done analogously to the primary endpoint, but at a Bonferroni-adjusted significance level of $0.05/4=0.0125$ for the parallel assessment of four bacterial strains.

For secondary multivariate analyses, microbiome differences are computed comparing the vectors that describe the microbiome. Each position of the vector contains a number, indicating the number of times that a certain strain has been detected. Correlation distance is used to measure differences between different microbiomes. Further, the distance of the *P. acnes* microbiome towards the composition of the applied mixture is calculated using the same method as above. A simple spearman correlation can be used, but other statistical methods can also be applied. Further analyses include comparison of the distribution of the different bacteria (e.g., expressed as Shannon index) and its stability over time between both study arms.

REFERENCES

Allgaier, H., Jung, G., Werner, R. G., Schneider, U., and Zähner, H. (1986). Epidermin: sequencing of a heterodetic tetracyclic 21-peptide amide antibiotic. Eur. J. Biochem. FEBS 160, 9-22.

Azoulay, L., Oraichi, D., and Bérard, A. (2007). Isotretinoin therapy and the incidence of acne relapse: a nested case-control study. Br. J. Dermatol. 157, 1240-1248.

Barnard, E., Liu, J., Yankova, E., Cavalcanti, S. M., Magalhaes, M., Li, H., Patrick, S., and McDowell, A. (2016). Strains of the Propionibacterium acnes type III lineage are associated with the skin condition progressive macular hypomelanosis. Sci. Rep. 6, 31968.

Bek-Thomsen, M., Lomholt, H. B., and Kilian, M. (2008). Acne is not associated with yet-uncultured bacteria. J. Clin. Microbiol. 46, 3355-3360.

Belkaid, Y., and Segre, J. A. (2014). Dialogue between skin microbiota and immunity. Science 346, 954-959.

Berson, D. S., Chalker, D. K., Harper, J. C., Leyden, J. J., Shalita, A. R., and Webster, G. F. (2003). Current concepts in the treatment of acne: report from a clinical roundtable. Cutis 72, 5-13.

Brüggemann, H., Lomholt, H. B., Tettelin, H., and Kilian, M. (2012). CRISPR/cas loci of type II Propionibacterium acnes confer immunity against acquisition of mobile elements present in type I P. acnes. PloS One 7, e34171.

Churruca, I., Fernández-Quintela, A., and Portillo, M. P. (2009). Conjugated linoleic acid isomers: differences in metabolism and biological effects. BioFactors Oxf. Engl. 35, 105-111.

Clavaud, C., Jourdain, R., Bar-Hen, A., Tichit, M., Bouchier, C., Pouradier, F., El Rawadi, C., Guillot, J., Ménard-Szczebara, F., Breton, L., et al. (2013). Dandruff Is Associated with Disequilibrium in the Proportion of the Major Bacterial and Fungal Populations Colonizing the Scalp. PLoS ONE 8, e58203.

Consortium, T. H. M. P. (2012). Structure, function and diversity of the healthy human microbiome. Nature 486, 207-214.

Doré, J., and Blottière, H. (2015). The influence of diet on the gut microbiota and its consequences for health. Curr. Opin. Biotechnol. 32C, 195-199.

Downing, D. T., Stewart, M. E., Wertz, P. W., and Strauss, J. S. (1986). Essential fatty acids and acne. J. Am. Acad. Dermatol. 14, 221-225.

Draelos, Z. D. (2009). Cosmeceuticals: undefined, unclassified, and unregulated. Clin. Dermatol. 27, 431-434.

Fitz-Gibbon, S., Tomida, S., Chiu, B.-H., Nguyen, L., Du, C., Liu, M., Elashoff, D., Erfe, M. C., Loncaric, A., Kim, J., et al. (2013). Propionibacterium acnes strain populations in the human skin microbiome associated with acne. J. Invest. Dermatol. 133, 2152-2160.

Flores, G. E., Henley, J. B., and Fierer, N. (2012). A Direct PCR Approach to Accelerate Analyses of Human-Associated Microbial Communities. PLoS ONE 7.

Götz, F., Perconti, S., Popella, P., Werner, R., and Schlag, M. (2014). Epidermin and gallidermin: Staphylococcal lantibiotics. Int. J. Med. Microbiol. IJMM 304, 63-71.

Grice, E. A., and Segre, J. A. (2011). The skin microbiome. Nat. Rev. Microbiol. 9, 244-253.

Holmes, A. D. (2013). Potential role of microorganisms in the pathogenesis of rosacea. J. Am. Acad. Dermatol. 69, 1025-1032.

Hong Lioe Ko, S., Heczko, P. B., and Pulverer, G. (1978). Differential Susceptibility of Propionibacterium acnes, P. granulosum and P. avidum to Free Fatty Acids. J. Invest. Dermatol. 71, 363-365.

Hunyadkürti, J., Feltóti, Z., Horváth, B., Nagymihály, M., Vörös, A., McDowell, A., Patrick, S., Urbań, E., and Nagy, I. (2011). Complete Genome Sequence of Propionibacterium acnes Type IB Strain 6609. J. Bacteriol. 193, 4561-4562.

Iinuma, K., Sato, T., Akimoto, N., Noguchi, N., Sasatsu, M., Nishijima, S., Kurokawa, I., and Ito, A. (2009). Involvement of Propionibacterium acnes in the Augmentation of Lipogenesis in Hamster Sebaceous Glands In Vivo and In Vitro. J. Invest. Dermatol. 129, 2113-2119.

Kasimatis, G., Fitz-Gibbon, S., Tomida, S., Wong, M., and Li, H. (2013). Analysis of complete genomes of Propionibacterium acnes reveals a novel plasmid and increased pseudogenes in an acne associated strain. BioMed Res. Int. 2013, 918320.

Kearney, J. N., Ingham, E., Cunliffe, W. J., and Holland, K. T. (1984). Correlations between human skin bacteria and skin lipids. Br. J. Dermatol. 110, 593-599.

King, K., Jones, D. H., Daltrey, D. C., and Cunliffe, W. J. (1982). A double-blind study of the effects of 13-cis-retinoic acid on acne, sebum excretion rate and microbial population. Br. J. Dermatol. 107, 583-590.

Kong, H. H., Oh, J., Deming, C., Conlan, S., Grice, E. A., Beatson, M. A., Nomicos, E., Polley, E. C., Komarow, H. D., Murray, P. R., et al. (2012). Temporal shifts in the skin microbiome associated with disease flares and treatment in children with atopic dermatitis. Genome Res. 22, 850-859.

Letawe, C., Boone, M., and Piérard, G. E. (1998). Digital image analysis of the effect of topically applied linoleic acid on acne microcomedones. Clin. Exp. Dermatol. 23, 56-58.

Leyden, J. (2001). Current issues in antimicrobial therapy for the treatment of acne. J. Eur. Acad. Dermatol. Venereol. 15, 51-55.

Lomholt, H. B., and Kilian, M. (2010). Population Genetic Analysis of Propionibacterium acnes Identifies a Subpopulation and Epidemic Clones Associated with Acne. PLoS ONE 5.

Madli Puhvel, S., and Reisner, R. M. (1970). Effect of Fatty Acids on the Growth of Corynebacterium Acnes in Vitro. J. Invest. Dermatol. 54, 48-52.

Makrantonaki, E., Ganceviciene, R., and Zouboulis, C. (2011). An update on the role of the sebaceous gland in the pathogenesis of acne. Dermatoendocrinol. 3, 41-49.

McDowell, A., Barnard, E., Nagy, I., Gao, A., Tomida, S., Li, H., Eady, A., Cove, J., Nord, C. E., and Patrick, S. (2012). An Expanded Multilocus Sequence Typing Scheme for Propionibacterium acnes: Investigation of "Pathogenic", "Commensal" and Antibiotic Resistant Strains. PLoS ONE 7, e41480.

McLane, J. (2001). Analysis of common side effects of isotretinoin. J. Am. Acad. Dermatol. 45, S188-194.

Mourelatos, K., Eady, E. a., Cunliffe, W. j., Clark, S. m., and Cove, J. h. (2007). Temporal changes in sebum excretion and propionibacterial colonization in preadolescent children with and without acne. Br. J. Dermatol. 156, 22-31.

Moya-Camarena, S. Y., Heuvel, J. P. V., Blanchard, S. G., Leesnitzer, L. A., and Belury, M. A. (1999). Conjugated linoleic acid is a potent naturally occurring ligand and activator of PPARα. J. Lipid Res. 40, 1426-1433.

NIH HMP Working Group, Peterson, J., Garges, S., Giovanni, M., McInnes, P., Wang, L., Schloss, J. A., Bonazzi, V., McEwen, J. E., Wetterstrand, K. A., et al. (2009). The NIH Human Microbiome Project. Genome Res. 19, 2317-2323.

van Nood, E., Vrieze, A., Nieuwdorp, M., Fuentes, S., Zoetendal, E. G., de Vos, W. M., Visser, C. E., Kuijper, E. J., Bartelsman, J. F. W. M., Tijssen, J. G. P., et al. (2013). Duodenal Infusion of Donor Feces for Recurrent *Clostridium difficile*. N. Engl. J. Med. 368, 407-415.

Oh, J., Byrd, A. L., Deming, C., Conlan, S., NISC Comparative Sequencing Program, Kong, H. H., and Segre, J. A. (2014). Biogeography and individuality shape function in the human skin metagenome. Nature 514, 59-64.

Olle, B. (2013). Medicines from microbiota. Nat. Biotechnol. 31, 309-315.

Pappas, A., Johnsen, S., Liu, J.-C., and Eisinger, M. (2009). Sebum analysis of individuals with and without acne. Dermatoendocrinol. 1, 157-161.

Pierre, A.-S., Minville-Walz, M., Fevre, C., Hichami, A., Gresti, J., Pichon, L., Bellenger, S., Bellenger, J., Ghiringhelli, F., Narce, M., et al. (2013). Trans-10, cis-12 conjugated linoleic acid induced cell death in human colon cancer cells through reactive oxygen species-mediated ER stress. Biochim. Biophys. Acta BBA—Mol. Cell Biol. Lipids 1831, 759-768.

Rivier, M., Castiel, I., Safonova, I., Ailhaud, G., and Michel, S. (2000). Peroxisome proliferator-activated receptor-alpha enhances lipid metabolism in a skin equivalent model. J. Invest. Dermatol. 114, 681-687.

Rohland, N., and Reich, D. (2012). Cost-effective, high-throughput DNA sequencing libraries for multiplexed target capture. Genome Res. 22, 939-946.

Ross, J. I., Snelling, A. M., Eady, E. A., Cove, J. H., Cunliffe, W. J., Leyden, J. J., Collignon, P., Dréno, B., Reynaud, A., Fluhr, J., et al. (2001). Phenotypic and genotypic characterization of antibiotic-resistant *Propionibacterium acnes* isolated from acne patients attending dermatology clinics in Europe, the U.S.A., Japan and Australia. Br. J. Dermatol. 144, 339-346.

Rosson, R. A., Grund, A. D., Deng, M.-D., and Sanchez-Riera, F. (2004). Linoleate isomerase.

Schnell, N., Entian, K. D., Schneider, U., Götz, F., Zähner, H., Kellner, R., and Jung, G. (1988). Prepeptide sequence of epidermin, a ribosomally synthesized antibiotic with four sulphide-rings. Nature 333, 276-278.

Scholz, C. F. P., Jensen, A., Lomholt, H. B., Brüggemann, H., and Kilian, M. (2014). A Novel High-Resolution Single Locus Sequence Typing Scheme for Mixed Populations of *Propionibacterium acnes* In Vivo. PLoS ONE 9, e104199.

Sörensen, M., Mak, T. N., Hurwitz, R., Ogilvie, L. A., Mollenkopf, H. J., Meyer, T. F., and Brüggemann, H. (2010). Mutagenesis of *Propionibacterium acnes* and analysis of two CAMP factor knock-out mutants. J. Microbiol. Methods 83, 211-216.

Tripathi, S. V., Gustafson, C. J., Huang, K. E., and Feldman, S. R. (2013). Side effects of common acne treatments. Expert Opin. Drug Saf. 12, 39-51.

Wang, Y., Kuo, S., Shu, M., Yu, J., Huang, S., Dai, A., Two, A., Gallo, R. L., and Huang, C.-M. (2014). *Staphylococcus epidermidis* in the human skin microbiome mediates fermentation to inhibit the growth of *Propionibacterium acnes*: implications of probiotics in acne vulgaris. Appl. Microbiol. Biotechnol. 98, 411-424.

Wang, L., Clavaud, C., Bar-Hen, A., Cui, M., Gao, J., Liu, Y., Liu, C., Shibagaki, N., Guéniche, A., Jourdain, R., et al. (2015). Characterization of the major bacterial-fungal populations colonizing dandruff scalps in Shanghai, China, shows microbial disequilibrium. Exp. Dermatol. 24, 398-400.

Westerhof, W., Relyveld, G. N., Kingswijk, M. M., de Man, P., and Menke, H. E. (2004). *Propionibacterium acnes* and the pathogenesis of progressive macular hypomelanosis. Arch. Dermatol. 140, 210-214.

Zhao, L. (2010). Genomics: The tale of our other genome. Nature 465, 879-880.

Zouboulis, C. C. (2004). Acne and sebaceous gland function. Clin. Dermatol. 22, 360-366.

(2012). Special human Microbiota issue. Nature 486.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. The entire disclosure of WO2016/172196, filed on Apr. 20, 2016, entitled "Methods and Compositions for Changing the Composition of the Skin Microbiome Using Complex Mixtures of Bacterial Strains" is incorporated by reference herein in its entirety.

The invention claimed is:

1. A composition for topical administration to the skin comprising: (i) a live *Propionibacterium acnes* (*P. acnes*) bacterial strain, wherein the live *P. acnes* bacterial strain is a *P. acnes* single-locus sequence typing (SLST) type K8 strain; and (ii) one or more of a thickener, buffer, or carrier, wherein the composition is stable at room temperature for at least three months.

2. The composition of claim 1, wherein the thickener comprises hydroxyethyl cellulose, starch, gum, kaolin, hydrated aluminum silicate, fumed silica, carboxyvinyl polymer, sodium carboxymethyl cellulose, ethylene glycol monostearate, or sodium alginate.

3. The composition of claim 1, wherein the concentration of the thickener is from about 1%-5%.

4. The composition of claim 1 wherein the composition further comprises a *P. acnes* SLST type C3 strain.

5. The composition of claim 1, wherein the composition includes at least $10^4$ colony-forming units per milliliter (CFU/ml) of the live *P. acnes* bacterial strain.

6. The composition of claim 1, wherein the composition is in the form of a gel, cream, ointment, lotion, or powder and/or wherein the composition is part of a two-component dispensing system.

7. The composition of claim 1, further comprising an additional *P. acnes* bacterial strain selected from the group consisting of: D1, H1, H2, H3, K1, K2, K4, K6, K9, and L1 SLST type strains.

8. The composition of claim 1, wherein the composition does not include a ribotype 6 (RT6) strain of *P. acnes*.

9. The composition of claim 1, wherein the composition does not include a Phylotype III strain of *P. acnes*.

10. The composition of claim 1, wherein the composition is not naturally occurring.

11. A method comprising administering the composition of claim 1 to a subject, optionally wherein the subject is a human subject.

12. The method of claim 11, wherein the method comprises improving the appearance of the skin and/or maintaining healthy skin.

13. The method of claim 11, wherein the method comprises treating a condition selected from the group consisting of: acne, oily skin, progressive macular hypomelanosis, dandruff, atopic eczema, atopic dermatitis and rosacea.

14. The method of claim 11, wherein the method comprises administering the composition to a subject who also receives or has previously received treatment with a disinfectant or an antibiotic.

15. A composition for topical administration to the skin comprising two or more different live *Propionibacterium acnes* (*P. acnes*) bacterial strains, wherein the composition comprises a live *P. acnes* single-locus sequence typing (SLST) type K8 strain and a live *P. acnes* SLST type C3 strain, and wherein the composition is stable at room temperature for at least three months.

16. The composition of claim 1, wherein prior to forming a composition, (i) and (ii) are comprised within a two-component dispensing system.

17. The composition of claim 16, wherein the live *P. acnes* bacterial strain in (i) is freeze-dried prior to forming a composition.

18. The composition of claim 17, wherein (i) further comprises a *P. acnes* SLST type C3 strain.

* * * * *